(12) United States Patent
Nagrath et al.

(10) Patent No.: US 10,935,550 B2
(45) Date of Patent: Mar. 2, 2021

(54) FUNCTIONALIZED GRAPHENE OXIDE SYSTEM FOR DETECTING RARE CELLS

(71) Applicant: The Regents of the University of Michigan, Ann Arbor, MI (US)

(72) Inventors: Sunitha Nagrath, Ann Arbor, MI (US); Hyeun Joong Yoon, Brookings, SD (US)

(73) Assignee: The Regents of the University of Michigan, Ann Arbor, MI (US)

(*) Notice: Subject to any disclaimer, the term of this patent is extended or adjusted under 35 U.S.C. 154(b) by 250 days.

(21) Appl. No.: 15/423,881

(22) Filed: Feb. 3, 2017

(65) Prior Publication Data

US 2017/0146529 A1  May 25, 2017

Related U.S. Application Data

(63) Continuation of application No. 14/347,073, filed as application No. PCT/US2012/058013 on Sep. 28, 2012, now Pat. No. 9,645,149.

(60) Provisional application No. 61/541,814, filed on Sep. 30, 2011.

(51) Int. Cl.
  *G01N 33/551* (2006.01)
  *G01N 33/574* (2006.01)
  *G01N 33/553* (2006.01)
  *B82Y 15/00* (2011.01)
  (Continued)

(52) U.S. Cl.
  CPC .......... *G01N 33/574* (2013.01); *B01L 3/5027* (2013.01); *B82Y 15/00* (2013.01); *G01N 33/54353* (2013.01); *G01N 33/54386* (2013.01); *G01N 33/553* (2013.01); *G01N 33/57492* (2013.01); *B01L 2300/0896* (2013.01)

(58) Field of Classification Search
  None
  See application file for complete search history.

(56) References Cited

U.S. PATENT DOCUMENTS 5,376,252 A  12/1994  Ekstrom et al.
5,770,528 A   6/1998  Mumick et al.
5,776,487 A   7/1998  Maxfield Wilson et al.
(Continued)

FOREIGN PATENT DOCUMENTS

EP  1 214 361 A   2/2001
EP  2 335 075 A   3/2010
(Continued)

OTHER PUBLICATIONS

US 9,568,475 B2, 02/2017, Nagrath et al. (withdrawn)
(Continued)

*Primary Examiner* — Christopher L Chin
(74) *Attorney, Agent, or Firm* — Howard & Howard Attorneys PLLC

(57) ABSTRACT

This disclosure provides a system for detecting rare cells. The system includes a substrate, an extension coupled to the substrate and extending outwardly from the substrate, and a functionalized graphene oxide disposed on the extension. This disclosure also provides a method for detecting rare cells using the system of this disclosure. The method includes the steps of providing the system and introducing a sample of bodily fluid to the system such that the sample interacts with the functionalized graphene oxide.

22 Claims, 40 Drawing Sheets

(51) Int. Cl.
*B01L 3/00* (2006.01)
*G01N 33/543* (2006.01)

(56) References Cited

U.S. PATENT DOCUMENTS

| | | | |
|---|---|---|---|
| 6,485,690 | B1 | 11/2002 | Pfost et al. |
| 6,803,019 | B1 | 10/2004 | Bjornson et al. |
| 7,179,867 | B2 | 2/2007 | Chang et al. |
| 7,332,288 | B2 | 2/2008 | Terstappen et al. |
| 7,846,393 | B2 | 12/2010 | Tai et al. |
| 8,548,219 | B2 | 10/2013 | Ortyn et al. |
| 9,140,697 | B2 | 9/2015 | Tseng et al. |
| 2004/0005582 | A1 | 1/2004 | Shipwash |
| 2004/0137300 | A1 | 7/2004 | Gemmen et al. |
| 2005/0181463 | A1 | 8/2005 | Rao et al. |
| 2006/0160243 | A1 | 7/2006 | Tang et al. |
| 2007/0224591 | A1 | 9/2007 | Gui et al. |
| 2007/0263477 | A1 | 11/2007 | Sudarsan et al. |
| 2008/0267845 | A1 | 10/2008 | Hoglund et al. |
| 2009/0303472 | A1 | 12/2009 | Zhao et al. |
| 2010/0028681 | A1 | 2/2010 | Dai et al. |
| 2010/0068105 | A1 | 3/2010 | Green |
| 2010/0255479 | A1 | 10/2010 | Mikolajczyk et al. |
| 2010/0255581 | A1 | 10/2010 | Naqvi et al. |
| 2011/0091864 | A1 | 4/2011 | Karlsson et al. |
| 2011/0096327 | A1 | 4/2011 | Papautsky et al. |
| 2011/0104732 | A1* | 5/2011 | Lucic .................... C12M 23/02 435/29 |
| 2011/0189650 | A1 | 8/2011 | Ayliffe et al. |
| 2012/0003711 | A1 | 1/2012 | Tseng et al. |
| 2012/0040843 | A1 | 2/2012 | Ducree et al. |
| 2012/0209116 | A1 | 8/2012 | Hossack et al. |
| 2012/0300576 | A1 | 11/2012 | Li et al. |
| 2013/0129829 | A1 | 5/2013 | He |
| 2013/0236881 | A1* | 9/2013 | Spatz ................. B81C 1/00031 435/5 |
| 2013/0261266 | A1 | 10/2013 | Bunyard et al. |
| 2014/0024131 | A1* | 1/2014 | Kim ...................... G01N 21/658 436/172 |
| 2014/0186426 | A1 | 7/2014 | Tseng et al. |
| 2014/0315213 | A1 | 10/2014 | Nagrath et al. |
| 2015/0285808 | A1 | 10/2015 | Nagrath et al. |
| 2015/0293010 | A1 | 10/2015 | Nagrath et al. |
| 2015/0337128 | A1 | 11/2015 | Gray et al. |
| 2016/0291019 | A1 | 10/2016 | Yoon et al. |

FOREIGN PATENT DOCUMENTS

| | | |
|---|---|---|
| WO | WO 01/09198 A1 | 2/2001 |
| WO | WO 2009/051734 A1 | 4/2009 |
| WO | WO 2010/028160 A1 | 3/2010 |
| WO | WO 2010/108003 A2 | 9/2010 |
| WO | WO 2010/124227 A2 | 10/2010 |
| WO | WO 2011/049963 A2 | 4/2011 |
| WO | WO 2011/094279 A1 | 8/2011 |
| WO | WO 2012/094642 A2 | 7/2012 |
| WO | WO 2013/049636 A1 | 4/2013 |
| WO | WO 2013/116523 A1 | 8/2013 |
| WO | WO 2014/022581 A1 | 2/2014 |
| WO | WO 2014/036951 A1 | 3/2014 |
| WO | WO 2014/072465 A1 | 5/2014 |
| WO | WO 2014/120265 A1 | 8/2014 |

OTHER PUBLICATIONS

Vancoillie, Gertjan et al., "Thermoresponsive Poly(oligo ethylene glycol acrylates)", Progress in Polymer Science, vol. 39, 2014, pp. 1074-1093.
Maheswaran et al., "Detection of Mutations in EGFR in Circulating Lung-Cancer Cells", The New England Journal of Medicine, Jul. 24, 2008, pp. 366-377.
Marrinucci et al., "Case study of the morphologic variation of circulating tumor cells", Human Pathology, vol. 38, 2007, pp. 514-519.
Marrinucci et al., "Cytomorphology of circulating colorectal tumor cells:a small case series", Journal of Oncology, Article I.D. 861341, 2010, pp. 1-7.
Mikolajczyk et al., "Detection of EpCAM-Negative and Cytokeratin-Negative Circulating Tumor Cells in Peripheral Blood", Journal of Oncology, 2011, pp. 1-10.
Miller et al. "Significance of Circulating Tumor Cells Detected by the Cellsearch System in Patients with Metastatic Breast Colorectal and Prostate Cancer", Journal of Oncology, Hindawi Publishing Corporation, vol. 2010, Article ID 617421, pp. 1-8.
Mittal et al. "Antibody-Functionalized Fluid-Permeable Surfaces for Rolling Cell Capture at High Flow Rates", Biophysical Journal, vol. 102, Feb. 2012, pp. 721-730.
Mittal et al. "Discontinuous Nanoporous Membranes Reduce Non-Specific Fouling for Immunoaffinity Cell Capture" Small, vol. 9, No. 24, 2013, pp. 4207-4214.
Mohanty et al. "Graphene-based single-bacterium resolution biodevice and DNA transistor: interfacing graphene derivatives with nanoscale and microscale biocomponents" Nano Lett 8, 2008, pp. 4469-4476.
Molloy et al. "The prognostic significance of tumour cell detection in the peripheral blood versus the bone marrow in 733 early-stage breast cancer patients" Breast Cancer Research 13, R61, 2011, 11 pages.
Mueller et al. "Prognostic impact of circulating tumor cells assessed with CellSearch System(TM) and AdnaTest Breast(TM) in metastatic breast cancer patients: the DETECT study" Breast Cancer Research 14:R118, 2012, 8 pages.
Murlidhar et al., "A radial flow microfluidic device for ultra-high-throughput affinity-based isolation of circulating tumor cells", Small, vol. 10, No. 23, 2014, pp. 4895-4904.
Nagrath et al. "Isolation of rare circulating tumour cells in cancer patients by microchip technology" Nature 450, 2007,pp. 1235-1239.
Nakamura et al., "Uptake and release of budesonide from mucoadhesive, pH-sensitive copolymers and their application to nasal delivery", Journal of Controlled Release 61, 1999, pp. 329-335.
Nanguzgambo et al., Immunochemistry and lung cancer: application in diagnosis, prognosis and targeted therapy:, Oncology, vol. 80, 2011 pp. 247-256.
Nejlund et al. "In vitro detection of CTCs with the CytoTrack method", a poster presentation retrieved from www.cytotrack.dk/page12 on Apr. 16, 2014, 1 page.
Nitschke et al., "Thermo-responsive poly(NiPAAm-co-DEGMA) substrates for gentle harvest of human corneal endothelial cell sheets", Journal of Biomedical Materials Research Part A, 80A, 2007, pp. 1003-1010.
Novoselov et al. "Two-dimensional gas of massless Dirac fermions in graphene" Nature, vol. 438, Issue 7065, Nov. 2005, pp. 197-200.
Nygaard et al. "Method comparison of CTC detection with CytoTrack and CellSearch", a poster presentation retrieved from www.cytotrack.dk/page12 on Apr. 16, 2014, 1 page.
Okumura et al., "Circulating Tumor Cells in Pulmonary Venous Blood of Primary Lung Cancer Patients", The Annals of thoracic surgery, vol. 87, 2009, pp. 1669-1675.
Ozkumur et al. "Inertial Focusing for Tumor Antigen-Dependent and-Independent Sorting of Rare Circulating Tumor Cells", Science Translational Medicine, vol. 5, Issue 179, Apr. 3, 2013, pp. 1-11.
Pant et al., "Processing and characterization of electrospun graphene oxide/polyurethane composite nanofibers for stent coating", Chemical Engineering Journal, 270, 2015, pp. 336-342.
Pantel et al., "Circulating Tumour Cells in Cancer Patients: Challenges and Perspectives", Trends. Mol. Med. 2010, 16(9), pp. 398-406.
Pantel et al. "Detection, clinical relevance and specific biological properties of disseminating tumour cells" Nat Rev Cancer 8, 2008, pp. 329-340.
Pantel et al., "Functional Studies on Viable Circulating Tumor Cells", Clinical Chemistry, vol. 62, No. 2, 2015, pp. 328-334.
Park et al. "Chemical methods for the production of graphenes" Nature Nanotechnology, vol. 4, Apr. 2009, pp. 217-224.
Park et al. "Graphene oxide papers modified by divalent ions-enhancing mechanical properties via chemical cross-linking" ACS Nano 2, 2008, pp. 572-578.

(56) References Cited

OTHER PUBLICATIONS

Paterlini-Brechot et al., "Circulating tumor cells (CTC) detection: Clinical impact and future directions", Cancer Letters 253, 2007, pp. 180-204.
Peeters et al., "Circulating tumour cells and lung microvascular tumour cell retention in patients with metastatic breast and cervical cancer", Cancer Letters, vol. 356, 2015, pp. 872-879.
Pierce Biotechnology, Inc., "GMBS and Sulfo-GMBS" Rockford, IL, Jul. 2005, retrieved from http://www.piercenet.com/instructions/2161763.pdf on Apr. 16, 2014, 3 pages.
Pirozzi et al., "Prognostic value of cancer stem cells, epithelial-mesenchymal transition and circulating tumor cells in lung cancer", Oncology Reports, vol. 29, 2013, pp. 1763-1768.
Poveda et al., "Circulating tumor cells predict progression free survival and overall survival in patients with relapsed/recurrent advanced ovarian cancer", Gynecologic Oncology, vol. 122, 2011, pp. 567-572.
Powell et al. "Single Cell Profiling of Circulating Tumor Cells: Transcriptional Heterogeneity and Diversity from Breast Cancer Cell Lines", PLoS one, vol. 7, Issue 5, May 2012, pp. 1-11.
Punnoose et al. "Evaluation of Circulating Tumor Cells and Circulating Tumor DNA in Non-Small Cell Lung Cancer: Association with Clinical Endpoints in a Phase 11 Clinical Trial of Pertuzumab and Erlotinib", Clinical Cancer Research, 2012, pp. 2391-2401.
Punnoose et al. "Molecular Biomarker Analyses Using Circulating Tumor Cells" PLoS One vol. 5, Issue 9, e12517, 2010, 12 pages.
Rahbari et al., "Compartmental differences of circulating tumor cells in colorectal cancer", Annals of Surgical Oncology, vol. 19, 2012, pp. 2195-2202.
Ramanathan et al. "Functionalized graphene sheets for polymer nanocomposites" Nat Nanotechnol 3, 2008 pp. 327-331.
Reategui et al., "Tunable Nanostructured Coating for the Capture and Selective Release of Viable Circulating Tumor Cells", Adv. Mater, 27, 2015, pp. 1593-1599.
Reddy et al., "Pulmonary venous blood sampling significantly increases the yield of circulating tumor cells in early-stage lung cancer", The Journal of Thoracic and Cardiovascular Surgery, 2015, pp. 852-858.
Riethdorf et al. "Detection of Circulating Tumor Cells in Peripheral Blood of Patients with Metastatic Breast Cancer: A Validation Study of the CellSearch System" Clin Cancer Res 13, 2007, pp. 920-928.
Roy et al. "New directions in thermoresponsive polymers", The Royal Society of Chemistry, 2013, pp. 7214-7243.
Rudin et al. "Phase II Study of Single-Agent Navitoclax (ABT-263) and Biomarker Correlates in Patients with Relapsed Small Cell Lung Cancer", Clinical Cancer Research, Jun. 1, 2012, pp. 3163-3169.
Sahoo et al., "Functionalized carbon nanomaterials as nanocarriers for loading and delivery of a poorly water-soluble anticancer drug: a comparative study", Chemical Communications, 47, 2011, pp. 5235-5237.
Sarioglu et al., "A microfluidic device for label-free, physical capture of circulating tumor cell clusters", Nature Methods, vol. 12, No. 7, 2015, pp. 685-691.
Schmittgen et al., "Analyzing real-time PCR data by the comparative C(T) method", Nature Protocols, vol. 3, No. 3, 2008, pp. 1101-1108.
Sequist et al., "An Exciting New Tool to Detect Circulating Tumor Cells in Lung Cancer Patients", Journal of Thoracic Oncology, vol. 4, No. 3, Mar. 2009, pp. 281-283.
Shah et al., "Biopolymer System for Cell Recovery from Microfluidic Cell Capture Devices" American Chemical Society Publications, 2012, pp. 3682-3688.
Shanker et al., "Microfluidic Device with Polyer-Graphene Oxide Composite Platform for Efficient Capture and Release of Circulating Tumor Cells," University of Michigan, Date: 2015, 1 page.
Shao et al. "Graphene based electrochemical sensors and biosensors: A review", Electroanalysis 22, No. 10, 2010, pp. 1027-1036.
Sheng et al. "Aptamer-Enabled Efficient Isolation of Cancer Cells from Whole Blood Using a Microfluidic Device" Analytical Chemistry 84, 2012, pp. 4199-4206.
Sienel et al., "Tumour cells in the tumour draining vein of patients with non-small cell lung cancer: detection rate and clinical significance", European Journal of Cardio-Thoracic Surgery: Official Journal of the European Association for Cardio-thoracic Surgery, vol. 23, 2003, pp. 451-456.
Hayes et al. "Circulating Tumor Cells at Each Follow-up Time Point during Therapy of Metastatic Breast Cancer Patients Predict Progression-Free and Overall Survival", Clin Cancer Res 12, 2006, pp. 4218-4224.
Hillig et al. "In vitro validation of an ultra-sensitive scanning fluorescence microscope for analysis of Circulating Tumor Cells", APMIS 2013 published by John Wiley & Sons Ltd, 7 pages.
Hillig et al. "Monitoring CTC in metastatic breast cancer patients using the CytoTrack method", a poster presentation retrieved from www.cytrotrack.dk/page12 on Apr. 16, 2014, 1 page.
Hirsch et al., "Early detection of lung cancer: clinical perspectives of recent advances in biology and radiology", Clinical Cancer Research: An Official Journal of the American Association for Cancer Research, vol. 7, Jan. 2001, pp. 5-22.
Hoshino et al. "Microchip-based immunomagnetic detection of circulating tumor cells", Lab Chip, 2011, pp. 3449-3457.
Hoshino et al., "Preparation of a New Thermo-Responsive Adsorbent with Maltose as a Ligand and Its Application to Affinity Precipitation", Biotechnol Bioeng., 60, 1998, pp. 568-579.
Hou et al. "Capture and Stimulated Release of Circulating Tumor Cells on Polymer-Grafted Silicon Nanostructures", Advanced Materials, 2013, pp. 1547-1551.
Hou et al. "Circulating Tumor Cells as a Window on Metastasis Biology in Lung Cancer", The American Journal of Pathology, vol. 178, No. 3, Mar. 2011, pp. 989-996.
Hou et al., "Clinical significance and molecular characteristics of circulating tumor cells and circulating tumor microemboli in patients with small-cell lung cancer", Journal of Clinical Oncology: Official Journal of the American Society of Clinical Oncology, vol. 30, No. 5, Feb. 10, 2012, pp. 525-532.
Hou et al. "Isolation and retrieval of circulating tumor cells using centrifugal faces", Scientific Reports, 2013, pp. 1-8.
Huber et al., "Programmed Adsorption and Release of Proteins in a Microfluidic Device", Science 301, 2003, pp. 352-355.
Hu et al., "Quantum-Dot-Tagged Reduced Graphene Oxide Nanocomposites for Bright Fluorescence Bioimaging and Photothermal Therapy Monitored In Situ", Advanced Materials, 24, 2012, pp. 1748-1754.
Hummers et al. "Preparation of graphitic oxide", Journal of the American Chemical Society, vol. 80, Mar. 1958, p. 1339.
Ithimakin et al., "HER2 Drives Luminal Breast Cancer Stem Cells in the Absence of HER2 Amplification: Implications for Efficacy of Adjuvant Trastuzumab", Cancer Research, 73, 2013, pp. 1635-1646.
Iniesta et al., "Biological and clinical significance of MMP-2, MMP-9, TIMP-1 and TIMP-2 in non-small cell lung cancer", Oncology Reports, vol. 17, 2007, pp. 217-223.
Jung et al. "A graphene oxide based immuno-biosensor for pathogen detection", Angew. Chem. 122, 2010, pp. 5844-5847.
Kaiser "Cancer's Circulation Problem", Science 327, 2010, pp. 1072-1074.
Kamande et al., "Modular Microsystem for the Isolation, Enumeration, and Phenotyping of Circulating Tumor Cells in Patients with Pancreatic Cancer", Analytical Chemistry 85, 2013, pp. 9092-9100.
Karabacak et al. "Microfluidic, marker-free isolation of circulating tumor cells from blood samples", Nature Protocols, vol. 9, No. 3, 2014, pp. 694-710.
Ke et al. "Programming Thermoresponsiveness of Nano Velcro Substrates Enables Effective Purification of Circulating Tumor Cells in Lung Cancer Patients", American Chemical Society, vol. 9, No. 1, 2015, pp. 62-70.
Khoja et al. "A pilot study to explore circulating tumour cells in pancreatic cancer as a novel biomarker" British Journal of Cancer, 2012, pp. 508-516.

(56) References Cited

OTHER PUBLICATIONS

Kim et al., "Graphene Oxide-Polyethylenimine Nanoconstruct as a Gene Delivery Vector and Bioimaging Tool", Bioconjugate Chemistry, 22, 2011, pp. 2558-2567.

Kim et al. "Nanomedicine", New England Journal of Medicine 363, 2010, pp. 2434-2443.

Krebs et al., "Analysis of circulating tumor cells in patients with non-small cell lung cancer using epithelial marker-dependent and -independent approaches", Journal of Thoracic Oncology: Official Publication of the International Association for the Study of Lung Cancer, vol. 7, No. 2, 2012, pp. 306-315.

Koukourakis et al., "Enhanced expression of SPARC/osteonectin in the tumor-associated stroma of non-small cell lung cancer is correlated with markers of hypoxia/acidity and with poor prognosis of patients", Cancer Research, vol. 33, Sep. 1, 2003, pp. 5376-5380.

Kumar et al., "Chemical Functionalization of Graphene to Augment Stem Cell Osteogenesis and Inhibit Biofilm Formation on Polymer Composites for Orthopedic Applications", ACS Applied Materials & Interfaces, 7, 2015, pp. 3237-3252.

Kuntaegowdanahalli et al., "Inertial Microfluidics for Continuous Particle Separation in Spiral Microchannels", Lab on a Chip, vol. 9, 2009, pp. 2973-2980.

Kurkuri et al. "Plasma functionalized PDMS microfluidic chips: towards point-of-care capture of circulating tumor cells", Journal of Materials Chemistry 21, 2011, pp. 8841-8848.

Lecharpentier et al., "Detection of circulating tumour cells with a hybrid (epithelial/mesenchymal) phenotype in patients with metastatic non-small cell lung cancer", British Journal of Cancer, vol. 105, 2011, pp. 1338-1341.

Lee et al. "Nanowire Substrate-Based Laser Scanning Cytometry for Quantitation of Circulating Tumor Cells", Nano Letters 12, 2012, pp. 2697-2704.

Li et al. "Highly conducting graphene sheets and Langmuir-Blodgett films", Nat. Nano. 3, 2008, pp. 538-542.

Li et al., "Organo- and Water-Dispersible Graphene Oxide-Polymer Nanosheets for Organic Electronic Memory and Gold Nanocomposites", Journal of Physical Chemistry C, 114, 2010, p. 12742-12748.

Li et al. "Processable aqueous dispersions of graphene nanosheets", Nature Nanotechnology, vol. 3, 2008, pp. 101-105.

Lin et al. "Nanostructure Embedded Microchips for Detection, Isolation, and Characterization of Circulating Tumor Cells", Account of Chemical Research, 2014, pp. 2941-2950.

Lin et al. "Portable Filter-Based Microdevice for Detection and Characterization of Circulating Tumor Cells", Clinical Cancer Research 16, 2010, pp. 5011-5018.

Liotta et al., "The significance of hematogenous tumor cell clumps in the metastatic process", Cancer Research, vol. 36, Mar. 1976, pp. 889-894.

Liu et al. "Biocompatable graphene oxide-based glucose biosensors", Langmuir 26(9), 2010, pp. 6158-6160.

Liu et al. "High throughout capture of circulating tumor cells using an integrated microfluidic system", Biosensors and Bioelectronics, 2013, pp. 113-119.

Liu et al., "Hydrophobic Interaction-Mediated Capture and Release of Cancer Cells on Thermoresponsive Nanostructured Surfaces", Advanced Materials 25, 2013, pp. 922-927.

Liu et al. "Intercalation of Organic Ammonium Ions into Layered Graphite Oxide", Langmuir 18, 2002, pp. 4926-4932.

Liu et al. "PEGylated nanographene oxide for delivery of water-insoluble cancer drugs", J Am Chem Soc 130, 2008, pp. 10876-10877.

Liu et al. "Preparation of carbon nanotube bioconjugates for biomedical applications", Nat. Protocols 4, 2009, pp. 1372-1381.

Liu et al. "Supramolecular chemistry on water-soluble carbon nanotubes for drug loading and delivery", ACS Nanovol. 1, 2007, pp. 50-56.

Livak et al., "Analysis of relative gene expression data using real-time quantitative PCR and the 2(-Delta Delta C(T)) Method", Methods, vol. 25, 2001, pp. 402-408.

Loh et al. "Graphene oxide as a chemically tunable platform for optical applications", Nat Chem 2, 2010, pp. 1015-1024.

Lopez-Riquelme et al. "Imaging cytometry for counting circulating tumor cells: comparative analysis of the CellSearch vs. ImageStream systems", APMIS, 121, published by John Wiley & Sons Ltd., 2013, pp. 1139-1143.

Lortent-Tieulentet al., "International trends in lung cancer incidence by histological subtype: adenocarcinoma stabilizing in men but still increasing in women", Lung Cancer, vol. 84, 1014, pp. 13-22.

Lu et al. "A Graphene Platform for Sensing Biomolecules" Angew Chem Int Ed Engl 48, 2009, pp. 4785-4787.

Luo et al., "Epithelial-mesenchymal plasticity of breast cancer stem cells: implications for metastasis and therapeutic resistance", Current Pharmaceutical Design, vol. 21, 2015, pp. 1301-1310.

Maheswaran et al., "Circulating tumor cells: a window into cancer biology and metastasis", Current Opinion in Genetics & Development 20, 2010, pp. 96-99.

Smirnov et al., "Global Gene Expression Profiling of Circulating Tumor Cells", American Association for Cancer Research, Jun. 15, 2005, pp. 4993-4997.

Stankovich et al. "Graphene-based composite materials" Nature 442, 2006, pp. 282-286.

Stankovich et al. "Synthesis and exfoliation of isocyanate-treated graphene oxide nanoplatelets" Carbon, vol. 44, 2006, pp. 3342-3347.

Stile et al., "Thermo-Responsive Peptide-Modified Hydrogels for Tissue Regeneration", Biomacromolecules, 2, 2001, pp. 185-194.

Stott et al., "Isolation and characterization of circulating tumor cells from patients with localized and metastatic prostate cancer", Science Translational Medicine, vol. 2, Issue 25, 2010, pp. 1-10.

Sun et al. "Circulating tumor cells: advances in detection methods, biological issues, and clinical relevance" J Cancer Research Clinical Oncology, 2011, pp. 1151-1173.

Sun et al., "Nano-Graphene Oxide for Cellular Imaging and Drug Delivery", Nano Research 1, 2008, pp. 203-212.

Suzuki et al., "Aberrant methylation of SPARC in human lung cancers", British Journal of Cancer, vol. 92, 2005, pp. 942-948.

Thampi et al., "Mechanical characterization of high-performance graphene oxide incorporated aligned fibroporous poly(carbonate urethane) membrane for potential biomedical applications", Journal of Applied Polymer Science, 2015, pp. 132-139.

Ting et al., "Single-cell RNA sequencing identifies extracellular matrix gene expression by pancreatic circulating tumor cells", Cell Reports, vol. 8, 2014, pp. 1905-1918.

Tjensvoll et al. "Circulating tumor cells in pancreatic cancer patients: Methods of detection and clinical implications" Int. J. Cancer: 134, 2014, pp. 1-8.

Tymosiak-Zielinska et al. "Interfacial properties of polycrystalline gold electrodes in tetraalkylammonium electrolytes" Electrochimica Acta 46, 2001, pp. 3073-3082.

Wang et al. "Chemical self-assembly of graphene sheets" Nano Research, vol. 2, Feb. 2009, pp. 336-342.

Wang et al. "Highly efficient capture of circulating tumor cells by using nanostructured silicon substrates with integrated chaotic micromixers", Angewandte Chemmie International Edition, vol. 50, Issue 13, Mar. 4, 2011, pp. 3084-3088 (Mar. 4, 2011).

Wang et al., "Nanostructured substrates for isolation of circulating tumor cells", Nano Today 8, 2013, pp. 374-387.

Wang et al. "Three-Dimensional Nanostructured Substrates toward Efficient Capture of Circulating Tumor Cells" Angewandte Chemie 121, 2009, pp. 9132-9135.

Wei et al. "The assembly of single-layer graphene oxide and graphene using molecular templates" Nano Letters, vol. 8, Aug. 2008, pp. 3141-3145, Aug. 2008.

Wendel et al., "Fluid biopsy for circulating tumor cell identification in patients with early-and late-stage non-small cell lung cancer: a glimpse into lung cancer biology", Physical Biology, vol. 9, 2012, pp. 1-9.

Wicha et al., Circulating tumor cells: not all detected cells are bad and not all bad cells are detected. Journal of Clinical Oncology: Official Journal of the American Society of Clinical Oncology, vol. 29, 2011, pp. 1508-1511.

(56) References Cited

OTHER PUBLICATIONS

Wikipedia, "Bovine serum albumin" http://en.wikipedia.org/wiki/Bovine_serum_albumin, retrieved Sep. 29, 2011, 1 Page.
Wikipedia, "Epithelial cell adhesion molecule" http://en.wikipedia.org/wiki/Epithelial_cell_adhesion_moledcule, retrieved Sep. 29, 2011, 1 Page.
Wikipedia, "Phosphate buffered saline" http://en.wikipedia.org/wiki/Phosphate_buffered_saline, retrieved Sep. 29, 2011, 1 page.
Willipinski-Stapelfeldt et al. "Changes in Cytoskeletal Protein Composition Indicative of an Epithelial-Mesenchymal Transition in Human Micrometastatic and Primary Breast Carcinoma Cells" Clinical Cancer Research 11, 2005, 2005, pp. 8006-8014.
Wu et al., "Preliminary investigation of the clinical significance of detecting circulating tumor cells enriched from lung cancer patients", Journal of Thoracic Oncology: Official Publication of the International Association for the Study of Lung Cancer, vol. 4, No. 1, 2009, pp. 30-36.
Wu et al., "Supercapacitors Based on Flexible Graphene/Polyaniline Nanofiber Composite Films", ACS Nano, 4, 2010, pp. 1963-1970.
Xia et al. "An index for characterization of nanomaterials in biological systems" Nat Nano 5, 2010, pp. 671-675.
Xu et al. "Aptamer-based microfluidic device for enrinchment, sorting, and detection of multiple cancer cells" J. Analytical Chemistry, 81 (17), 2009, pp. 7436-7442.
Yoon et al., "Emerging Role of Nanomaterials in Circulating Tumor Cell Isolation and Analysis", ACS Nano 8, 2014, pp. 1995-2017.
Yoon et al. "Nanoassembly of graphene oxide for circulating tumor cell isolation" MicroTAS 2011 Conference, Oct. 2-6, 2011, Seatle WA (www.microtas2011.org).
Yoon et al. "Sensitive capture of circulating tumour cells by functionalized graphene oxide nanosheets" Nature Nanotechnology vol. 8 (Oct. 2013), 8 pages.
Yoon et al. "Sensitive Detection of circulating tumor cells by graphene oxide nanoassembly" AIChE Annual Meeting 2011, Oct. 16-21, 2011, Minneapolis MN (www.aiche.org/Conferences/AnnualMeeting/index.aspx), 1 page.
Yu et al., "Circulating breast tumor cells exhibit dynamic changes in epithelial and mesenchymal composition", Science, vol. 339, Feb. 1, 2013, pp. 580-584.
Yu et al. "Circulating tumor cells: approaches to isolation and characterization" The Journal of Cell Biology 192, 2011, pp. 373-382.
Yu et al., "RNA sequencing of pancreatic circulating tumour cells implicates WNT signalling in metastasis", Nature, vol. 487, Jul. 26, 2012, pp. 510-514.
Zhang et al. "Binding Affinities/Avidities of Antibody-Antigen Interactions: Quantification and Scale-Up Implications", Biotechnology and Bioengineering, vol. 95, No. 5, Dec. 5, 2006, pp. 812-829.
Zhang et al. "Electrospun TiO2 Nanofiber-Based Cell Capture Assay for Detecting Circulating Tumor Cells from Colorectal and Gastric Cancer Patients", Advanced Materials 24, 2012, pp. 2756-2760.
Zhang et al. "Experimental observation of the quantum Hall effect and Berry's phase in graphene", Nature, vol. 438, Issue 7065, Nov. 2005, pp. 201-204.
Zhang et al. "Microfluidics and cancer: are we there yet?", Biomedical Microdevices 15, 2013, pp. 595-609.
Zheng et al. "A high-performance microsystem for isolating circulating tumor cells", Lab Chip, The Royal Society of Chemistry, 2011, pp. 3269-3276.
Zheng et al. "Membrane microfilter device for selective capture, electrolysis and genomic analysis of human circulating tumor cells", Journal of Chromatography A 1162, pp. 154-161 (2007).
Zhuang et al., "Conjugated-Polymer-Functionalized Graphene Oxide: Synthesis and Nonvolatile Rewritable Memory Effect", Adv. Mater., 22, 2010, pp. 1731-1735.
"Circulating tumor cells: the Grand Challenge", Lab Chip, The Royal Society of Chemistry, 2011, pp. 375-377.

International Search Report for Application No. PCT/US2012/058013 dated Feb. 14, 2013, 4 pages.
U.S. Appl. No. 61/541,814, filed Sep. 30, 2011.
English language abstract for WO 2014/036951 extracted from espacenet.com database on May 25, 2016, 2 pages.
Aceto et al., "Circulating tumor cell clusters are oligoclonal precursors of breast cancer metastasis," Cell, 158, Aug. 28, 2014, pp. 1110-1122.
Adams et al. "Highly efficient circulating tumor cell isolation from whole blood and label-free enumeration using polymer-based microfluidics with an integrated conductivity sensor", J. Am. Chemical Society, 130, 2007, pp. 8633-8641.
Aguirre-Ghiso et al., "Targeting dormant cancer," Nature Medicine, vol. 19, No. 3, Mar. 2013, pp. 276-277.
Alix-Panabieres et al., "Challenges in circulating tumour cell research", Nature Reviews, Cancer, vol. 14, Sep. 2014, pp. 623-631.
Allard et al. "Tumor Cells Circulate in the Peripheral Blood of All Major Carcinomas but not in Healthy Subjects or Patients With Nonmalignant Diseases", Clinical Cancer Research 10, 2004, pp. 6897-6904.
Amnis Corporation, "Brochure for ImageStreamX, Imaging Flow Cytometer", 2012, 16 pages.
Andreopoulou et al. "Comparison of assay methods for detection of circulating tumor cells in metastatic breast cancer: AdnaGen AdnaTest Breast Cancer Select/Detect(TM) versus Veridex CellSearch(TM) system", Int. J. Cancer: 130, 2012, pp. 1590-1597.
Antolovic et al. "Heterogeneous detection of circulating tumor cells in patients with colorectal cancer by immunomagnetic enrichment using different EpCAM-specific antibodies", BMC Biotechnology 10, 35, 2010, 8 pages.
Arya et al., "Enrichment, detection and clinical significance of circulating tumor cells", Lab on a Chip, 13, 2013, pp. 1995-2027.
Baccelli et al., "Identification of a population of blood circulating tumor cells from breast cancer patients that initiates metastasis in a xenograft assay", Nature Biotechnology, vol. 31, No. 6, Jun. 2013, pp. 539-544.
Barreto et al. "Nanomaterials: Applications in Cancer Imaging and Therapy" Advanced Materials 23, 2011, pp. H18-H40.
Bednarz-Knoll et al. "Plasticity of disseminating cancer cells in patients with epithelial malignancies" Cancer and Metastasis Reviews, Jun. 26, 2012, 15 pages.
Bhagat et al., Inertial Microfluidics for Continuous Particle Filtration and Extraction, Microfluidics and Nanofluidics, vol. 7, No. 2, 2008, pp. 217-226.
Bhagat et al., "Pinched flow coupled shear-modulated inertial microfluidics for high-throughput rare blood cell separation", Lab on a Chip, The Royal Society of Chemistry, www.rsc.org/loc 2011, pp. 1870-1878.
Bissolati et al., "Portal vein-circulating tumor cells predict liver metastases in patients with resectable pancreatic cancer", Tumour Biology: The Journal of the International Society for Oncodevelopmental Biology and Medicine, 2015, pp. 991-996.
Brechot et al., "Circulating tumor cells (CTC) detection: Clinical impact and future directions", Science Direct, www.sciencedirect.com, 2006, pp. 180-204.
Brongersma et al., "Plasmon-induced hot carrier science and technology", Nat. Nano. 10, 2015, pp. 25-34.
Carlsson et al., "Circulating tumor microemboli diagnostics for patients with non-small-cell lung cancer", Journal of Thoracic Oncology: Official Publication of the International Association for the Study of Lung Cancer, vol. 9, No. 8, Aug. 2014, pp. 1111-1119.
Cecchet et al., "One Step Growth of Protein Antifouling Surfaces: Monolayers of Poly(ethylene oxide) (PEO) Derivatives on Oxidized and Hydrogen-Passivated Silicon Surfaces", Langmuir: the ACS Journal of Surfaces and Colloids, 22, 2006, pp. 1173-1181.
Chaudhuri et al., "Myoblast differentiation of human mesenchymal stem cells on graphene oxide and electrospun graphene oxide-polymer composite fibrous meshes: importance of graphene oxide conductivity and dielectric constant on their biocompatibility", Biofabrication, 7, 2015, pp. 1-13.
Chen et al., "Aptamer-Enabled Efficient Isolation of Cancer Cells from Whole Blood Using a Microfluidic Device", Anal. Chem., 1:84(9), May 1, 2012, pp. 4199-4206.

(56) References Cited

OTHER PUBLICATIONS

Cogswell et al., "A Planar Labyrinth Micromixer", Proceedings of the 14th International Heat Transfer Conference IHTC14, Aug. 8-13, 2010, 5 pages.

Cohen et al. "Relationship of Circulating Tumor Cells to Tumor Response, Progression-Free Survival, and Overall Survival in Patients With Metastatic Colorectal Cancer" Journal of Clinical Oncology 26, 2008, pp. 3213-3221.

Cristofanilli et al. "Circulating Tumor Cells, Disease Progression, and Survival in Metastatic Breast Cancer", New England Journal of Medicine 351, 2004, pp. 781-791.

Cunliffe et al., "Bacterial adsorption to thermoresponsive polymer surfaces", Biotechology Letters 22, 2000, pp. 141-145.

Das et al., "Graphene-Based Polymer Composites and Their Applications", Polymer—Plastics Technology and Engineering, 52, 2013, pp. 319-331.

De Bono et al. "Circulating Tumor Cells Predict Survival Benefit from Treatment in Metastatic Castration-Resistant Prostate Cancer", Clinical Cancer Research 14, 2008, pp. 6302-6309.

Dickson et al., "Efficient capture of circulating tumor cells with a novel immunocytochemical microfluidic device" AIP Biomicrofluidics, 2011, pp. 1-16.

Dikin et al. "Preparation and characterization of graphene oxide paper", Nature 448, 2007, pp. 457-460.

Dharmasiri et al. "Highly efficient capture and enumeration of low abundance prostate cancer cells using prostate-specific membrane antigen aptamers immobilized to a polymeric microfluidic device", Electrophoresis, 2009, pp. 3289-3300.

Dobrovolskaia et al. "Immunological properties of engineered nanomaterials", Nat Nano 2, 2007, pp. 469-478.

Dong et al. "Microfluidics and Circulating Tumor Cells", The Journal of Molecular Diagnostics, 2012, pp. 1-9.

Dreyer et al. "The chemistry of graphene oxide", Chemical Society Reviews 39, 2010, pp. 228-240.

Eda et al. "Large-area ultrathin films of reduced graphene oxide as a transparent and flexible electronic material", Nat, Nano 3, 2008, pp. 270-274.

Fan et al. "Clinical significance of circulating tumor cells detected by an invasion assay in peripheral blood of patients with ovarian cancer", Gynecologic Oncology 112, 2009, pp. 185-191.

Farace et al. "A direct comparison of CellSearch and ISET for circulating tumour-cell detection in patients with metastic carcinomas", British Journal of Cancer 105, 2011, pp. 847-853.

Fehm et al. "Detection and characterization of circulating tumor cells in blood of primary breast cancer patients by RT-PCR and comparison to status of bone marrow disseminated cells", Breast Cancer Research 11:R59, 2009, 9 pages.

Fehm et al. "HER2 status of circulating tumor cells in patients with metastatic breast cancer: a prospective, multicenter trial", Breast Cancer Res. Treat, 124, 2010, pp. 403-412.

Funaki et al., "Novel approach for detection of isolated tumor cells in pulmonary vein using negative selection method: morphological classification and clinical implications", European Journal of Cardio-Thoracic Surgery: Official Journal of the European Association for Cardio-Thoracic Surgery, vol. 40, 2011, pp. 322-327.

Funaki et al., "Significance of tumour vessel invasion in determining the morphology of isolated tumour cells in the pulmonary vein in non-small-cell lung cancer", European Journal of Cardio-Thoracic Surgery: Official Journal of the European Association for Cardio-thoracic Surgery, vol. 43, 2013, pp. 1126-1130.

Geim et al. "The rise of graphene", Nature Materials, vol. 6, 2007, pp. 183-191.

Gleghorn et al. "Capture of circulating tumor cells from whole blood of prostate cancer patients using geometrically enhanced differential immunocapture (GEDI) and a prostate-specific antibody", Lab on a Chip 10, 2010, pp. 27-29.

Gossett et al., "Label-Free Cell Separation and Sorting in Microfluidic Systems", Analytical and Bioanalytical Chemistry, vol. 397, No. 8, 2010, pp. 3249-3267.

Gupta et al., "Cancer Metastasis: Building a Framework", Massague, Cell 127, 2006, pp. 679-695.

Haber et al., "Blood-based analyses of cancer: circulating tumor cells and circulating tumor DNA" Cancer Discovery, Jun. 2014, pp. 650-651.

Hanahan et al., "Hallmarks of Cancer: The Next Generation", Cell, 144, Mar. 4, 2011, pp. 646-674.

Hatch et al., "Engineered Alginate Hydrogels for Effective Microfluidic Capture and Release of Endothelial Progenitor Cells from Whole Blood", Langmuir, 27, 2011, pp. 4257-4264.

Hashimoto et al., "Significant increase in circulating tumour cells in pulmonary venous blood during surgical manipulation in patients with primary lung cancer", Interactive Cardiovascular and Thoracic Surgery, vol. 18, 2014, pp. 775-783.

Haugaard et al. "In vitro detection of CTCs with the CytoTrack method", a poster presentation retrieved from www.cytotrack.dk/page12 on Apr. 16, 2014, 1 page.

* cited by examiner

| A | |
|---|---|
| From | To |
| 2 | 500 |
| 4 | 498 |
| 6 | 496 |
| 8 | 494 |
| 10 | 492 |
| 12 | 490 |
| 14 | 488 |
| 16 | 486 |
| 18 | 484 |
| 20 | 482 |
| 22 | 480 |
| 24 | 478 |
| 26 | 476 |
| 28 | 474 |
| 30 | 472 |
| 32 | 470 |
| 34 | 468 |
| 36 | 466 |
| 38 | 464 |
| 40 | 462 |
| 42 | 460 |
| 44 | 458 |
| 46 | 456 |
| 48 | 454 |
| 50 | 452 |
| 52 | 450 |
| 54 | 448 |
| 56 | 446 |
| 58 | 444 |
| 60 | 442 |

| | |
|---|---|
| 62 | 440 |
| 64 | 438 |
| 66 | 436 |
| 68 | 434 |
| 70 | 432 |
| 72 | 430 |
| 74 | 428 |
| 76 | 426 |
| 78 | 424 |
| 80 | 422 |
| 82 | 420 |
| 84 | 418 |
| 86 | 416 |
| 88 | 414 |
| 90 | 412 |
| 92 | 410 |
| 94 | 408 |
| 96 | 406 |
| 98 | 404 |
| 100 | 402 |
| 102 | 400 |
| 104 | 398 |
| 106 | 396 |
| 108 | 394 |
| 110 | 392 |
| 112 | 390 |
| 114 | 388 |
| 116 | 386 |
| 118 | 384 |
| 120 | 382 |
| 122 | 380 |
| 124 | 378 |

| | |
|---|---|
| 126 | 376 |
| 128 | 374 |
| 130 | 372 |
| 132 | 370 |
| 134 | 368 |
| 136 | 366 |
| 138 | 364 |
| 140 | 362 |
| 142 | 360 |
| 144 | 358 |
| 146 | 356 |
| 148 | 354 |
| 150 | 352 |
| 152 | 350 |
| 154 | 348 |
| 156 | 346 |
| 158 | 344 |
| 160 | 342 |
| 162 | 340 |
| 164 | 338 |
| 166 | 336 |
| 168 | 334 |
| 170 | 332 |
| 172 | 330 |
| 174 | 328 |
| 176 | 326 |
| 178 | 324 |
| 180 | 322 |
| 182 | 320 |
| 184 | 318 |
| 186 | 316 |
| 188 | 314 |

| | |
|---|---|
| 190 | 312 |
| 192 | 310 |
| 194 | 308 |
| 196 | 306 |
| 198 | 304 |
| 200 | 102 |
| 202 | 300 |
| 204 | 298 |
| 206 | 296 |
| 208 | 294 |
| 210 | 292 |
| 212 | 290 |
| 214 | 288 |
| 216 | 286 |
| 218 | 284 |
| 220 | 282 |
| 222 | 280 |
| 224 | 278 |
| 226 | 276 |
| 228 | 274 |
| 230 | 272 |
| 232 | 270 |
| 234 | 268 |
| 236 | 266 |
| 238 | 264 |
| 240 | 262 |
| 242 | 260 |
| 244 | 258 |
| 246 | 256 |
| 248 | 254 |
| 250 | 252 |

FIG. 25A

| B | | 200 | 1805 | 405 | 1600 | 610 | 1395 | 815 | 1190 |
|---|---|---|---|---|---|---|---|---|---|
| From | To | 205 | 1800 | 410 | 1595 | 615 | 1390 | 820 | 1185 |
| 5 | 2000 | 210 | 1795 | 415 | 1590 | 620 | 1385 | 825 | 1180 |
| 10 | 1995 | 215 | 1790 | 420 | 1585 | 625 | 1380 | 830 | 1175 |
| 15 | 1990 | 220 | 1785 | 425 | 1580 | 630 | 1375 | 835 | 1170 |
| 20 | 1985 | 225 | 1780 | 430 | 1575 | 635 | 1370 | 840 | 1165 |
| 25 | 1980 | 230 | 1775 | 435 | 1570 | 640 | 1365 | 845 | 1160 |
| 30 | 1975 | 235 | 1770 | 440 | 1565 | 645 | 1360 | 850 | 1155 |
| 35 | 1970 | 240 | 1765 | 445 | 1560 | 650 | 1355 | 855 | 1150 |
| 40 | 1965 | 245 | 1760 | 450 | 1555 | 655 | 1350 | 860 | 1145 |
| 45 | 1960 | 250 | 1755 | 455 | 1550 | 660 | 1345 | 865 | 1140 |
| 50 | 1955 | 255 | 1750 | 460 | 1545 | 665 | 1340 | 870 | 1135 |
| 55 | 1950 | 260 | 1745 | 465 | 1540 | 670 | 1335 | 875 | 1130 |
| 60 | 1945 | 265 | 1740 | 470 | 1535 | 675 | 1330 | 880 | 1125 |
| 65 | 1940 | 270 | 1735 | 475 | 1530 | 680 | 1325 | 885 | 1120 |
| 70 | 1935 | 275 | 1730 | 480 | 1525 | 685 | 1320 | 890 | 1115 |
| 75 | 1930 | 280 | 1725 | 485 | 1520 | 690 | 1315 | 895 | 1110 |
| 80 | 1925 | 285 | 1720 | 490 | 1515 | 695 | 1310 | 900 | 1105 |
| 85 | 1920 | 290 | 1715 | 495 | 1510 | 700 | 1305 | 905 | 1100 |
| 90 | 1915 | 295 | 1710 | 500 | 1505 | 705 | 1300 | 910 | 1095 |
| 95 | 1910 | 300 | 1705 | 505 | 1500 | 710 | 1295 | 915 | 1090 |
| 100 | 1905 | 305 | 1700 | 510 | 1495 | 715 | 1290 | 920 | 1085 |
| 105 | 1900 | 310 | 1695 | 515 | 1490 | 720 | 1285 | 925 | 1080 |
| 110 | 1895 | 315 | 1690 | 520 | 1485 | 725 | 1280 | 930 | 1075 |
| 115 | 1890 | 320 | 1685 | 525 | 1480 | 730 | 1275 | 935 | 1070 |
| 120 | 1885 | 325 | 1680 | 530 | 1475 | 735 | 1270 | 940 | 1065 |
| 125 | 1880 | 330 | 1675 | 535 | 1470 | 740 | 1265 | 945 | 1060 |
| 130 | 1875 | 335 | 1670 | 540 | 1465 | 745 | 1260 | 950 | 1055 |
| 135 | 1870 | 340 | 1665 | 545 | 1460 | 750 | 1255 | 955 | 1050 |
| 140 | 1865 | 345 | 1660 | 550 | 1455 | 755 | 1250 | 960 | 1045 |
| 145 | 1860 | 350 | 1655 | 555 | 1450 | 760 | 1245 | 965 | 1040 |
| 150 | 1855 | 355 | 1650 | 560 | 1445 | 765 | 1240 | 970 | 1035 |
| 155 | 1850 | 360 | 1645 | 565 | 1440 | 770 | 1235 | 975 | 1030 |
| 160 | 1845 | 365 | 1640 | 570 | 1435 | 775 | 1230 | 980 | 1025 |
| 165 | 1840 | 370 | 1635 | 575 | 1430 | 780 | 1225 | 985 | 1020 |
| 170 | 1835 | 375 | 1630 | 580 | 1425 | 785 | 1220 | 990 | 1015 |
| 175 | 1830 | 380 | 1625 | 585 | 1420 | 790 | 1215 | 995 | 1010 |
| 180 | 1825 | 385 | 1620 | 590 | 1415 | 795 | 1210 | 1000 | 1005 |
| 185 | 1820 | 390 | 1615 | 595 | 1410 | 800 | 1205 | | |
| 190 | 1815 | 395 | 1610 | 600 | 1405 | 805 | 1200 | | |
| 195 | 1810 | 400 | 1605 | 605 | 1400 | 810 | 1195 | | |

FIG. 25B

| C | |
|---|---|
| From | To |
| 2 | 1000 |
| 4 | 998 |
| 6 | 996 |
| 8 | 994 |
| 10 | 992 |
| 12 | 990 |
| 14 | 988 |
| 16 | 986 |
| 18 | 984 |
| 20 | 982 |
| 22 | 980 |
| 24 | 978 |
| 26 | 976 |
| 28 | 974 |
| 30 | 972 |
| 32 | 970 |
| 34 | 968 |
| 36 | 966 |
| 38 | 964 |
| 40 | 962 |
| 42 | 960 |
| 44 | 958 |
| 46 | 956 |
| 48 | 954 |
| 50 | 952 |
| 52 | 950 |
| 54 | 948 |
| 56 | 946 |
| 58 | 944 |
| 60 | 942 |
| 62 | 940 |
| 64 | 938 |
| 66 | 936 |
| 68 | 934 |
| 70 | 932 |
| 72 | 930 |
| 74 | 928 |
| 76 | 926 |
| 78 | 924 |
| 80 | 922 |

| From | To |
|---|---|
| 82 | 920 |
| 84 | 918 |
| 86 | 916 |
| 88 | 914 |
| 90 | 912 |
| 92 | 910 |
| 94 | 908 |
| 96 | 906 |
| 98 | 904 |
| 100 | 902 |
| 102 | 900 |
| 104 | 898 |
| 106 | 896 |
| 108 | 894 |
| 110 | 892 |
| 112 | 890 |
| 114 | 888 |
| 116 | 886 |
| 118 | 884 |
| 120 | 882 |
| 122 | 880 |
| 124 | 878 |
| 126 | 876 |
| 128 | 874 |
| 130 | 872 |
| 132 | 870 |
| 134 | 868 |
| 136 | 866 |
| 138 | 864 |
| 140 | 862 |
| 142 | 860 |
| 144 | 858 |
| 146 | 856 |
| 148 | 854 |
| 150 | 852 |
| 152 | 850 |
| 154 | 848 |
| 156 | 846 |
| 158 | 844 |
| 160 | 842 |
| 162 | 840 |
| 164 | 838 |

| From | To |
|---|---|
| 166 | 836 |
| 168 | 834 |
| 170 | 832 |
| 172 | 830 |
| 174 | 828 |
| 176 | 826 |
| 178 | 824 |
| 180 | 822 |
| 182 | 820 |
| 184 | 818 |
| 186 | 816 |
| 188 | 814 |
| 190 | 812 |
| 192 | 810 |
| 194 | 808 |
| 196 | 806 |
| 198 | 804 |
| 200 | 802 |
| 202 | 800 |
| 204 | 798 |
| 206 | 796 |
| 208 | 794 |
| 210 | 792 |
| 212 | 790 |
| 214 | 788 |
| 216 | 786 |
| 218 | 784 |
| 220 | 782 |
| 222 | 780 |
| 224 | 778 |
| 226 | 776 |
| 228 | 774 |
| 230 | 772 |
| 232 | 770 |
| 234 | 768 |
| 236 | 766 |
| 238 | 764 |
| 240 | 762 |
| 242 | 760 |
| 244 | 758 |
| 246 | 756 |
| 248 | 754 |

| From | To |
|---|---|
| 250 | 752 |
| 252 | 750 |
| 254 | 748 |
| 256 | 746 |
| 258 | 744 |
| 260 | 742 |
| 262 | 740 |
| 264 | 738 |
| 266 | 736 |
| 268 | 734 |
| 270 | 732 |
| 272 | 730 |
| 274 | 728 |
| 276 | 726 |
| 278 | 724 |
| 280 | 722 |
| 282 | 720 |
| 284 | 718 |
| 286 | 716 |
| 288 | 714 |
| 290 | 712 |
| 292 | 710 |
| 294 | 708 |
| 296 | 706 |
| 298 | 704 |
| 300 | 702 |
| 302 | 700 |
| 304 | 698 |
| 306 | 696 |
| 308 | 694 |
| 310 | 642 |
| 312 | 690 |
| 314 | 688 |
| 316 | 686 |
| 318 | 684 |
| 320 | 682 |
| 322 | 680 |
| 324 | 678 |
| 326 | 676 |
| 328 | 674 |
| 330 | 672 |
| 332 | 670 |

| From | To |
|---|---|
| 334 | 668 |
| 336 | 666 |
| 338 | 664 |
| 340 | 662 |
| 342 | 660 |
| 344 | 658 |
| 346 | 656 |
| 348 | 654 |
| 350 | 652 |
| 352 | 650 |
| 354 | 648 |
| 356 | 646 |
| 358 | 644 |
| 360 | 642 |
| 362 | 640 |
| 364 | 638 |
| 366 | 636 |
| 368 | 634 |
| 370 | 632 |
| 372 | 630 |
| 374 | 628 |
| 376 | 626 |
| 378 | 624 |
| 380 | 622 |
| 382 | 620 |
| 384 | 618 |
| 386 | 616 |
| 388 | 614 |
| 390 | 612 |
| 392 | 610 |
| 394 | 608 |
| 396 | 606 |
| 398 | 604 |
| 400 | 602 |
| 402 | 600 |
| 404 | 598 |
| 406 | 596 |
| 408 | 594 |
| 410 | 592 |
| 412 | 590 |
| 414 | 588 |
| 416 | 586 |

| From | To |
|---|---|
| 418 | 584 |
| 420 | 582 |
| 422 | 580 |
| 424 | 578 |
| 426 | 576 |
| 428 | 574 |
| 430 | 572 |
| 432 | 570 |
| 434 | 68 |
| 436 | 566 |
| 438 | 564 |
| 440 | 562 |
| 442 | 560 |
| 444 | 558 |
| 446 | 556 |
| 448 | 554 |
| 450 | 552 |
| 452 | 550 |
| 454 | 548 |
| 456 | 546 |
| 458 | 544 |
| 460 | 542 |
| 462 | 540 |
| 464 | 538 |
| 466 | 536 |
| 468 | 534 |
| 470 | 532 |
| 472 | 530 |
| 474 | 528 |
| 476 | 526 |
| 478 | 524 |
| 480 | 522 |
| 482 | 520 |
| 484 | 518 |
| 486 | 516 |
| 488 | 514 |
| 490 | 512 |
| 492 | 510 |
| 494 | 508 |
| 496 | 506 |
| 498 | 504 |
| 500 | 502 |

FIG. 25C

| D | |
|---|---|
| From | To |
| 2 | 500 |
| 4 | 498 |
| 6 | 496 |
| 8 | 494 |
| 10 | 492 |
| 12 | 490 |
| 14 | 488 |
| 16 | 486 |
| 18 | 484 |
| 20 | 482 |
| 22 | 480 |
| 24 | 478 |
| 26 | 476 |
| 28 | 474 |
| 30 | 472 |
| 32 | 470 |
| 34 | 468 |
| 36 | 466 |
| 38 | 464 |
| 40 | 462 |
| 42 | 460 |
| 44 | 458 |
| 46 | 456 |
| 48 | 454 |
| 50 | 452 |
| 52 | 450 |
| 54 | 448 |
| 56 | 446 |
| 58 | 444 |
| 60 | 442 |
| 62 | 440 |
| 64 | 438 |
| 66 | 436 |
| 68 | 434 |
| 70 | 432 |
| 72 | 430 |
| 74 | 428 |
| 76 | 426 |
| 78 | 424 |
| 80 | 422 |
| 82 | 420 |
| 84 | 418 |
| 86 | 416 |
| 88 | 414 |
| 90 | 412 |
| 92 | 410 |
| 94 | 408 |
| 96 | 406 |
| 98 | 404 |
| 100 | 402 |
| 102 | 400 |
| 104 | 398 |
| 106 | 396 |
| 108 | 394 |
| 110 | 392 |
| 112 | 390 |
| 114 | 388 |
| 116 | 386 |
| 118 | 384 |
| 120 | 382 |
| 122 | 380 |
| 124 | 378 |
| 126 | 376 |
| 128 | 374 |
| 130 | 372 |
| 132 | 370 |
| 134 | 368 |
| 136 | 366 |
| 138 | 364 |
| 140 | 362 |
| 142 | 360 |
| 144 | 358 |
| 146 | 356 |
| 148 | 354 |
| 150 | 352 |
| 152 | 350 |
| 154 | 348 |
| 156 | 346 |
| 158 | 344 |
| 160 | 342 |
| 162 | 340 |
| 164 | 338 |
| 166 | 336 |
| 168 | 334 |
| 170 | 332 |
| 172 | 330 |
| 174 | 328 |
| 176 | 326 |
| 178 | 324 |
| 180 | 322 |
| 182 | 320 |
| 184 | 318 |
| 186 | 316 |
| 188 | 314 |
| 190 | 312 |
| 192 | 310 |
| 194 | 308 |
| 196 | 306 |
| 198 | 304 |
| 200 | 302 |
| 202 | 300 |
| 204 | 298 |
| 206 | 296 |
| 208 | 294 |
| 210 | 292 |
| 212 | 290 |
| 214 | 288 |
| 216 | 286 |
| 218 | 284 |
| 220 | 282 |
| 222 | 280 |
| 224 | 278 |
| 226 | 276 |
| 228 | 274 |
| 230 | 272 |
| 232 | 270 |
| 234 | 268 |
| 236 | 266 |
| 238 | 264 |
| 240 | 262 |
| 242 | 260 |
| 244 | 258 |
| 246 | 256 |
| 248 | 254 |
| 250 | 252 |

FIG. 25D

FUNCTIONALIZED GRAPHENE OXIDE SYSTEM FOR DETECTING RARE CELLS

CROSS REFERENCE TO RELATED APPLICATIONS

The subject patent application is a continuation of U.S. patent application Ser. No. 14/347,073, filed on Mar. 25, 2014, which is the National Stage of International Patent Application No. PCT/US2012/058013, filed on Sep. 28, 2012, which claims priority to and all the advantages of U.S. Provisional Application Ser. No. 61/541,814, filed on Sep. 30, 2011. The contents of U.S. patent application Ser. No. 14/347,073, International Patent Application No. PCT/US2012/058013, and U.S. Provisional Application Ser. No. 61/541,814 are incorporated herein by reference in their entirety.

DESCRIPTION OF THE RELATED ART

As is well appreciated in the art, there are myriad technological obstacles in the identification, enumeration, detection, capture, and isolation of rare cells. These technological obstacles tend to limit the quantitative evaluation of rare cells, for example, in early diagnosis of metastatic diseases and effective monitoring of therapeutic response in patients.

Some rare cells, e.g. circulating tumor cells (CTCs) and/or viable tumor-derived epithelial cells, have been identified in peripheral blood from cancer patients and are likely the origin of intractable metastatic disease. CTCs, as just one type of rare cell, tend to be present in an amount of about 1 CTC per 1 billion blood cells and tend to circulate in peripheral blood of patients with metastatic cancer. Detection, isolation, and capture of CTCs represent a potential alternative to invasive biopsies during diagnosis of disease. More specifically, the ability to identify, isolate, propagate and molecularly characterize CTC subpopulations could further the discovery of cancer stem cell biomarkers, expand the understanding of the biology of metastasis, and improve the therapeutic treatment of cancer patients and the ultimate treatment outcome. Many current strategies for isolating CTCs are limited to complex analytic approaches that are typically very low yield and low purity and that could be improved relative to sensitivity and accuracy.

Many existing technologies utilize devices through which blood flows over and around large three-dimensional structures for capturing CTCs. These structures tend to be expensive to produce, tend to act as obstacles to the flow of blood thereby decreasing the efficiency of the devices, and tend to lack sensitivity for the CTCs thereby causing the device to have a low cell capture efficiency. Accordingly, there remains an opportunity to develop an improved system and method of detecting rare cells.

SUMMARY OF THE DISCLOSURE

One embodiment of the instant disclosure provides a system for detecting rare cells. The system includes a substrate, an extension coupled to the substrate and extending outwardly from the substrate, and a functionalized graphene oxide disposed on the extension. This disclosure also provides a method for detecting rare cells using the system of this disclosure. The method includes the steps of providing the system and introducing a sample of bodily fluid to the system such that the sample interacts with the functionalized graphene oxide.

BRIEF DESCRIPTION OF THE DRAWINGS

Other advantages of the present disclosure will be readily appreciated, as the present disclosure becomes better understood by reference to the following detailed description when considered in connection with the accompanying drawings.

FIG. 25A is a table that sets forth optional non-limiting values of (A) of various embodiments of the leaf pattern set forth in FIG. 4A.

FIG. 25B is a table that sets forth optional non-limiting values of (B) of various embodiments of the leaf pattern set forth in FIG. 4A.

FIG. 25C is a table that sets forth optional non-limiting values of (C) of various embodiments of the leaf pattern set forth in FIG. 4A.

FIG. 25D is a table that sets forth optional non-limiting values of (D) of various embodiments of the leaf pattern set forth in FIG. 4A.

DETAILED DESCRIPTION OF THE DISCLOSURE

The present disclosure provides a system (20) for detecting rare cells (22). Most typically, the rare cells (22) are present in samples of blood, e.g. anticoagulated whole blood. However, it is also contemplated that the rare cells (22) may be present in samples of other bodily fluids that may be, include, consist essentially of, or consist of, but are not limited to, saliva, mucus, excretions, and the like. The terminology "consist essentially of" describes an embodiment wherein the bodily fluid is not diluted with a diluent. In one embodiment, the rare cells (22) may be transmitted via breath, i.e., breathing, sneezing, coughing, and the like, such that the rare cells (2) may be, at least for a time, airborne and thus still be present in a bodily fluid for purposes of this disclosure. The bodily fluid may be utilized without pre-dilution, pre-labeling, pre-fixation, centrifugation, lysis, or any other processing steps.

Transporting fluids, such as buffers, which may be miscible or immiscible with various samples of blood and/or bodily fluids, may also be employed. In various embodiments, samples of blood, bodily fluids, and the like, may be evaluated in volumes of about 50 µL to about 5 mL, about 100 µL to about 1 mL, or about 250 µL to about 550 µL. However, the present disclosure is not limited to these volumes or to dilution of bodily fluids. In one embodiment, about 1 mL of sample is utilized. In other embodiments, 1 to 20, 2 to 19, 3 to 18, 4 to 17, 5 to 16, 6 to 15, 7 to 14, 8 to 13, 9 to 12, or 10 to 11, mL of sample are utilized. Any of the aforementioned values may, for example, vary by 1, 2, 3, 4, 5, 10, 15, 20, or 25+% in varying non-limiting embodiments. All values, and ranges of values, between and including the aforementioned values are also hereby expressly contemplated in various non-limiting embodiments.

Figure 17A:
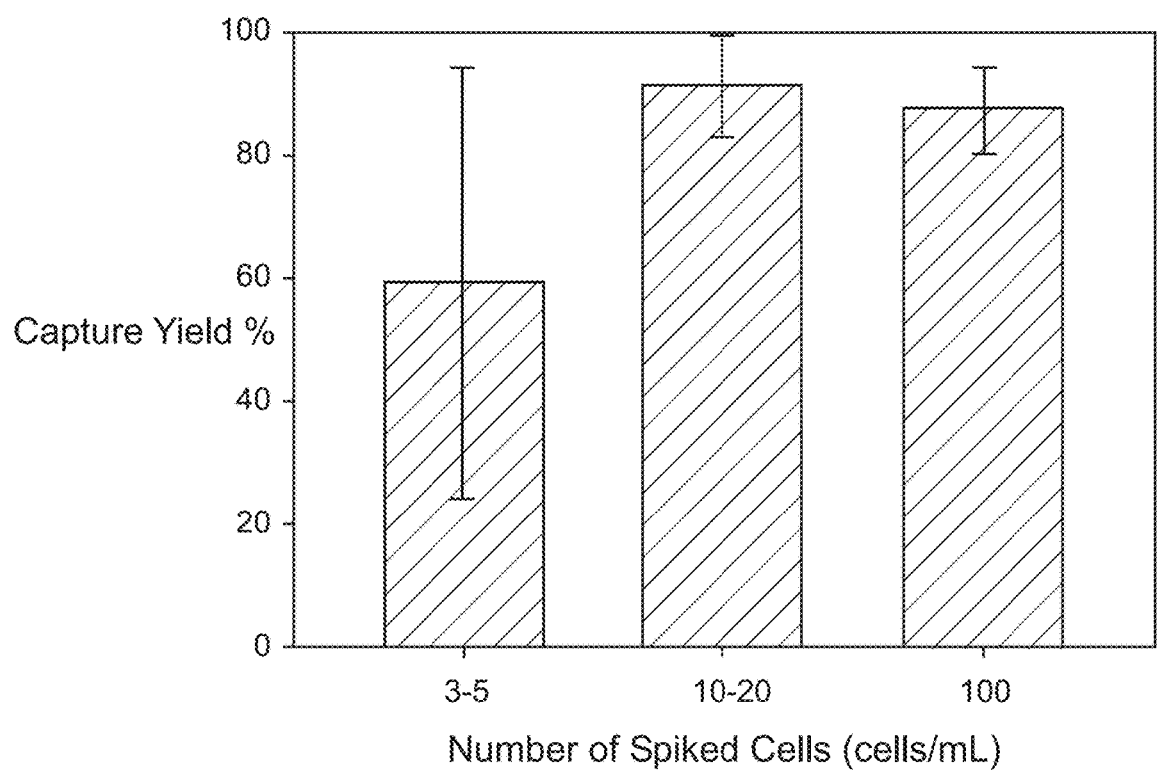
FIG. 17A is a bar graph showing the capture efficiency of various examples utilizing a microfluidic device similar to that illustrated in FIG. 2G and varying amounts of MCF-cells (3-5 cells, 10-20 cells, 100 cells) spiked into 1 mL of whole blood.
Figure 17B:
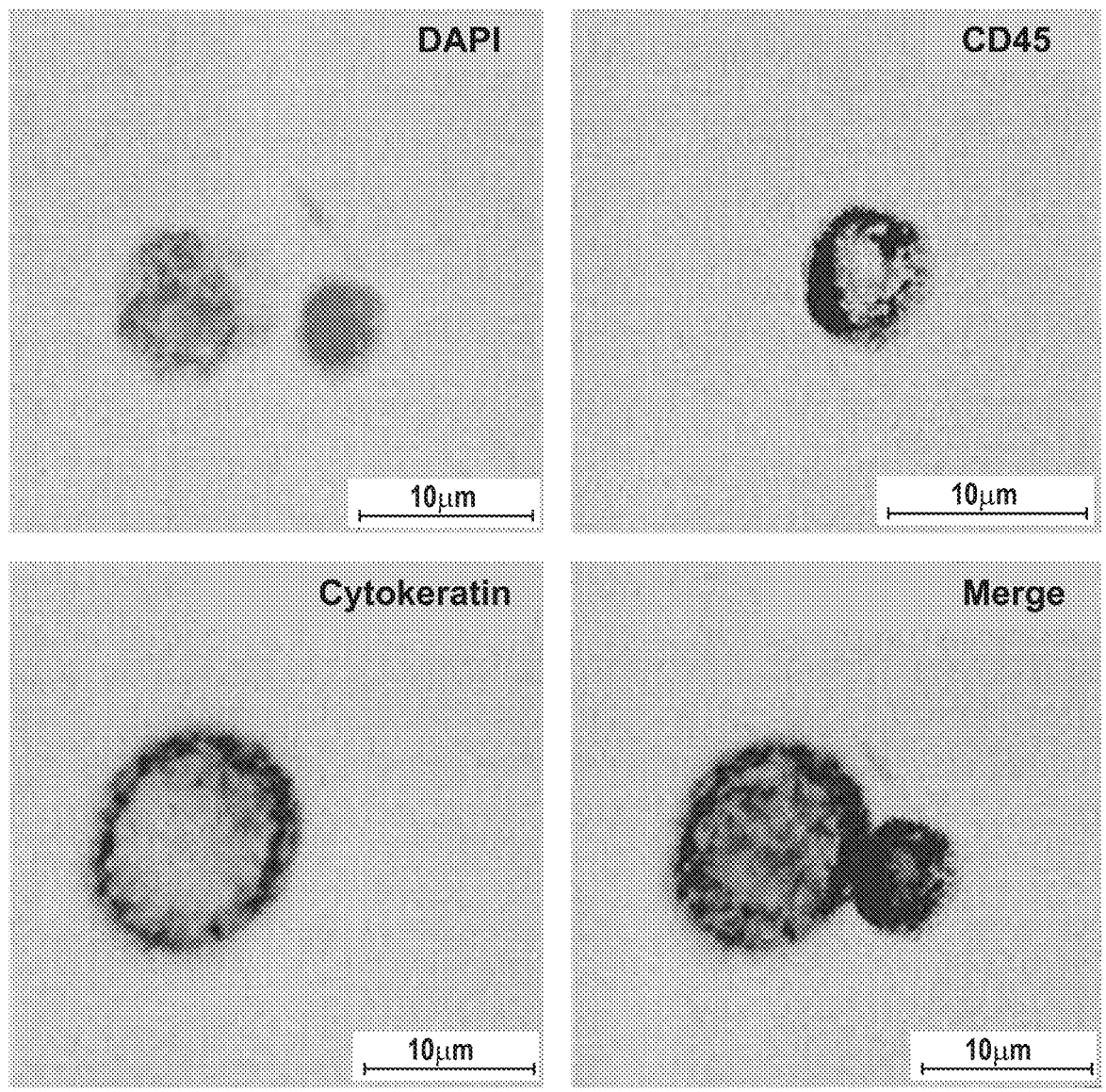
FIG. 17B is a series of fluorescence microscope images of MCF-7 cell and white blood cell stained with DAPI, Cytokeratin, and CD45. The merged image identifies CTCs/cancer cells. CTCs/cancer cells are positive for DAPI and Cytokeratin. White blood cells are positive for DAPI and CD45.
Figure 17C:
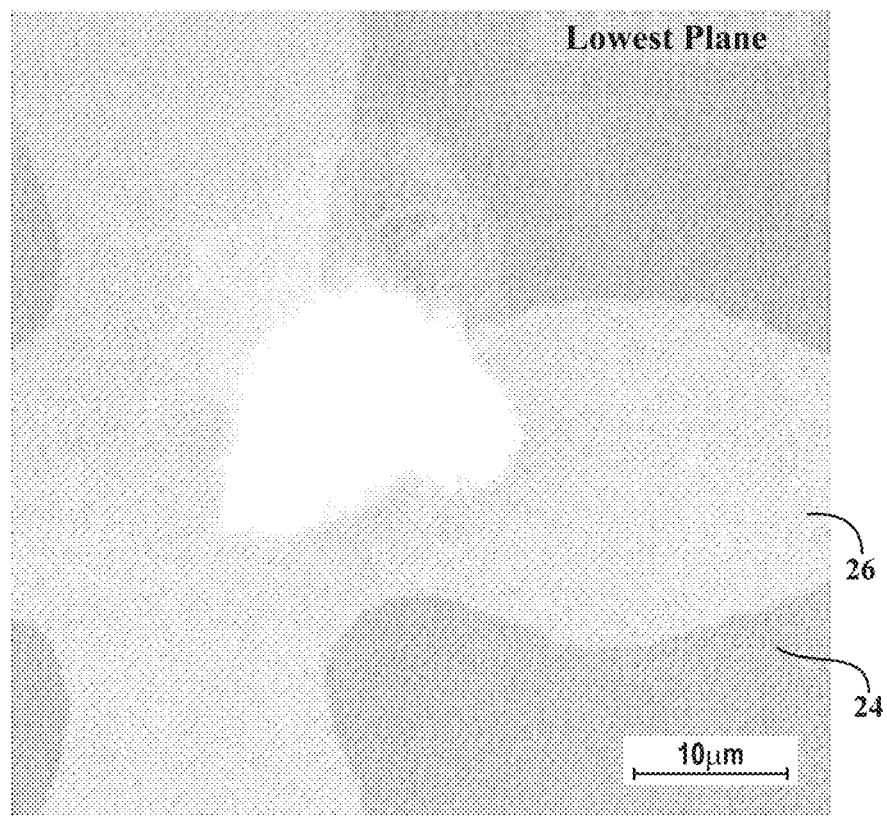
FIG. 17C is a magnified fluorescence microscope images of MCF-7 cell and white blood cell bound to a plurality of extensions disposed in a leaf pattern.
Figure 17D:
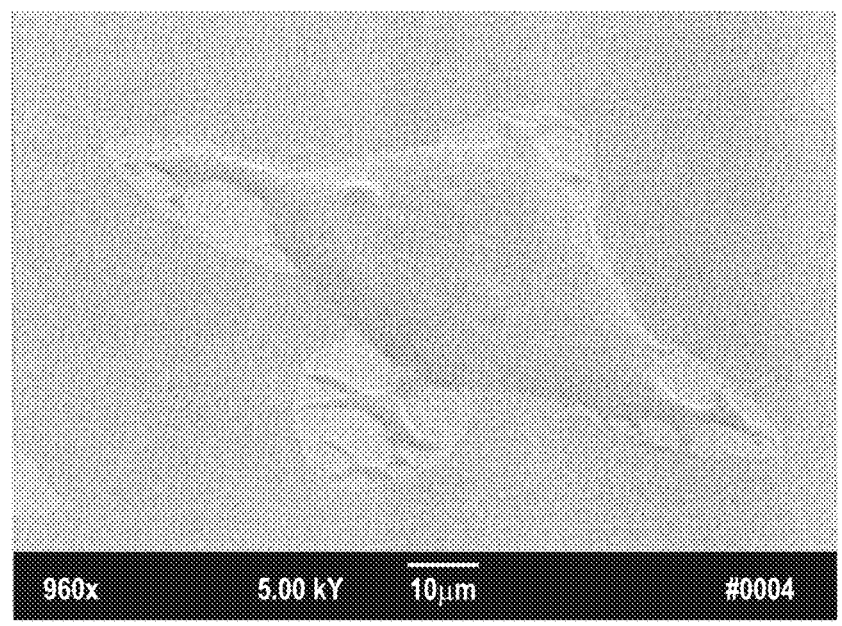
FIG. 17D is an SEM image of a cluster of rare cells proliferating while bound to a plurality of extensions.

The particular type of rare cells (22) contemplated in this disclosure is not limited. In one embodiment, the rare cells (22) are further defined as circulating tumor cells (22) (CTCs), see e.g. FIG. 17B. In other embodiments, the rare cells are chosen from the group of endothelial cells, fetal cells, and/or cells of hemopoietic origin (e.g. platelets, sickle cell red blood cells, and subpopulations of leukocytes). In still other embodiments, the terminology "rare cells" alternatively describes exosomes, microvessicles, bacteria, viruses, protists, and/or fungi.

The rare cells, such as CTCs, may be present, for example in blood, bodily fluids, and the like, in any amount, e.g. in amounts of from 0.01 to 10, from 0.1 to 10, from 1 to 10, from 1 to 20, from 1 to 30, from 1 to 40, from 1 to 50, from 1 to 60, from 1 to 70, from 1 to 80, from 1 to 90, from 1 to 100, from 100 to 1000, from 200 to 900, from 300 to 800, from 400 to 700, from 500 to 600, from 1 to 5, or 0.1, 0.2, 0.3, 0.4, 0.5, 0,6, 0.7, 0.8, 0.9, 1, 2, 3, 4, 5, 6, 7, 8, 9, or 10, rare cells per one billion total blood cells. Alternatively, the rare cells may be present in amounts of greater than 0.01, 0.1, 1, 10, 50, 100, 500, 1000, 5000, or 10000, rare cells per one billion total blood cells. Any of the aforementioned values may, for example, vary by 1, 2, 3, 4, 5, 10, 15, 20, or 25+% in varying non-limiting embodiments. All values, and ranges of values, between and including the aforementioned values are also hereby expressly contemplated in various non-limiting embodiments. Rare cells present in bodily fluids other than blood and/or CTCs may also be present in the aforementioned amounts. However, the instant disclosure is not limited to these amounts of rare cells present in bodily fluids and it is contemplated that higher or lower amounts may also be utilized.

The system of this disclosure includes a substrate (24), an extension (26) coupled to the substrate (24) and extending outwardly from the substrate (24) and a functionalized graphene oxide (28) disposed on the extension (26). Various embodiments of the system are set forth in FIGS. 1A-D. Typically, as a bodily fluid flows over the substrate, e.g. through a microfluidic channel (32) and/or a microfluidic chamber (56), rare cells in the bodily fluid come into contact with the functionalized graphene oxide, one or more binding agents, markers, proteins, etc. and become immobilized, e.g. on the surface of the extension (26) or as attached to one or more binding agents, markers, proteins, etc. Each of the substrate (24), the extension (26), and the functionalized graphene oxide (28) is described in greater detail below.

Substrate:

The substrate (24) is not particularly limited in this disclosure and may be further defined as being, including, consisting essentially of, or consisting of, a metal, plastic, polymer, inorganic compound, glass, silicon (e.g. —Si—Si—), silicone (e.g. —Si—O—Si— or PDMS), epoxy, semiconductors, and/or combinations thereof. The terminology "consist essentially of" typically describes that the substrate (24) includes one or more of the particular aforementioned materials and is free of, or includes less than 0.1 or 1, weight percent, of dissimilar materials. The substrate (24) may be fabricated using any technique known in the art including, but not limited to, molding, photolithography, electroforming, machining, chemical vapor deposition, and the like.

The substrate (24) may also be further defined as a device, layer, film, coating, sheet, skin, chip, block, or wafer. In various embodiments, the substrate (24) is further defined as a tri-layered substrate that includes a silicon layer, an $SiO_2$ layer, and a PDMS (i.e., polydimethylsiloxane) layer, as set forth in FIG. 1A. Alternatively, the substrate (24) may be further defined as a single layer. In one embodiment, additional layers, e.g. the $SiO_2$ layer and the PDMS layer, are disposed on the single layer and may be individually described as one or more supplemental (or support) layers (34). Depending on overall design and shape, one or more of the substrate (24) and/or one or more supplemental layers (34) may be independently further defined as an outermost layer, an innermost layer, or an interior layer, e.g. of a device or of the system (20). In other embodiments, the substrate (24) and/or one or more supplemental layer (34) may be, include, consist essentially of, or consist of, one or more of polyethylene terephthalate (PET), polyimide, polyether ether ketone (PEEK), and/or combinations thereof.

The substrate (24) and/or the one or more supplemental layers (34) may be bonded together by any means known in the art including use of adhesives, chemical bonding techniques, and physical bonding techniques. In one embodiment, the substrate (24) includes an $SiO_2$ layer that is bonded to the substrate (24) using oxygen plasma treatment.

The substrate (24) and one or more supplemental layers (34) are not limited to any particular configuration or structure and each of the substrate (24) and one or more supplemental layers (34) may independently be disposed in any order or configuration relative to one another. All combinations of these layers and configurations are herein expressly contemplated. Each of the substrate (24) and supplemental layers (34) are also not particularly limited to any particular cross-section and each may independently have, but is not limited to having, a rectangular cross-section, a square cross-section, a triangular cross-section, a circular or oval cross-section, an "I"-shaped cross-section, a "C"-shaped cross-section, an "L"-shaped cross-section, a "T"-shaped cross-section, a "U"-shaped cross-section, or a "W" shaped cross-section. The substrate (24) and supplemental layers (34) may be solid, hollow, or have solid sections and hollow sections.

The overall size of each of the substrate (24) and supplemental layers (34) is not particularly limited. In one embodiment, the substrate (24) has dimensions of about 35 mm×10mm×3 mm. However, these dimensions are not limiting and may vary. Suitable non-limiting examples of substrates (24) and supplemental layers (34) have length, width, and height dimensions on the scale of 1 to 100, 1 to 75, 1 to 50, 1 to 25, 1 to 20, 1 to 15, 1 to 10, 1 to 5, or 0.1 to 1, inches, centimeters, and/or millimeters. Any of the aforementioned values may, for example, vary by 1, 2, 3, 4, 5, 10, 15, 20, or 25+% in varying non-limiting embodiments. All values, and ranges of values, between and including the aforementioned values are also hereby expressly contemplated in various non-limiting embodiments. It is also contemplated that a microfluidic device, as described in greater detail below, may have the same or different dimensions from one or more of the substrate (24) and/or the supplemental layer(s) (34).

Extension:

The system also includes the extension (26) coupled to the substrate (24), and extending outwardly from the substrate (24), as set forth in FIGS. 1-4. The terminology "extension" may describe a single extension, two extensions, or a plurality of extensions, in various embodiments, throughout. Said differently, whenever the terminology "extension" is used, that terminology may describe various embodiments including a single extension, two extensions, or a plurality of extensions.

The extension (26) may extend outwardly from the substrate (24) approximately perpendicularly to a longitudinal axis ($L_1$) or may extend outwardly at another angle to the substrate (24) and/or the longitudinal axis ($L_1$), e.g. at an obtuse or acute angle, such as 30°, 45°, or 60°. The extension (26) may be coupled to the substrate (24) via any means known in the art such as through chemical and physical connections, e.g. with adhesives, via chemical bonding, and the like. Similarly, the extension (26) may be coupled to the substrate (24) in direct contact with the substrate (24) or in indirect contact with the substrate (24), e.g. separated by one or more layers, compounds, molecules, etc. As an additional example, the extension (26) may be disposed in direct contact with an intermediate or supplemental layer (34) or connection which, in turn, may be disposed either directly or indirectly with the substrate (24). It is contemplated that the extension (26) may still be coupled to the substrate (24) even though there is no direct contact therebetween.

Figure 1A:
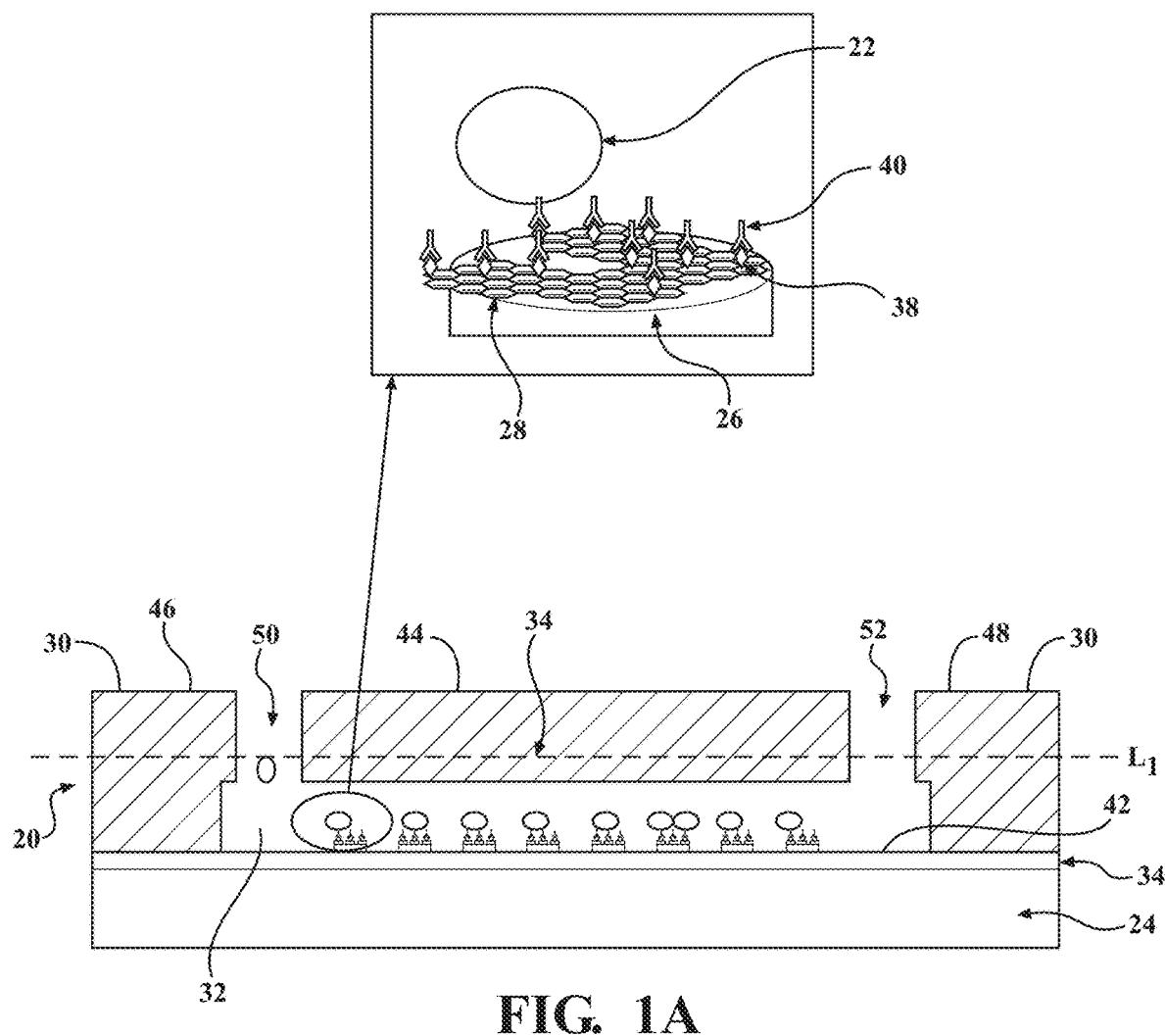
FIG. 1A is a side view of a non-limiting embodiment of a microfluidic device and includes an inset magnified view of an extension (e.g. a gold nanopost), functionalized graphene oxide disposed on the extension. NeutrAvidin bound to the functionalized graphene oxide, a cancer cell antibody bound to the NeutrAvidin, and a cancer cell bound to the antibody.
Figure 1B:
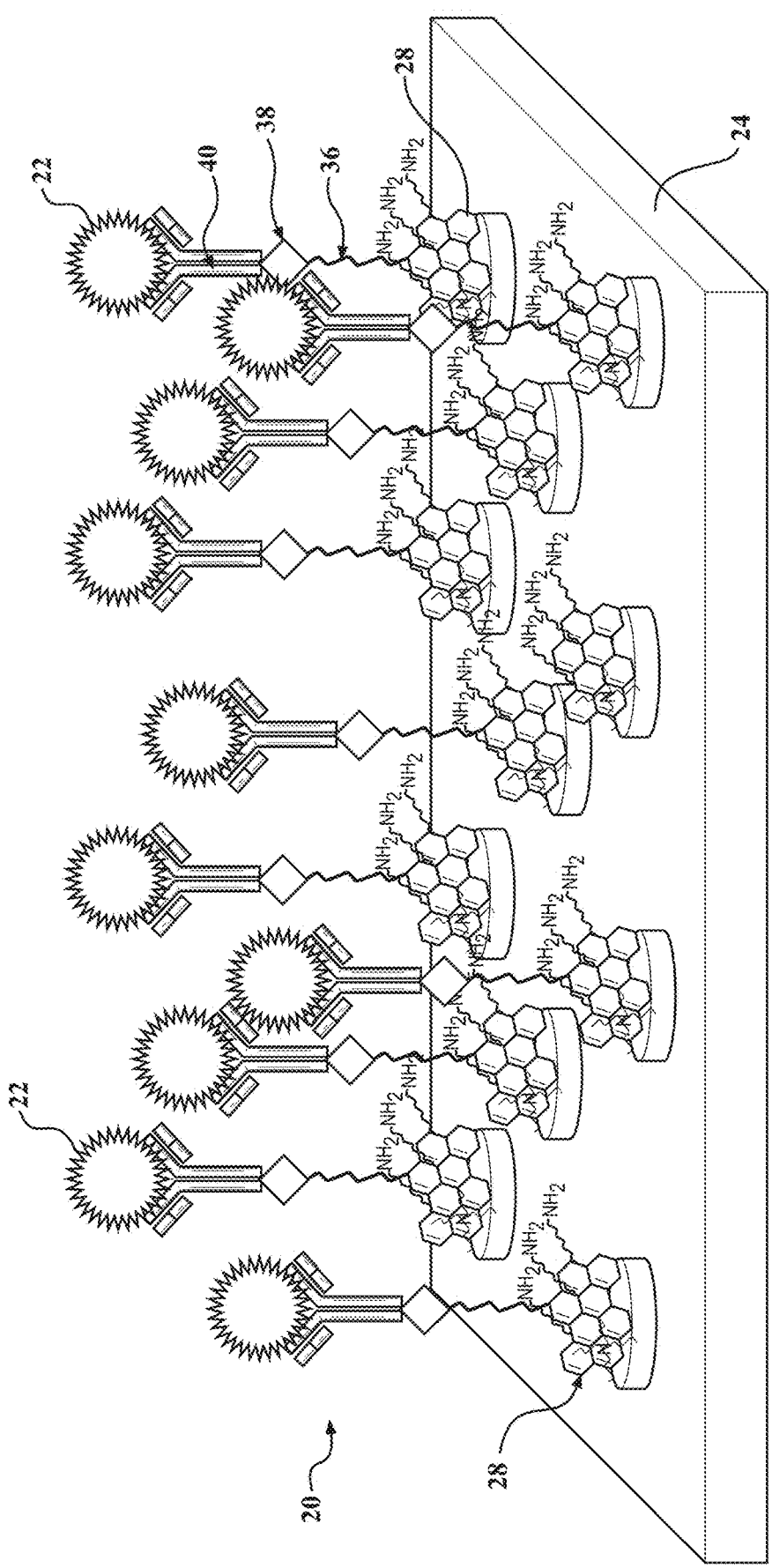
FIG. 1B is a side view of a second non-limiting embodiment of a microfluidic device including a silicon substrate, a plurality of extensions (e.g. gold nanoposts) disposed on the silicon substrate, functionalized graphene oxide disposed on the plurality of extensions, a GMBS linker bound to the functionalized graphene oxide, NeutrAvidin bound to the GMBS linker, biotinylated EpCAM antibodies bound to the GMBS linker, and cancer cells bound to the antibodies.
Figure 1C:
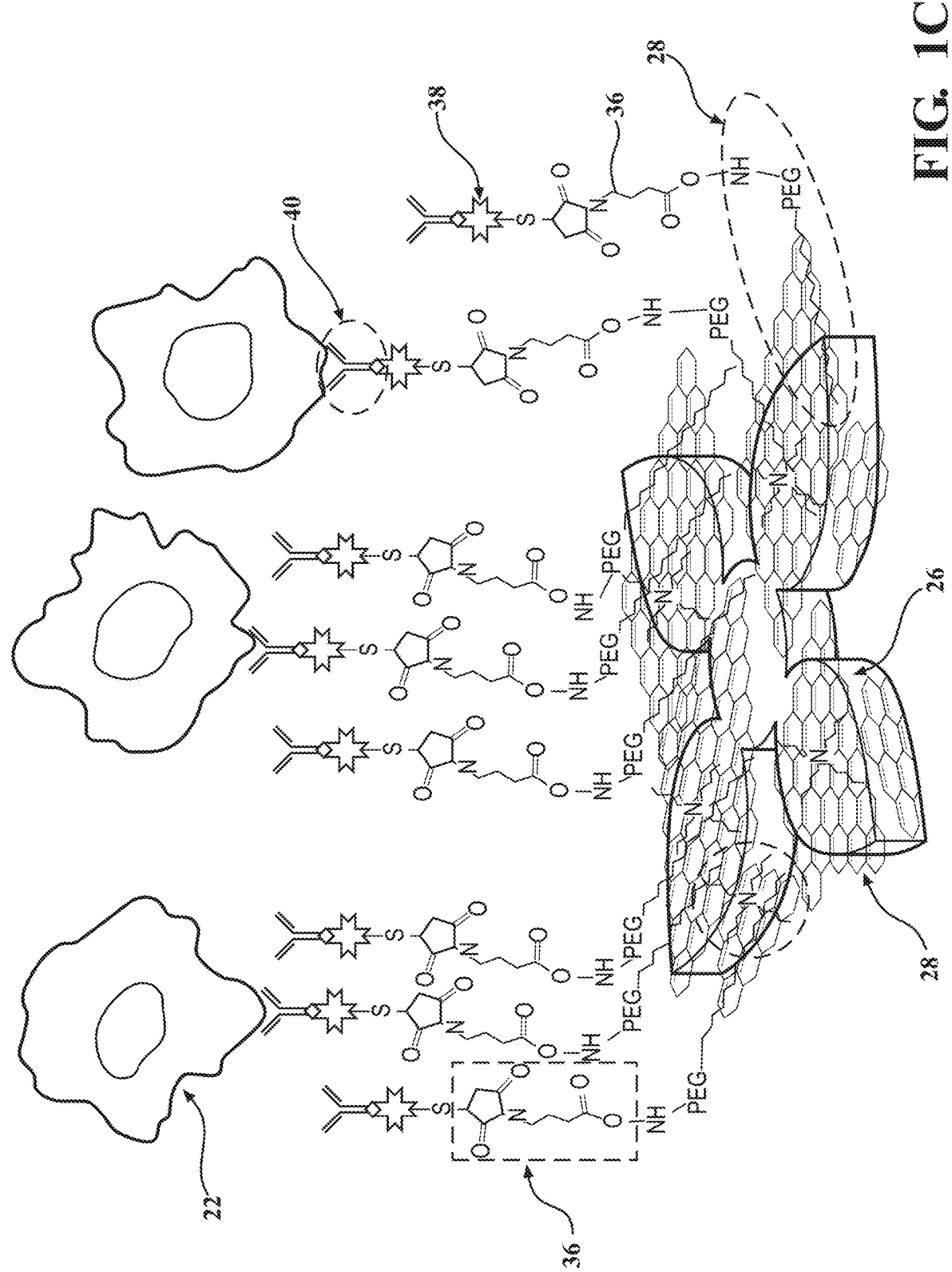
FIG. 1C is an illustration of functionalized graphene oxide disposed on a plurality of extensions distributed in a leaf pattern on a substrate.
Figure 1D:
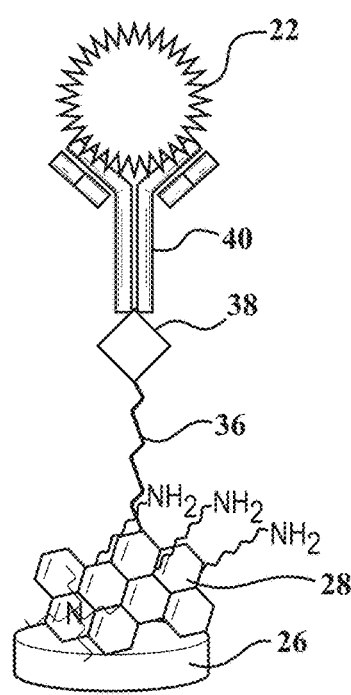
FIG. 1D is a magnified view of an extension (e.g. a gold nanopost) of FIG. 1B including the functionalized graphene oxide disposed on the gold nanopost, the GMBS linker bound to the graphene oxide, the NeutrAvidin bound to the GMBS linker, the biotinylated EpCAM antibody hound to the NeutrAvidin, and the cancer cell bound to the biotinylated EpCAM antibody.
Figure 1E:
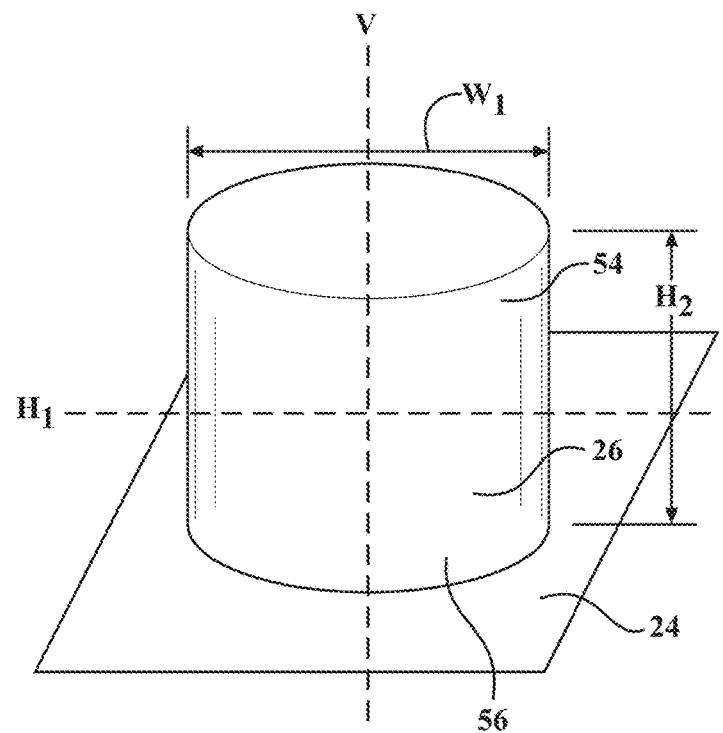
FIG. 1E is a perspective view of an extension disposed on a substrate.

The extension (26) typically has an upper end (54) and a lower end (56) and a vertical axis (V) that extends through the upper and lower ends (54, 56), as shown in FIG. 1E. Typically, the upper and lower ends (54, 56) extend along the vertical axis (V). The extension (26) also typically has a horizontal axis ($H_1$) that extends between the upper and lower ends (54, 56), as also shown in FIG. 1E.

The extension (26) may be disposed substantially perpendicularly to the substrate (24) and/or horizontal axis ($H_1$) or disposed transversely (i.e., at any angle) to the substrate (24) and/or horizontal axis ($H_1$). It is also contemplated that the extension (26) may be disposed such that the horizontal axis ($H_1$) is disposed approximately parallel to, or transverse to, the substrate (24). The extension (26) may be further defined as a post or rod, e.g. a micro-post, micro-rod, nanopost, nanorod, etc. In one embodiment, the extension (26) is further defined as an electrode, Typically, the extension (26) has micro- or nano-scale dimensions.

In various embodiments, the extension (26), e.g. a nanopost, has a height (e.g. $H_2$) of about 100 nm and a width or radius of about 10 μm. In other embodiments, the extension

(26) has a height ($H_2$) of about 10, 15, 20, 25, 30, 35, 40, 45, 50, 55, 60, 65, 70, 75, 80, 85, 90, or 95 nm, or ranges thereof. In still other embodiments, the extension (26) has a height (e.g. $H_2$) of about 105, 110, 115, 120, 125, 130, 135, 140, 145, 150, 155, 160, 165, 170, 175, 180, 185, 190, 200, 205, 210, 215, 220, 225, 230, 235, 240, 245, 250, 255, 260, 265, 270, 275, 280, 285, 290, 295, 300, 325, 350, 375, 400, 425, 450, 475, or 500 nm, or ranges thereof. In even further embodiments, the extension (26) has a height (e.g. $H_2$) of from 10 to 2000, from 50 to 2000, from 100 to 2000, from 200 to 1900, from 300 to 1800, from 400 to 1700, from 500 to 1600, from 600 to 1500, from 700 to 1400, from 800 to 1300, from 900 to 1200, or from 1000 to 1100, nm, or ranges thereof. In other embodiments, the extension (26) has a diameter or width (e.g. $W_2$) of from 100 nm to 1000 micrometers or from 100 nm to 1000 nm, from 150 to 950, from 200 to 800, from 250 to 750, from 300 to 700, from 350 to 650, from 400 to 600, from 450 to 550, or from 500 to 550, nm, or ranges thereof. In still other embodiments, the extension (26) has a diameter or width (e.g. $W_2$) of from 20 to 100, from 25 to 95, from 30 to 90, from 35 to 85, from 40 to 80, from 45 to 75, from 50 to 70, from 55 to 65, or from 60 to 65, nm, or ranges thereof. Any of the aforementioned values may, for example, vary by 1, 2, 3, 4, 5, 10, 15, 20, or 25+% in varying non-limiting embodiments. All values, and ranges of values, between and including the aforementioned values are also hereby expressly contemplated in various non-limiting embodiments.

Figure 2A:
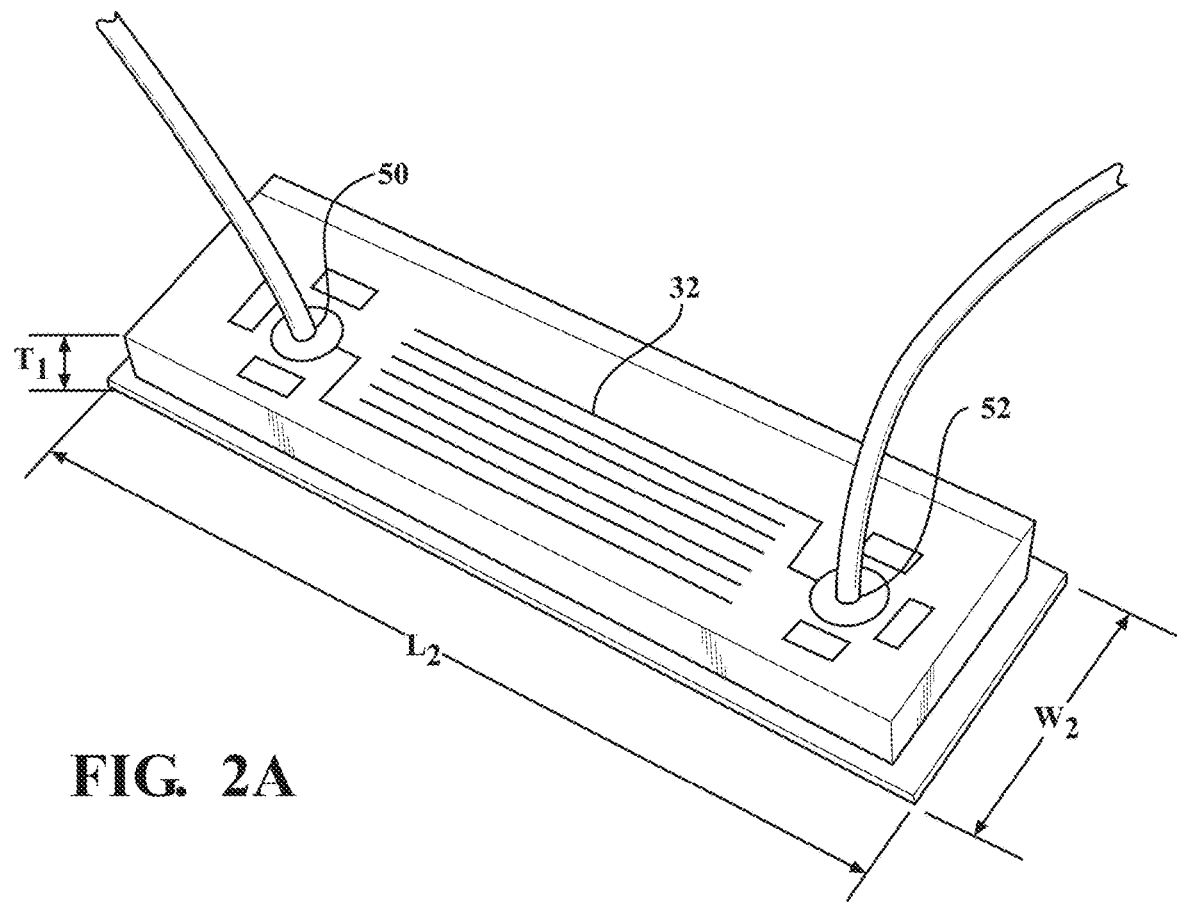
FIG. 2A is a perspective view of one embodiment of a microfluidic device.
Figure 2B:
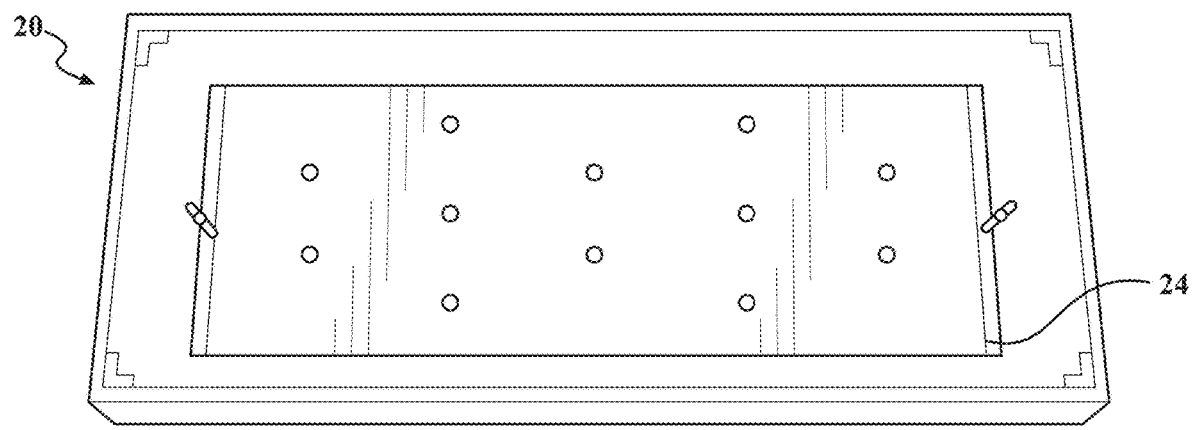
FIG. 2B is a perspective view of another embodiment of a microfluidic device that includes a pattern of gold nanoposts having a diameter of about 20 μm.
Figure 2C:
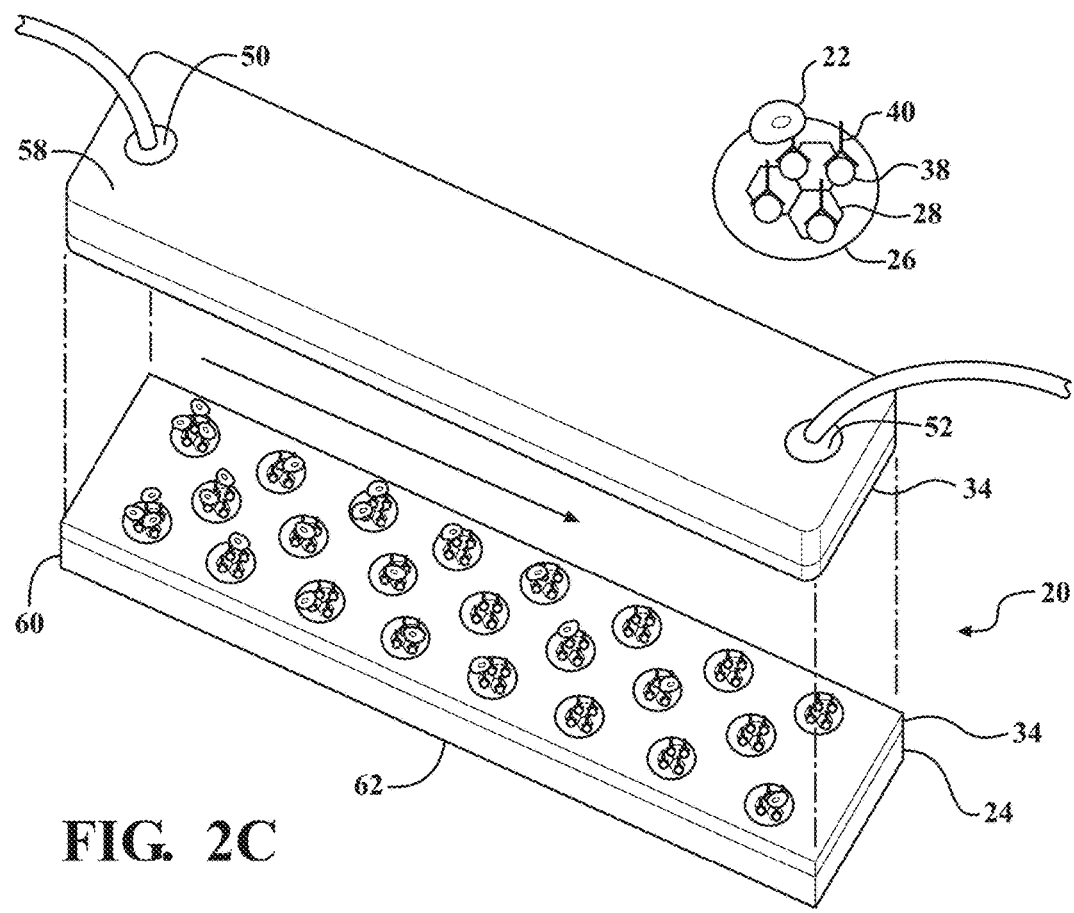
FIG. 2C is a schematic of a third embodiment of a microfluidic device and includes an inset magnified view of an extension (e.g. a gold nanopost) including the functionalized graphene oxide disposed on the extension, NeutrAvidin bound to the functionalized graphene oxide, an antibody bound to the NeutrAvidin, and a tumor cell bound to the antibody.
Figure 2D:
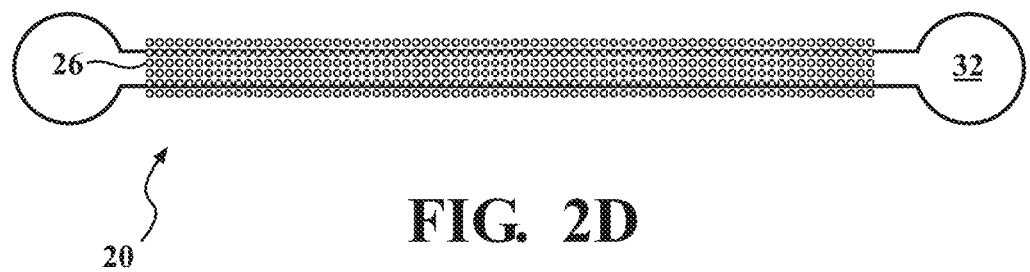
FIG. 2D is a top view of another embodiment of the microfluidic device including a microfluidic channel and a plurality of extensions disposed within the microfluidic channel.
Figure 2E:
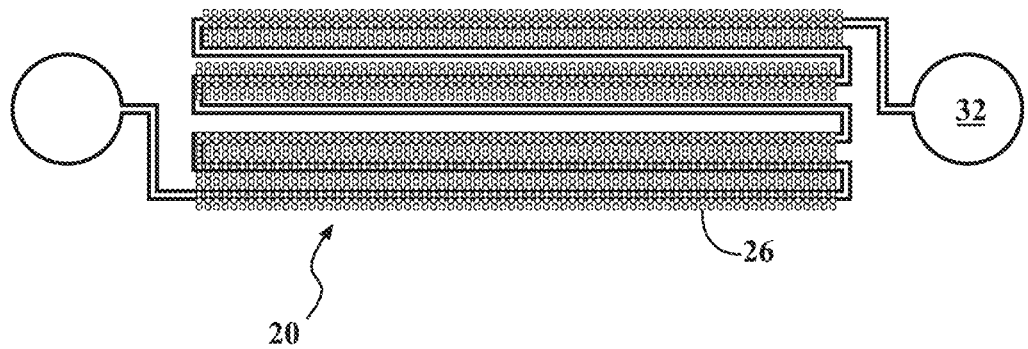
FIG. 2E is a top view of yet another embodiment of a microfluidic device including a microfluidic channel and a plurality of extensions disposed within the microfluidic channel.
Figure 2F:
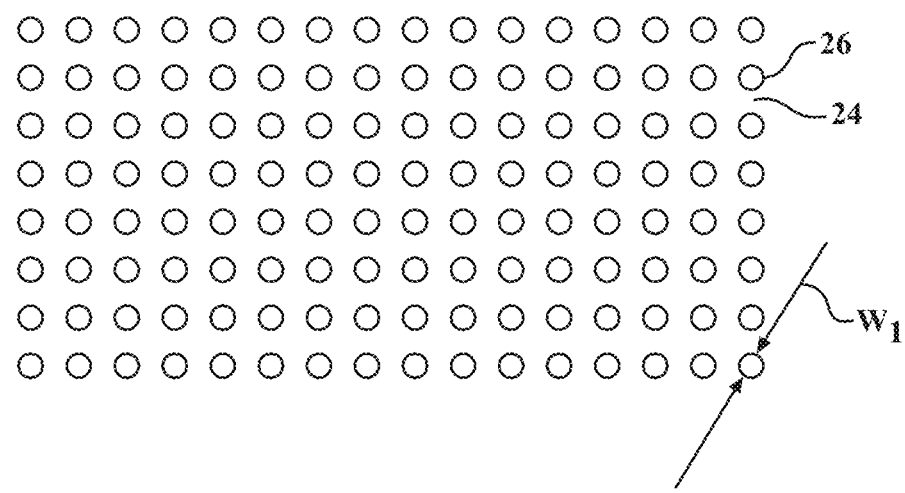
FIG. 2F is a magnified view of one embodiment of a pattern of a plurality of extensions, e.g. the extensions of FIGS. 2D and/or 2E, disposed on a substrate and illustrates a width ($W_1$) of an extension.

It is contemplated that, relative to the height/thickness of a microfluidic device or channel (32) or chamber (56), described in greater detail below, and e.g. as shown as $T_1$ in FIG. 2A or $T_2$ or $T_3$ in FIG. 2G, the extension (26) may appear essentially two dimensional, as could be determined by one of skill in the art. For example, if the height/thickness of a microfluidic device or channel (32) or chamber (56) is 40-50 micrometers, even a 500 nanometer height of an extension (26) is only 1% of the height/thickness of the microfluidic device or channel (32) or chamber (56). In a similar scenario, a 5 nanometer height of an extension (26) is only 0.01% of the height/thickness of a microfluidic device, channel (32), or chamber (56). Moreover, a 1 nanometer height of an extension (26) is only 0.002% of the height/thickness of a microfluidic device, channel (32), or chamber (56). In similar embodiments, the height of the extension (26) is small, as appreciated by a person of skill in the art, compared to the height/thickness of the microfluidic device, channel (32), or chamber (56), that the extension (26) appears to be almost two-dimensional. Similarly, even under light microscopy and modest magnification (e.g. 50-500×), the height of the extension (26) may appear essentially two-dimensional when compared to the height/thickness of the microfluidic device, channel (32), or chamber (56), as appreciated by a person of skill in the art.

The extension (26) may be, include, consist essentially of, or consist of, a plastic, polymer (such as polymethylmethacrylate (PMMA)) or metal or combinations thereof. In one embodiment, the metal is gold (e.g. the extension (26) may be formed from gold). Alternatively, the metal may be, include, consist essentially of, consist of, or be chosen from the group of, transition metals, precious metals, rare earth metals, and combinations thereof. In various embodiments, it is contemplated that the extension (26) be, include, consist of, or consist essentially of, a metal, such as gold, silver, and/or copper, and/or a mixed metal compound such as indium-tin oxide (ITO). The terminology "consist essentially of" typically describes that the extension (26) includes one or more of the aforementioned materials and is free of, or includes less than 0.1 or 1, weight percent, of a non-metal or a non-mixed metal compound or another of the aforementioned materials.

The extension (26) may be formed by any method known in the art. In one embodiment, the extension (26) is formed by evaporating and patterning metal layers, e.g. Cr/Au layers (10/100 nm). In various embodiments, the extension (26) can be formed using a lift-off process which typically allows for fine patterns to be formed. A photoresist may be coated on a silicon substrate (24) and patterned by photolithography, see e.g. FIG. 5. Then metal layers may be deposited on the silicon wafer. Subsequently, the substrate (24) may be immersed in acetone or a photoresist remover solution. A patterned gold layer typically remains. In other embodiments, a shadow mask can be used in conjunction with depositing a layer, e.g. a gold layer. Electroplating techniques may also be utilized throughout this disclosure.

The extension (26) may be disposed on any one or more portions or segments of the substrate (24), microfluidic device, channel (32), and/or chamber (56). In various embodiments, the extension (26) is disposed on or in/within a microfluidic channel (32) or a microfluidic chamber (56), as first introduced above. In other embodiments, more than one extension (26) is disposed on or in the substrate (24), microfluidic device, channel (32), and/or chamber (56) in a pattern, for example, as set forth in FIGS. 2F, 3, and 11C. It is contemplated that a total number of extensions (26) may exceed hundreds, thousands, hundreds of thousands, millions, tens of millions, etc.

The total number of extensions (26) is not particularly limited. The extension (26) itself may be formed in a shape/pattern and/or a plurality of extensions (26) may be, as a whole, set forth in a shape/pattern that may be the same or different than the pattern of any individual extension (26). Each individual extension (26) may have a shape/pattern that is the same or different from any one or more other extensions (26). Similarly, the plurality of extensions may be segmented into one or more segments and each segment may individually have a shape/pattern than is the same or different from the shape/pattern of any other segment and/or from any shape/pattern of any individual extension (26).

The size and geometry of these patterns is also not particularly limited. In one embodiment, the diameter of a pattern for an individual extension (26) is about 20 micrometers. In another embodiment, the unit length of a pattern for an individual extension (26) is about 100 micrometers. As set forth in FIGS. 4A-4C, individual extensions (26) may have a circular, flower, or leaf shape/patterns However, these shapes and patterns are not particularly limiting. Any of the aforementioned shapes/patterns are not limited and each may individually be further defined as a geometric shape/pattern, a non-geometric shape/pattern, a uniform or non-uniform shape/pattern, or as a gradient shape/pattern. Alternatively, the aforementioned shape/pattern of any one or more independent extensions (26), segments, or plurality of extensions (26) may not have any defined shape or pattern and may be described as random or amorphous. Still further, any of the aforementioned shapes/patterns may be as described below relative to the shapes/patterns of the microfluidic channel (32) and/or microfluidic chamber (56).

Figures 4A, 4B:
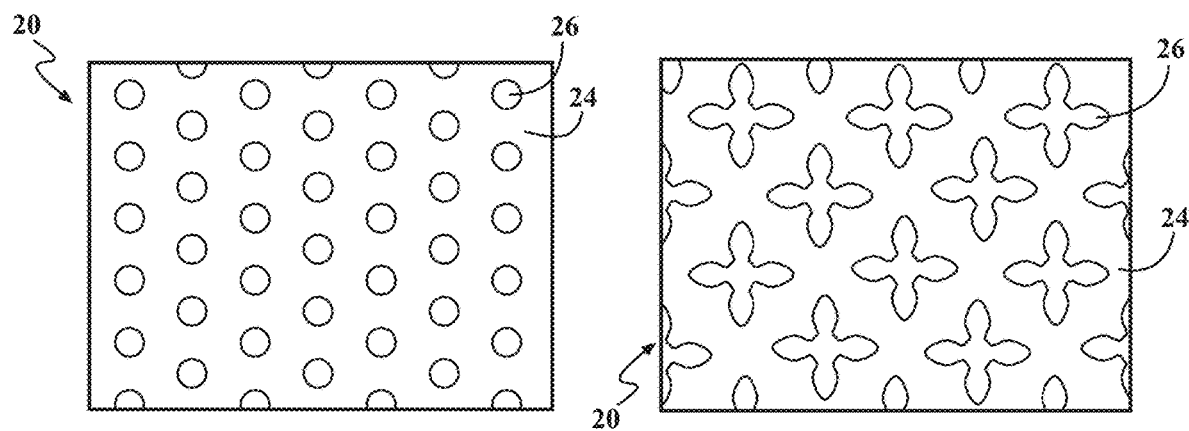
FIG. 4A is a photograph of a circular pattern of extensions (e.g. gold nanoposts) of one embodiment wherein the extensions are disposed on a substrate and wherein each extension has a diameter (e.g. $W_1$) of about 20 μm.
FIG. 4B is a photograph of a flower pattern of extensions (e.g. gold nanoposts) of one embodiment wherein the extensions are disposed on a substrate and wherein the unit length is about 100 μm.
Figure 4C:
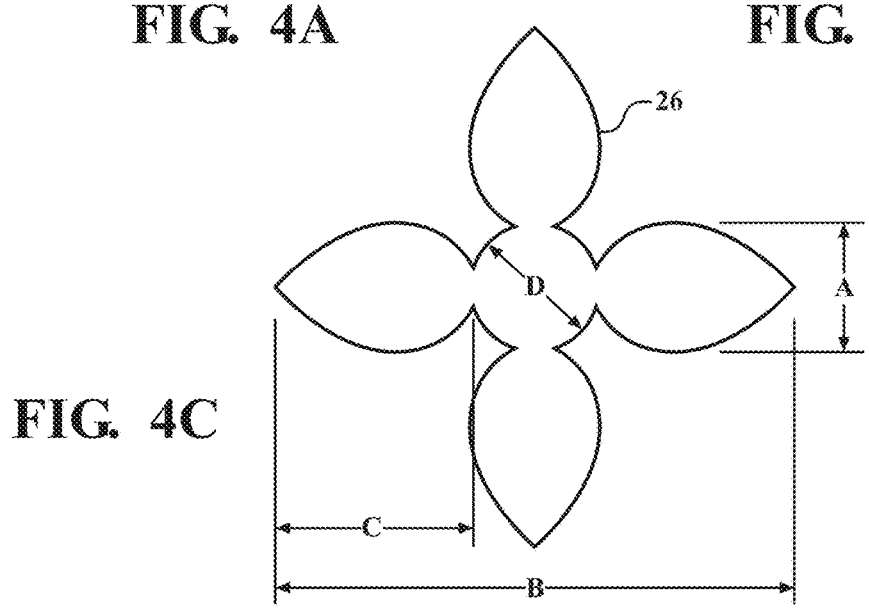
FIG. 4C is a schematic of an extension (e.g. a gold nanopost) of one embodiment wherein the extension is disposed on a substrate in a leaf pattern.
Figure 4D:
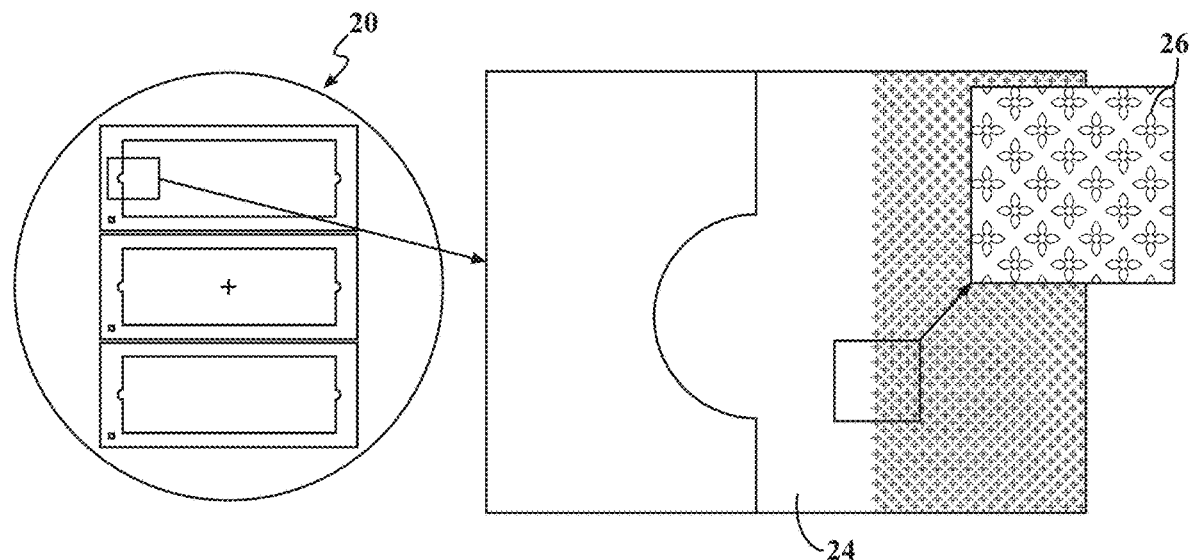
FIG. 4D is a schematic of one embodiment of a design of a microfluidic device and includes an inset magnified view of a portion of a substrate that includes a plurality of extensions (e.g. gold nanoposts) disposed thereon in a flower pattern similar to the pattern set forth in FIG. 4B.

For example, in FIG. 4C, the dimensions of (A) may be 2 to 500 µm or any other value or range of values set forth in the table of FIG. 25A or any value or range of values therebetween. The dimensions of (B) may be 5 to 2000 µm or any other value or range of values set forth in the table of FIG. 25B or any value or range of values therebetween. The dimensions of (C) may be 2 to 1000 µm or any other value or range of values set forth in the table of FIG. 25C or any value or range of values therebetween. The dimensions of (D) may be 2 to 500 µm or any other value or range of values set forth in the table of FIG. 25D or any value or range of values therebetween. In one embodiment, the dimensions of (A), (B), (C), and (D), are 25 µm, 100 µm, 36.5 µm, and 25 µm, respectively. Any of the aforementioned values may, for example, vary by 1, 2, 3, 4, 5, 10, 15, 20, or 25+% in varying non-limiting embodiments. All values, and ranges of values, between and including the aforementioned values and the values in the tables are also hereby expressly contemplated in various non-limiting embodiments.

In other embodiments, the extensions (26) are disposed in patterns, e.g. patterns having a length, width, and/or spacing of about 150 nanometers (e.g. with about a 1.5 micrometer pitch). In still other embodiments, the extensions (26) are disposed with a 1, 2, 3, 4, 5, 6, 7, 8, 9, 10, 15, 20, 25, 30, 35, 40, 45, 50, 55, 60, 65, 70, 75, 80, 85, 90, 95, of 100 µm, distance between extensions (26) and a shift between at least two rows of an independent distance that may be one of the values described immediately above, e.g. 10, 20, 30, 40, 50, 60, 70, 80, 90, or 100 µm, or ranges thereof. In one embodiment, the extensions (26) are disposed in an equilateral triangular arrangement with a 50 µm distance between extensions (26) and a 50 µm shift after every 3 rows. Any of the aforementioned values may, for example, vary by 1, 2, 3, 4, 5, 10, 15, 20, or 25+% in varying non-limiting embodiments. All values, and ranges of values, between and including the aforementioned values are also hereby expressly contemplated in various non-limiting embodiments.

In other embodiments, the pitch distances may be from 1 µm to 1000 µm (i.e., 1 mm). In various embodiments, the pitch distance is from 1 to 100, 5 to 95, 10 to 90, 15 to 85, 20 to 80, 25 to 75, 30 to 70, 35 to 65, 40 to 60, 45 to 55, or 50 to 55, µm. In other embodiments, the pitch distance is from 100 to 1000, from 125 to 975, from 150 to 950, from 175 to 925, from 200 to 900, from 225 to 875, from 250 to 850, from 275 to 825, from 300 to 800, from 325 to 775, from 350 to 750, from 375 to 725, from 400 to 700, from 425 to 675, from 450 to 650, from 475 to 625, from 500 to 600, from 525 to 575, or from 550 to 575, µm. Any of the aforementioned values may, for example, vary by 1, 2, 3, 4, 5, 10, 15, 20, or 25+% in varying non-limiting embodiments. All values, and ranges of values, between and including the aforementioned values are also hereby expressly contemplated in various non-limiting embodiments.

Figure 8:
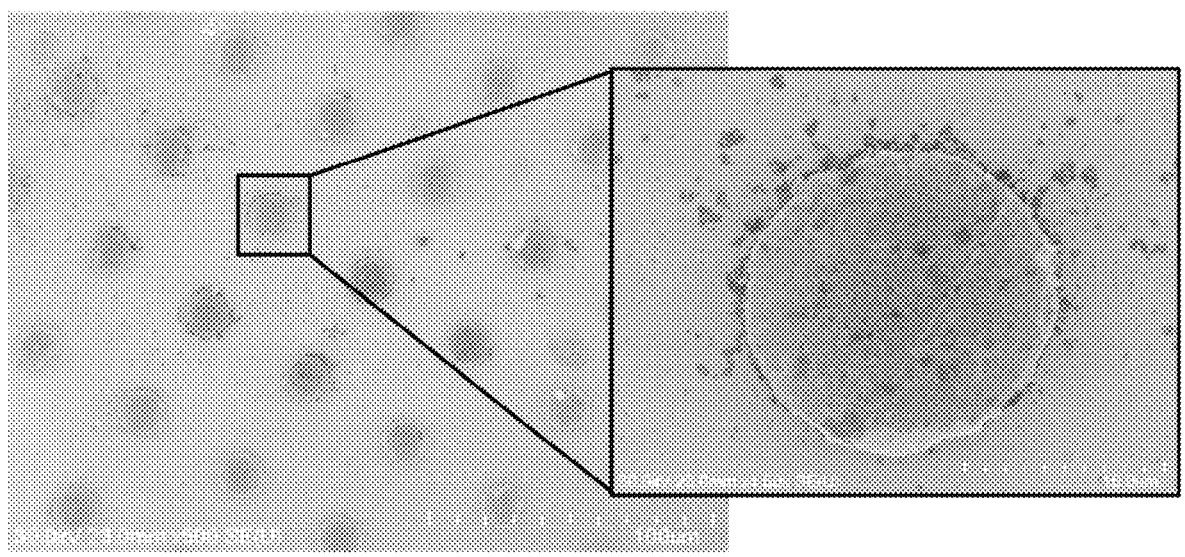
FIG. 8 includes an SEM image of extensions disposed on a silicon substrate and an inset magnified view of one of the extensions.
Figure 9A:
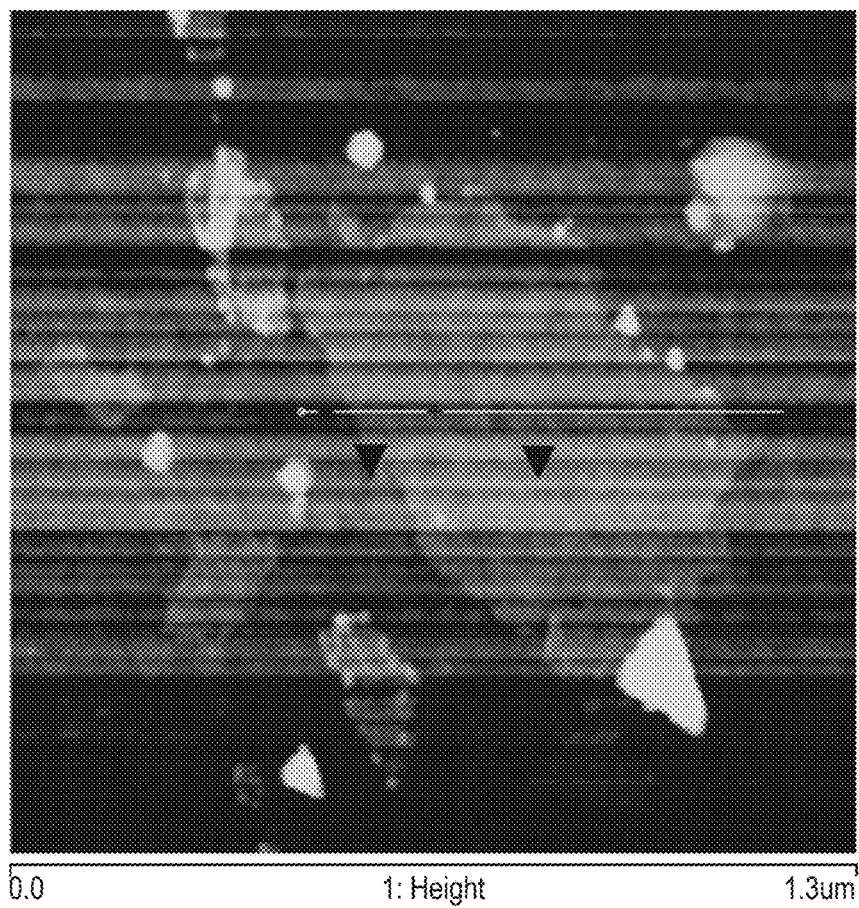
FIG. 9A is an AFM image that illustrates one embodiment of a graphene oxide sheet that has a thickness of about 2 nanometers.
Figure 9B:
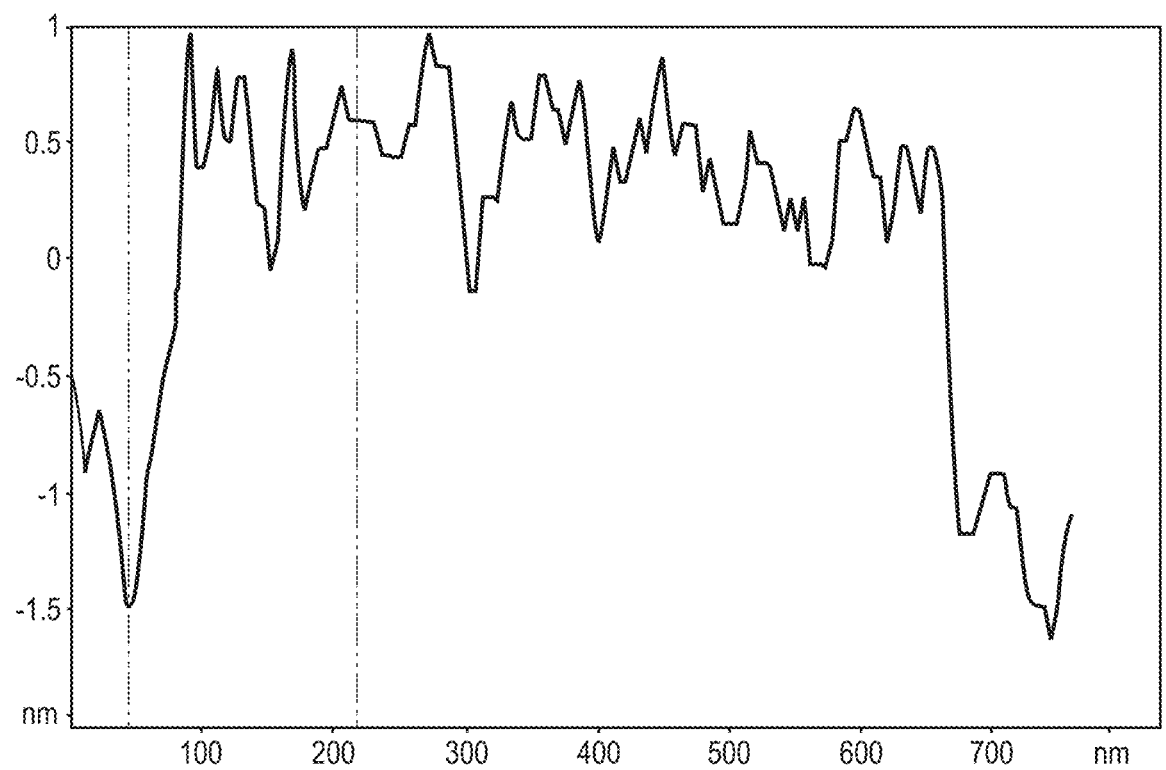
FIG. 9B is a line graph that includes data from the AFM image of FIG. 9A and further shows that one embodiment of a graphene oxide sheet has a thickness of about 2 nanometers.
Figure 9C:
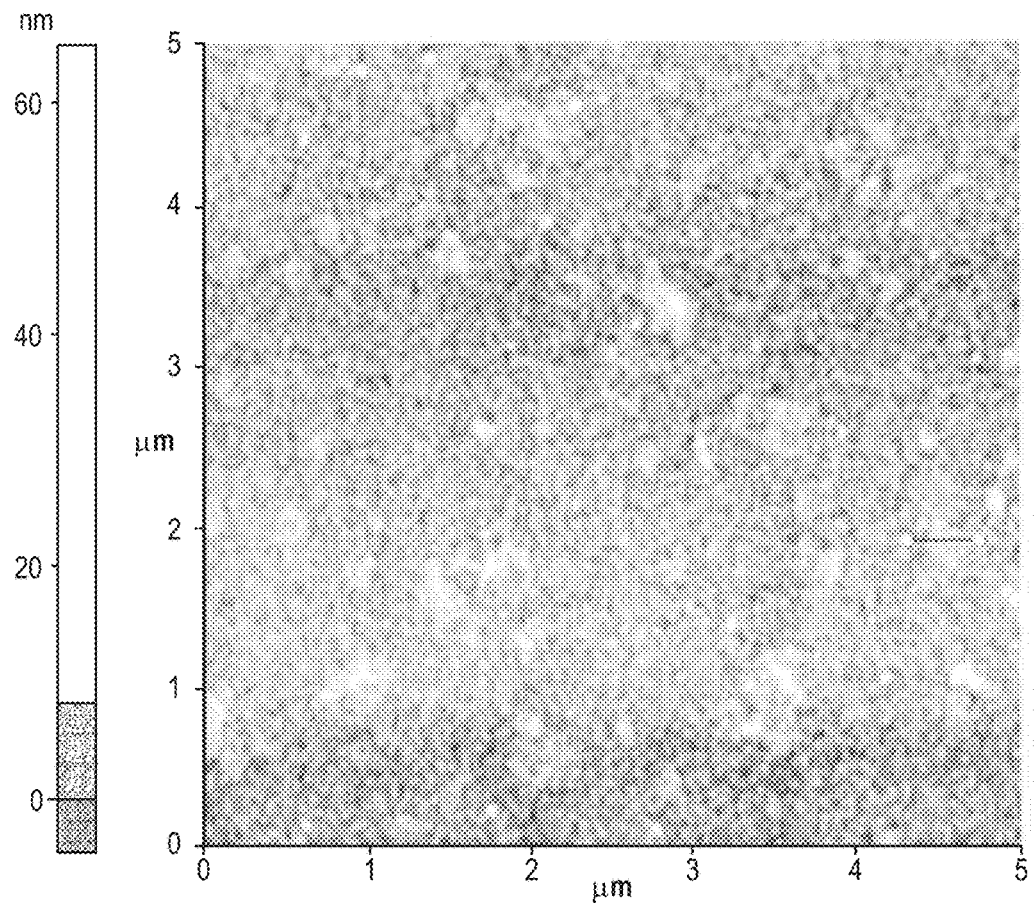
FIG. 9C is another AFM image that illustrates one embodiment of a graphene oxide sheet that has a thickness of about 3 nanometers.
Figure 9D:
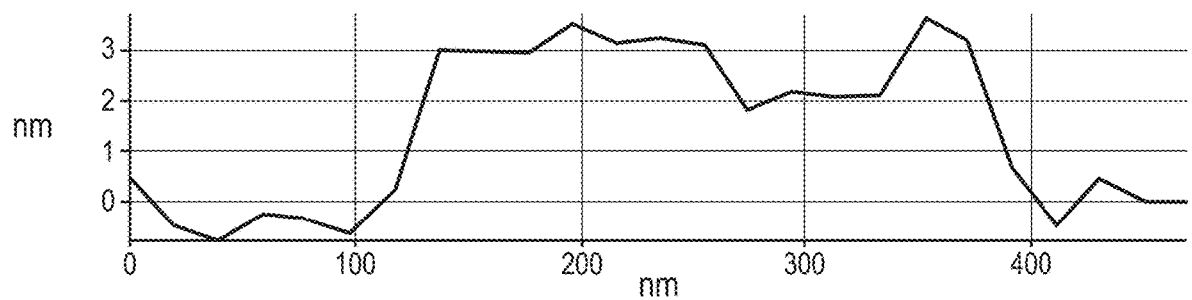
FIG. 9D is a line graph that includes data from the AFM image of FIG. 9C and further shows that one embodiment of a graphene oxide sheet has a thickness of about 3 nanometers.

Functionalized Graphene Oxide:

The functionalized graphene oxide (28) of this disclosure is disposed on the extension (26) or on more than one extension (26), for examples, as shown in FIG. 8. The graphene oxide (28), either pre- or post-functionalization, may be disposed on, or attached to, one or more extensions (26) by any means known in the art including both physical and chemical attachment including covalent bonding, electrostatic attraction, etc. In one embodiment, the extensions (26) are exposed to a compound, such as TBA Hydroxide, that facilitates binding of the graphene oxide (28) to the extensions (26), see e.g. FIG. 10. Without intending to be bound by any particular theory, it is believed that TBA Hydroxide forms a cation (+) that interacts with anions (−) (e.g. gold anions) of the extensions (26).

Figure 16A:
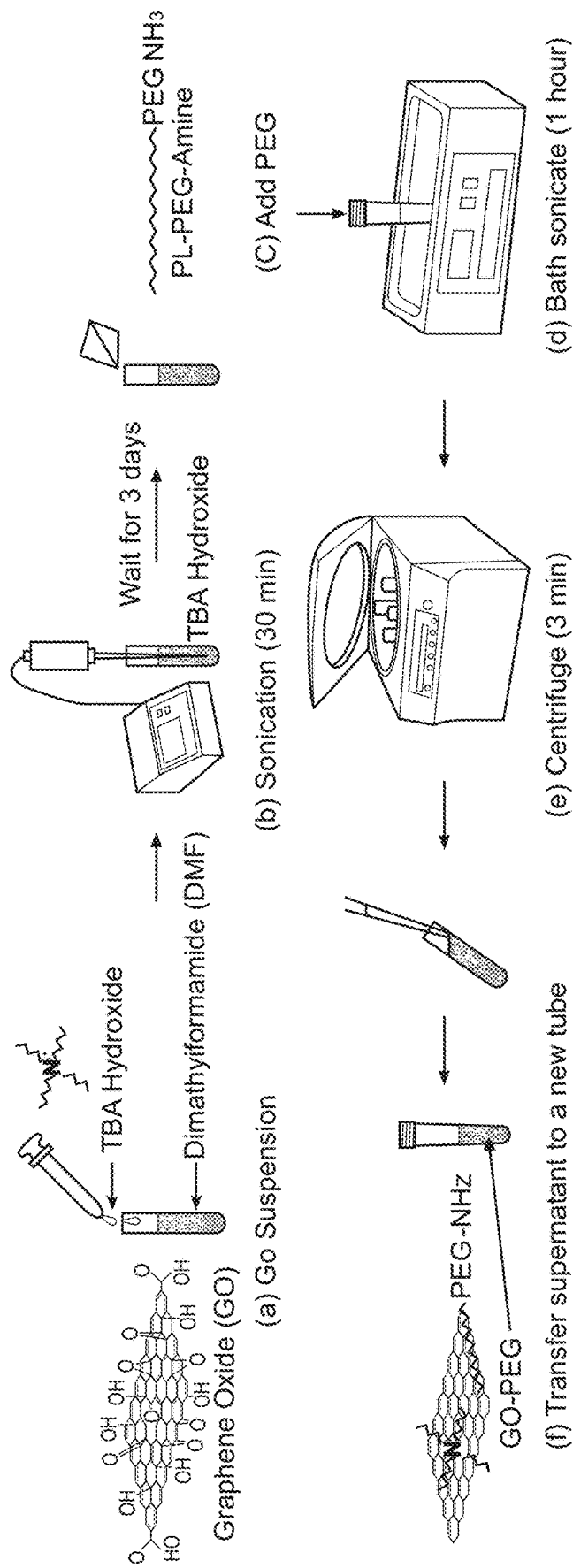
FIG. 16A is a schematic of various method steps included in one embodiment of the instant disclosure.
Figure 16B:
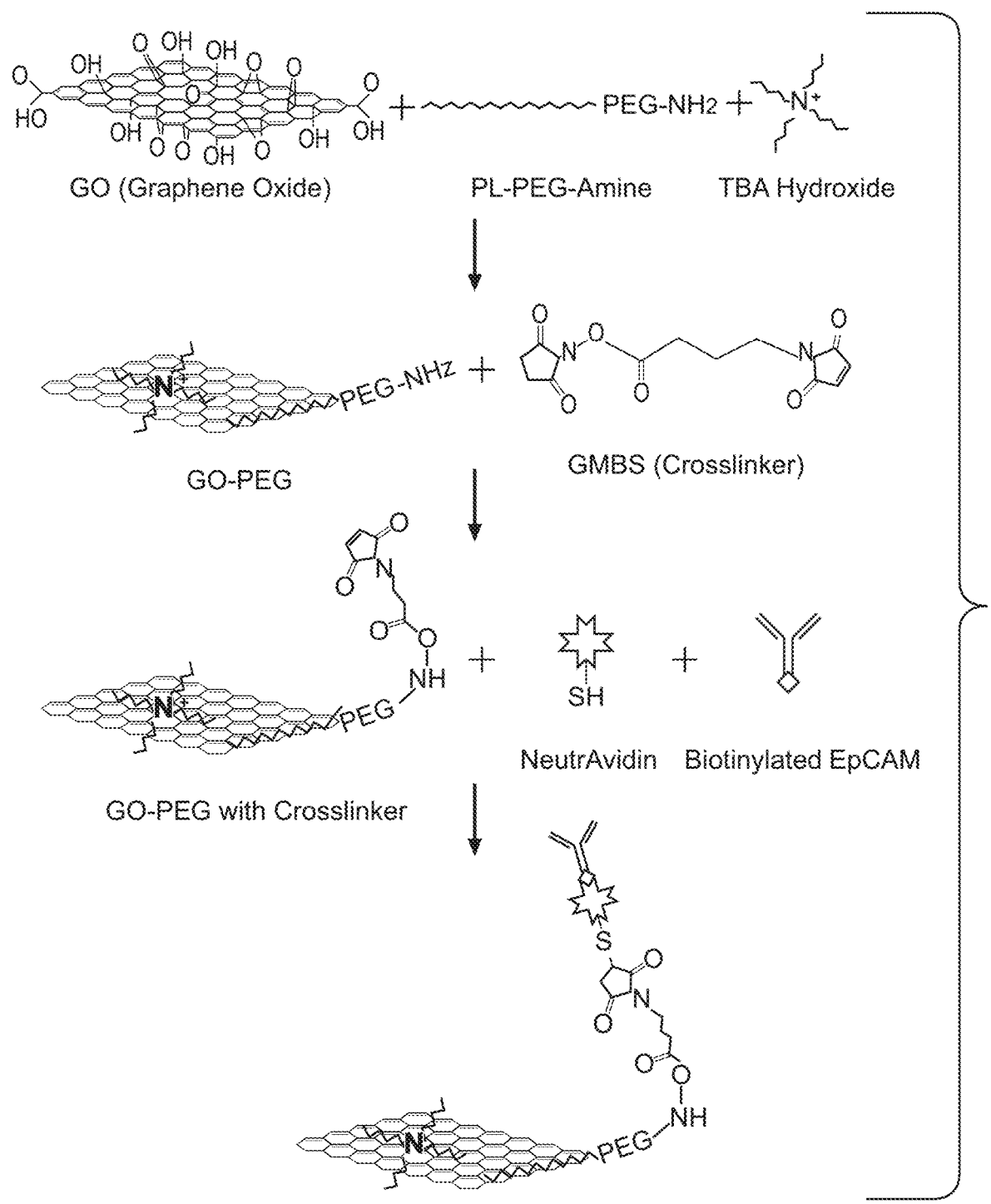
FIG. 16B is a schematic of various method steps included in another embodiment of the instant disclosure.

The extensions (26) may include one or more types of (functionalized) graphene oxide (28) and one or more markers, binding agents, etc., bonded or attached thereto, see e.g. FIGS. 16A/B. For example, multiple binding agents may hind to the same or different cells and may be placed in the same or different microfluidic channels (32) or on the same or different extensions (26).

Graphene oxide is a single layer form of graphite oxide and can be further defined as a form of graphene that includes oxygen functional groups on basal planes and edges. Typically, graphene oxide is described as a strong paper-like material. Graphene oxide, whether functionalized or not functionalized, may have a thickness of about 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, or 5.0 nm, or up to 50 nm, e.g. in tenth- or half-nanometer increments, each ±0.1, 0.2, 0.3, 0.4, 0.5, 0.6, 0.7, 0.8, 0.9, or 1.0, nm, see e.g. FIGS. 9A-D. In various embodiments, the combined height of the (functionalized) graphene oxide and the extension is from 1 µm to 1000 µm (i.e., 1 mm). In various embodiments, the combined height is from 1 µm to 100, 5 to 95, 10 to 90, 15 to 85, 20 to 80, 25 to 75, 30 to 70, 35 to 65, 40 to 60, 45 to 55, or 50 to 55, µm. In other embodiments, the combined height is from 100 to 1000, from 125 to 975, from 150 to 950, from 175 to 925, from 200 to 900, from 225 to 875, from 250 to 850, from 275 to 825, from 300 to 800, from 325 to 775, from 350 to 750, from 375 to 725, from 400 to 700, from 425 to 675, from 450 to 650, from 475 to 625, from 500 to 600, from 525 to 575, or from 550 to 575, µm. Any of the aforementioned values may, for example, vary by 1, 2, 3, 4, 5, 10, 15, 20, or 25+% in varying non-limiting embodiments. All values, and ranges of values, between and including the aforementioned values are also hereby expressly contemplated in various non-limiting embodiments.

In one embodiment, the graphene oxide is formed from graphite, as described in D. Li, M. B. Muller, S. Gilje, R. B. Kaner, and G. G. Wallace, "Processable aqueous dispersions of graphene nanosheets," *Nature Nanotechnolgy*, vol, 3, pp. 101-105, 2008, which is expressly incorporated herein by reference in a non-limiting embodiment. In another embodiment, the graphene oxide is formed using the procedure as described in Z. Wei, D. E. Barlow, and P. E. Sheehan, "The Assembly of Single-Layer Graphene Oxide and Graphene Using Molecular Templates," *Nano Letters,* Vol. 8, No. 10, pp. 3141-3145, 2008, also expressly incorporated herein by reference in a non-limiting embodiment. In still another embodiment, the graphene oxide is formed from graphene sheets that are formed using the procedure as described in H. Wang, X. Wang, X. Li, H. Dai, "Chemical Self-Assembly of Graphene Sheets," *Nano Research,* Vol. 2, pp. 336-342, 2009, also expressly incorporated herein by reference in a non-limiting embodiment. In even another embodiment, the graphene oxide is formed using the procedure described in X. Sun, Z. Liu, K. Welsher, J. T. Robinson, A. Goodwin, S. Zaric, H. Dai "Nano-Graphene Oxide for Cellular Imagine and Drug Delivery" *Nano Research*, Vol, 1, pp. 203-212, 2008, also expressly incorporated herein by reference in a non-limiting embodiment. It is also contemplated that the graphene oxide may be formed using the procedure described in U.S. Pat. App. Pub. No. US 2010/0028681, which is also expressly incorporated herein by reference in a non-limiting embodiment.

In one embodiment, graphene oxide sheets are formed by exfoliation-reintercalation-expansion methods, as described above. In another embodiment, ground natural graphite is intercalated by oleum in the presence of sodium nitrate. The product may then be treated with an aqueous solution of tetrabutylammonium (TBA) hydroxide and suspended by PL-PEG-NH$_2$ in DMF.

In still other embodiments, the graphene oxide sheets can be formed on the surface of the extensions (26). Without intending to be bound by any particular theory, it is believed that selective absorption of graphene sheets onto the extensions (26), e.g. gold patterns, can occur via electrostatic interactions. Suitable, but non-limiting, graphene oxide (28) sheets can have sizes, e.g. length and/or width, from about 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, or 975 nm, to about 1 micrometer. Alternatively, the upper range of the length and/or width may be up to 100 micrometers, e.g. in increments of, e.g. half, tenth, or hundredths, or thousandths, of a micrometer. Any of the aforementioned values may, for example, vary by 1, 2, 3, 4, 5, 10, 15, 20, or 25+% in varying non-limiting embodiments. All values, and ranges of values, between and including the aforementioned values are also hereby expressly contemplated in various non-limiting embodiments.

The graphene oxide (28) that is functionalized typically forms stable suspensions in water and can aggregate in salt or other biological solutions. In various embodiments, the graphene oxide (28) is functionalized with one or more functional groups including, but not limited to, aliphatic groups, aromatic groups, nitrogen including groups such as amines and amides, carboxyl groups, sulfur including groups, phosphorous including groups, and the like. Alternatively, the graphene oxide (28) can be functionalized with one or more markers, antibodies, antigens, proteins, tumor specific binding agents (e.g. anti-EpCAM), and the like. In another embodiment, the terminology "tumor specific binding agent" describes an agent that binds to a nonhemopoietic cell that can form a tumor, such as a cell not of hemopoietic origin, excluding blood cells and immune cells, but including epithelial cells, endothelial cells, neurons, hepatocytes, nephrons, glial cells, muscle cells, skin cells, adipocytes, fibroblasts, chondrocytes, osteocytes, and osteoblasts. The binding agent may bind to a cell surface marker that is specific for a type of cell that can form a tumor and that is not normally found in circulating blood. In an alternative, the binding agent may bind to a cell surface marker that is specific for a transformed cell. Such agents may also bind to healthy cells circulating in blood from non-pathogenic origins, e.g., venipuncture or trauma. In other embodiments, Streptavidin and/or one or more antibodies for various viruses may be utilized.

In various embodiments, the graphene oxide (28) is functionalized with one or more markers that allows for identification, enumeration, detection, capture, and/or isolation of genomic DNA, cDNA, or mRNA sequences, proteins or other intracellular contents that are indicative of a type or presence of a particular tumor, determination of the presence or absence of certain mutations in EGFR, HER2, prostate specific antigen TMPRSS2-ERG, CD133, CD44, CD24, epithelial-specific antigen (ESA), Nanog, 25 BMI1, and the like. Alternatively, the graphene oxide (28) may be functionalized with one markers that allows for identification, enumeration, detection, capture, and/or isolation of cells related, but not limited, to one or more of the following cancers: ostate, lung, adenocarcinoma, adenoma, adrenal cancer, basal cell carcinoma, bone cancer, brain cancer, breast cancer, bronchi cancer, cervical dysplasia, colon cancer, epidermoid carcinoma, Ewing's sarcoma, gallbladder cancer, gallstone tumor, giant cell tumor, glioblastoma multiforma, head cancer, hyperplasia, hyperplastic corneal nerve tumor, in situ carcinoma, intestinal ganglioneuroma, islet cell tumor, Kaposi's sarcoma, kidney cancer, larynx cancer, leiomyoma tumor, liver cancer, malignant carcinoid, malignant hypercalcemia, malignant melanomas, marfanoid habitus tumor, medullary carcinoma, metastatic skin carcinoma, mucosal neuromas, mycosis fungoide, neck cancer, neural tissue cancer, neuroblastoma, osteogenic sarcoma, osteosarcoma, ovarian tumor, pancreas cancer, parathyroid cancer, pheochromocytoma, primary brain tumor, rectum cancer, renal cell tumor, retinoblastoma, rhabdomyosarcoma, seminoma, skin cancer, small-cell lung tumor, non-small cell lung cancer (NSCLC), soft tissue sarcoma, squamous cell carcinoma, stomach cancer, thyroid cancer, topical skin lesion, veticulum cell sarcoma, Wilm's tumor, and/or combinations thereof.

In one embodiment, the graphene oxide (28) is functionalized with polyethylene glycol. For example, expandable graphite may be exfoliated and heated at about 900° C. for about 1 hour under argon to remove intercalated acid molecules. Then, a salt such as NaCl may be added and removed by filtration with water to reduce particle size. Then, a strong acid, such as sulfuric acid, may be added to effect intercalation. Further, an oxidizing agent such as $KMnO_4$ may be added and the product may be washed. Subsequently, carboxylic acid functional groups made be added along with NaOH followed by sonication, neutralization, filtering and washing. The product formed is then typically a carboxylic acid modified graphite oxide (GO-COOH). This product may be then sonicated with a 6-arm polyethylene glycolamine and N-(3-dimethylaminopropyl-N'-ethylcarbodiimide) hydrochloride may be added. Finally, mercaptoethanol may be added and the product subjected to centrifugation in PBS to form NGO-PEG.

In still other embodiments, the graphene oxide (28) is functionalized with a linking molecule (36), e.g. a linker such as GMBS which is known as N-[γ-maleimidobutyryloxy]succinimide ester in the art. The linking molecule (36) is not particularly limited. It is also contemplated that the graphene oxide (28) and/or the linking molecule (36) may be functionalized or bonded to a marker (38) such as a protein such as NeutrAvidin, see e.g. FIGS. 12A/B and 14A/B. The protein may be directly bonded to the graphene oxide (28) and/or the linking molecule (36). It is further contemplated that the graphene oxide (28), the linking molecule (36), and/or the marker (38) may be functionalized or bonded to an antibody (40) such as EpCAM against the EpCAM antigen expressed on the surface of cancer cells. The antibody (40) may be directly bonded to the graphene oxide (28), the linking molecule (36), and/or the marker (38). In one embodiment, as shown in FIG. 1, the graphene oxide (28) is disposed on a plurality of extensions (26), is functionalized with (i.e., bonded to) a linking molecule (36) which, in turn, is functionalized with (i.e., bonded to) a protein which, also in turn, is functionalized with (i.e., bonded to) an antibody (40). The antibody (40) can then bind a rare cell (22) such as a CTC. The instant disclosure is not limited to the aforementioned antibodies, proteins, etc. and one or more known in the art may be utilized and bonded to the graphene oxide (28). Suitable non-limiting examples include various antibodies and/or proteins, epithelial surface markers such as EGFR, prostate markers such as PSMA, PSA, cancer cell markers such as CD133, CD44, ALDH, endothelial markers such as CD31, CD34, leukocyte markers such as CD45, CD4, exosome/microvessicle markers such as CD63, etc. Alternatively, various peptides recognizing particular DNA sequences may be utilized.

In one embodiment, the graphene oxide is functionalized with a binding agent, the binding agent includes the reaction product of phospholipid-polyethylene-glyco-amine (PL-PEF-NH$_2$) and N-γ-maleimidobutyryloxy succinimide ester (GMBS), the reaction product is further bonded to a protein, and the protein is further bonded to an antibody for interaction with the rare cells.

Additional Non-Limiting Embodiments of a Microfluidic Device:

In one embodiment, the system (20) is further defined as a microfluidic device. The microfluidic device (and/or system (20)) may include a microfluidic channel (32) and/or a microfluidic chamber (56) through which blood, body fluids, and/or other substances can flow. Two non-limiting examples of suitable microfluidic channels (32) are set forth in FIGS. 2D and 2E. Typically, larger devices include microfluidic chambers (56) as opposed to microfluidic channels (32), but this is not necessarily true in every embodiment. The microfluidic device (and/or system (20) and/or microfluidic channel (32) and/or microfluidic chamber (56)) may also include one, two, or a plurality of posts (54), such as PDMS posts, to support one or more chambers, channels, or layers, see e.g. FIG. 3.

In one embodiment, the microfluidic device has one or more microfluidic channels (32) and/or chambers (56) one or more of which each independently having a length, height, and/or width of from 1 μm to 1000 μm (i.e., 1 mm) In various embodiments, one or more of these values is from 1 μm to 100, 5 to 95, 10 to 90, 15 to 85, 20 to 80, 25 to 75, 30 to 70, 35 to 65, 40 to 60, 45 to 55, or 50 to 55, μm. In other embodiments, one or more of these values is from 100 to 1000, from 125 to 975, from 150 to 950, from 175 to 925, from 200 to 900, from 225 to 875, from 250 to 850, from 275 to 825, from 300 to 800, from 325 to 775, from 350 to 750, from 375 to 725, from 400 to 700, from 425 to 675, from 450 to 650, from 475 to 625, from 500 to 600, from 525 to 575, or from 550 to 575, μm. In other embodiments, the width may be up to 5 mm, and the length up to 100 to 1000 mm. The dimensions of the microfluidic device, as a whole, are not particularly limited. In various embodiments, e.g. as set forth in the Figures, $L_2$ and $L_3$ may be from 5 to 100 mm, $W_2$ and $W_3$ may be from 5 to 50 mm, and $T_1$ and $T_2$ may be from 100 μm to 10 mm. Any of the aforementioned values may, for example, vary by 1, 2, 3, 4, 5, 10, 15, 20, or 25+% in varying non-limiting embodiments. All values, and ranges of values, between and including the aforementioned values are also hereby expressly contemplated in various non-limiting embodiments.

One of more microfluidic channels (32) and/or chambers (56) may each individually have a unique shape and/or structure. In addition, one microfluidic channel (32) and/or chamber (56) may have a shape or pattern different from another microfluidic channel (32) and/or chamber (56) in the same device. The geometry of these patterns is also not particularly limited. The patterns may be geometric, non-geometric, uniform or non-uniform, e.g. straight, zig-zag, herringbone, circular or oval, triangular, whorl-shaped, ribbon-shaped, marble, spiral-shaped, coil-shaped, curl-shaped, twisted, looped, helix, serpentine, sinusoidal, winding, and/or random, and the like.

Suitable but non-limiting microfluidic devices are described in WO2009/051734 and PCT/US10/53221, each of which is expressly incorporated herein by reference in non-limiting embodiments. Additional suitable but non-limiting microfluidic devices are set forth in FIGS. 2A-2G. Other suitable, but non-limiting, microfluidic devices are described in S. Wang et al., "Highly Efficient Capture of Circulating Tumor Cells by Using Nanostructured Silicon Substrates with Integrated Chaotic Micromixers," *Angewandte Chemie*, vol 50, pp. 3084-3088, 2011, which is expressly incorporated herein by reference in non-limiting embodiments. As described in this reference, it is contemplated that this disclosure may utilize silicon nanopillars and/or PDMS channels.

The microfluidic device may include one or more walls (30) oriented substantially perpendicularly, or transversely, to a floor (42), supplemental layers (34), microfluidic channels (32) and/or microfluidic chambers (56). As set forth in FIG. 1A, the microfluidic device may also have a central body (44), a longitudinal axis ($L_1$), and upstream and downstream ends (46, 48) opposite each other, wherein the central body (44) defines the microfluidic channel (32) and/or microfluidic chambers (56) which is in fluid communication with the upstream and downstream ends (46, 48) along the longitudinal axis ($L_1$) for receiving the sample. The microfluidic device may also include an entrance (50) (i.e. inlet) defined by the central body (44) and disposed at the upstream end (46) of the central body and include an exit (52) (i.e., outlet) also defined by the central body (44) and disposed at the downstream end (48) of the central body (44) wherein both the entrance (50) and exit (52) are disposed transverse to the longitudinal axis ($L_1$).

The geometry of the microfluidic channel (32) and the one or more walls (30) is not particularly limited but may be designed to increase or decrease flow through, velocity through, or pressure in, the microfluidic channel (32).

The microfluidic device may include a single microfluidic channel (32) and/or chamber (56), two microfluidic channels (32) and/or chambers (56), or three or more (i.e., a plurality of) microfluidic channels (32) and/or chambesr (56). The microfluidic channels (32) and/or chambers (56) can be arranged in series, in parallel, or in any geometric or puzzle configuration as selected by one of skill in the art. In one embodiment, one or more microfluidic channels (32) and/or chambers (56) are arranged in an approximate herringbone pattern. Each individual microfluidic channel (32) and/or chamber (56) may be used to isolate one or more types of material or rare cells (22). In various embodiments, a sample of blood, bodily fluid, etc. is segmented into two or more segments and the segments flow through different microfluidic channels (32) and/or chambers (56) at one or more pressures and/or velocities.

The microfluidic device may be designed to allow for optical or visual inspection of the microfluidic channels (32) and/or microfluidic chambers (56). For example, the microfluidic device may include a top (58), bottom (62), and/or side (60), e.g. as set forth in FIG. 2C, which may be transparent to allow for optical or visual inspection. Alternatively, the microfluidic device may include a top, bottom, and/or side which may be opaque. It is also contemplated that the microfluidic device may not include a top.

In addition, the microfluidic device may be designed to maximize efficiency relative to flow, velocity and/or shear force of a sample passing therethrough. In various embodiments, the maximum shear force exerted on a cell, based on a volumetric flow rate of about 1 mL/h, is about 0.4 dynes/cm$^2$ at θ=68°, and the maximum velocity is about 460 μm/s. The shear stress produced in a microfluidic channel (32) and/or microfluidic chamber (56) is typically of from about 0.1 to about 20 dyn/cm$^2$ and may be less than 15, 10, 5, 1, or 0.5, dyn/cm$^2$. Shear stress is not necessarily constant throughout a microfluidic channel (32). In other embodiments, a sample may be transported through the microfluidic channel (32) and/or chamber (56) at a rate of 0.1 mL to 30 mL/hr. Typical flow rates are typically from 0.5 to 1, from 1 to 20, 2 to 19, 3 to 18, 4 to 17, 5 to 16, 6 to 15, 7 to 14, 8 to 13, 9 to 12, or 10 to 11, mL/hr. However, these rates are not limiting and the rate at which the sample passes through may be greater or less than those described above. Any of the aforementioned values may, for example, vary by 1, 2, 3, 4, 5, 10, 15, 20, or 25+% in varying non-limiting embodiments. All values, and ranges of values, between and including the aforementioned values are also hereby expressly contemplated in various non-limiting embodiments.

The volume of the microfluidic channel (32) and/or microfluidic chamber (56) may be customized depending on a volume of the sample used. The volume of the microfluidic channel (32) and/or microfluidic chamber (56) may be smaller or larger than the size of the sample or may be approximately the same as the size of the sample. In various embodiments, the microfluidic device and/or the microfluidic channel (32) and/or microfluidic chamber (56) has a volume of from about 10 μL to 20 mL, from about 100 μL to 15 mL, from about 100 μL to 10 mL, from about 100 μL to 5 mL, from about 100 μL to 1 mL, or from about 100 μL to 0.5 mL. However, these volumes are not limiting and the volume of the microfluidic device and/or the microfluidic channel (32) and/or microfluidic chamber (56) may be greater or less than those described above. Any of the aforementioned values may, for example, vary by 1, 2, 3, 4, 5, 10, 15, 20, or 25+% in varying non-limiting embodiments. All values, and ranges of values, between and including the aforementioned values are also hereby expressly contemplated in various non-limiting embodiments.

The microfluidic channel (32) and/or microfluidic chamber (56) may be modified to increase surface area, volume, etc. to increase a probability that a rare cell with be captured. For example, when the walls (30) are substantially planar, the height of the microfluidic channel (32) and/or microfluidic chamber (56) may be designed so that rare cells are more efficiently detected and/or trapped.

The microfluidic device is not particularly limited to any particular efficiency. However, in various embodiments, the microfluidic device can typically identify, enumerate, detect, capture, and/or isolate from 1 to 10,000, 1 to 7,500, 1 to 5,000, 1 to 2,500, 1 to 1500, from 5 to 1000, from 10 to 500, from 25 to 200, or from 50 to 100, rare cells (22) from a blood sample of about 1 mL or less. Alternatively, the system (20) and/or microfluidic device may have a rare cell capture efficiency of at least 1, 5, 10, 15, 20, 25, 30, 35, 40, 45, 50, 55, 60, 65, 70, 75, 80, 85, 90, 95, or 99, percent determined as (rare cells captured on the (functionalized) graphene oxide (or any protein, antibody, marker, etc. bound thereto) divided by a total number of rare cells introduced to the system and/or microfluidic device) multiplied by 100. In other embodiments, the system (20) and/or microfluidic device may have a rare cell capture efficiency of 95 to 100, 90 to 95, 90 to 100, 85 to 95, 85 to 90, 80 to 85, 80 to 90, 80 to 95, 75 to 80, 75 to 85, 75 to 90, 75, to 95, 70 to 75, 70 to 80, 70 to 85, 70 to 90, 75 to 95, 50 to 95, 55 to 90, 60 to 85, 65 to 80, 65 to 75, 65 to 70, 25 to 50, 59 to 75, or 25 to 75, percent, as determined using the formula described immediately above. In various embodiments, the microfluidic device has a rare cell capture efficiency of about 70, 75, or 80 plus or minus about 20, 25, or 30, at 5-20 cells/mL spiked in blood. Any of the aforementioned values may, for example, vary by 1, 2, 3, 4, 5, 10, 15, 20, or 25+% in varying non-limiting embodiments. All values, and ranges of values, between and including the aforementioned values are also hereby expressly contemplated in various non-limiting embodiments.

in various embodiments, the microfluidic device and system may capture, on average, about 155±236 CTCs/mL for NSCLC, about 16 to 292 CTCs/mL for metastatic prostate, about 25 to 174 CTCs/mL for localized prostate cancer, about 9 to 831 CTCs/mL for pancreatic cancer cells, about 5 to 176 CTCs/mL for breast cancer cells, and about 42 to 375 (121±127) CTCs/mL for colorectal cancer cells. The microfluidic device may allow captured cells to be grown and cultivated, see e.g. FIGS. 17 and 22-24, and/ or washed such that non-specifically bound cells, e.g., leukocytes, may be removed which may result in about a $10^6$-fold enrichment. Any of the aforementioned values may, for example, vary by 1, 2, 3, 4, 5, 10, 15, 20, or 25+% in varying non-limiting embodiments. All values, and ranges of values, between and including the aforementioned values are also hereby expressly contemplated in various non-limiting embodiments.

The microfluidic device may also include or be coupled to one or more components such as reservoirs, pumps, valves, actuators, pipes, tubes, electrodes, meters, computers, electronic monitoring devices, analytical devices, electrical potential and/or resistance monitoring devices, and the like. Those of skill in the art may select one or more of the components to couple to the microfluidic device.

In one embodiment, the microfluidic device includes a silicon substrate that includes approximately has 60,000 extensions (e.g. formed from gold) disposed in leaf patterns having a size of 100 μm×100 μm. The distance between each extension in a column, in this embodiment, is 150 μm. The overall size of the microfluidic device of this embodiment is about 24.5 mm×60 mm×3 mm. The microfluidic device of this embodiment also includes a supplemental layer (34) that is PDMS and that has a microfluidic chamber therein wherein the chamber has a height of 50 μm and a volume of 45 μL. Graphene oxide nanosheets may be self-assembled onto the extensions, in this embodiment, at a thickness of about 100 nm. The graphene oxide of this embodiment may also be functionalized with EpCAM antibodies. It is contemplated that the aforementioned descriptions and characteristics are not necessarily limited to this particular embodiment and may apply to other embodiments described herein.

Method for Forming the System and/or Microfluidic Device:

This disclosure also provides a method of forming the system (20) and/or a microfluidic device. The method typically includes the steps of providing the substrate (24), providing the extension (26), and providing the (functionalized) graphene oxide. The substrate (24) may be provided as a single layer or as more than one layer, including one or more supplemental layers (34). Accordingly, the method may include the step of forming the substrate (24) including one or more layers. The step of forming the substrate (24) and/or the one or more supplemental layers (34) is not particularly limited, may be any known in the art, and may be as described above.

The step of providing the extension (26) is also not particularly limited and may include any method of forming and/or depositing the extension (26) on the substrate (24). For example, the method may include the step of evaporating and patterning metal (e.g. Cr/Au) layers. Alternatively, the method may include the step of etching silicon to form the extension (26).

The step of providing the (functionalized) graphene oxide again is not particularly limited. The step of providing may include, or be further defined as, forming the graphene oxide, and/or reacting the graphene oxide to functionalize the graphene oxide with one or more markers, proteins, etc. as described above. The graphene oxide may be formed and/or reacted or functionalized by any method or reaction known in the art, including those reactions and functionalization reactions described above. Each of the aforementioned substrate (24), extensions (26), and graphene oxide (28) may be assembled together to form the system and/or microfluidic device using any method known in the art.

Method for Detecting Rare Cells:

This disclosure also provides a method for detecting rare cells using the system (20) and/or microfluidic device of this disclosure. The method allows for small amounts of bodily fluid to be evaluated accuracy and precisely and in a time and cost effective manner to determine the presence of rare cells.

The method includes the steps of providing the system (20) and/or microfluidic device and introducing a sample of bodily fluid to the system (20) and/or microfluidic device such that the sample interacts with the (functionalized) graphene oxide (28) and/or any proteins, markers, antibodies, etc. bonded thereto. The method allows for small amounts of bodily fluid to be evaluated accuracy and precisely and in a time and cost effective manner to determine the presence of rare cells (22). The step of providing the system (20) and/or microfluidic device is not particularly limited and may include one or more of the aforementioned steps described as associated with the method of forming the system (20) and/or the microfluidic device.

The step of introducing a sample of bodily fluid is also not particularly limited. Typically, this step is further defined as exposing the system (20) and/or the microfluidic device and/or the extension (26) to the bodily fluid such that the bodily fluid contacts the extension (26) and the (functionalized) graphene oxide (28), which is typically modified or functionalized in such as a way as to interact with the bodily fluid in a designated manner. In one embodiment, the step of introducing the bodily fluid is further defined as injecting or adding the bodily fluid to the entrance (50) of the microfluidic device. The method may also include the step of flowing the bodily fluid through the microfluidic channel (32) and/or microfluidic chamber (56), e.g. along the longitudinal axis ($L_1$), from the upstream end (46) towards the downstream end (48) and out of the exit (52). The steps of this method may include any of the parameters and/or descriptions associated with the system, as described above.

Method For Diagnosing Cancer:

This disclosure also provides a method for diagnosing a cancer or carcinoma in a subject. This method includes the step of introducing a sample of a bodily fluid to the system (20) and determining whether any target rare cells (22) are present. Rare cells (22) obtained by the methods of the disclosure may be assayed for genetic information. In addition, the rare cells (22) may be assayed for changes in genetic information over time as well as or in the alternative to enumeration, e.g. to monitor for the appearance of mutations that indicate a change in therapy is advisable.

Method for Lysing Rare Cells:

This disclosure further provides a method of lysing rare cells (22) using the system (20) of this disclosure. This method typically includes the step of introducing a sample of a bodily fluid to the system (20) and subsequently introducing a lysing agent to the system. The lysing agent may be any known in the art.

One or more methods of this disclosure may also include the step of washing the rare cells (22) at a high shear stress or volume to increase purity and reduce the number of weakly bound or non-specifically bound rare cells (22) in the system (20) and/or microfluidic device. One or more methods of this disclosure may also include the step of counting or quantifying a number of bound rare cells (22). The rare cells (22) can be counted by any method known in the art, including optical, e.g. visual inspection, automated counting, microscopy based detection, FACS, and electrical detection, e.g. with the use of Coulter counters. Counting of the rare cells (22) can be useful for diagnosing diseases, monitoring the progress of disease, and monitoring or determining the efficacy of a treatment. The number of rare cells (22) may also be counted in non-medical applications, e.g. for determination of the amount, presence, or type of contaminants in environmental samples, pharmaceuticals, food, or cosmetics.

One or more of the methods of this disclosure may also include the step of measuring a desired characteristic of rare cells (22). For example, the method may include the step of measuring desired biological properties of rare cells (22) such as mRNA expression, protein expression, and DNA quantification.

It is also contemplated that the disclosure may include one or more elements, one or more methods, one or more devices, and/or one or more systems as described in one or more of the following references, each of which is expressly incorporated herein by reference, in one or more non-limiting embodiments: Y. Shao, J. Wang, H. Wu, J. Liu, I. A. Aksay, Y. Lin, "Graphene Based Electrochemical Sensors and Biosensors: A Review," *Electroanalysis*, Vol 22, pp. 1027-1036, 2010; Y. Liu, D. Yu, C. Zeng, Z. Miao, L. Dai, "Biocompatible Graphene Oxide-Based Glucose Biosensors," Langmuir, vol. 26, pp. 6158-6160, 2010; J. H. Jung et al., "A Graphene Oxide Based Immuno-biosensor for Pathogen Detection," *Angewandte Chemie*, vol. 122, pp. 5844-5847, 2010.

The instant disclosure may also include one or more elements, one or more methods, one or more devices, and/or one or more systems as described in the provisional application (U.S. Prov. App. Ser. No. 61/541,814) and/or appendix filed therewith. It is to be very clear and understood that nothing in any one or more of any reference cited herein and incorporated by reference herein, or in the appendix, is to limit this disclosure. The various embodiments and options described in the references, provisional patent application, and appendix which are incorporated herein by reference are not limiting, are optional, and are in no way meant to limit this disclosure.

EXAMPLES

Simulation of One Embodiment of a Pattern of Extensions in a Microfluidic Device A simulation of fluid flow in a theoretical microfluidic device is performed with Comsol Multiphysics 4.2. A three-dimensional leaf pattern of (gold) extensions disposed on a substrate is generated and analyzed with a laminar flow module, the results of which are set forth in FIGS. 6 and 7. The height of the extensions is assumed to be 3 μm although the actual height of the gold is about 100 nm. An effective height of the extensions including the gold may be as high as 1-3 μm because of addition of functional groups.

In the simulation, the effect of the leaf pattern on a fluid field is examined by increasing a height of the fluid field from 10 μm to 30 μm, see FIG. 6. The Figs. show that, at or below 10 μm, the fluid field is disturbed significantly by the leaf pattern while, as the height of the leaf pattern increases, the effect of this disturbance decreases. This disturbance may enhance the cell-surface interactions thus increase the capture efficiency.

To evaluate the performance of the leaf pattern, the simulation on a circular pattern is conducted as set forth in FIG. 7. As shown in both FIGS. 6 and 7, the simulation demonstrates that the leaf pattern outperforms the circular pattern by increasing the number of boundary layers thereby enhancing particle-surface interactions. This effect is well illustrated at 10 µm height of a channel of a microfluidic device.

Example of One Embodiment of the System/Microfluidic Device of This Disclosure

Figure 2G:
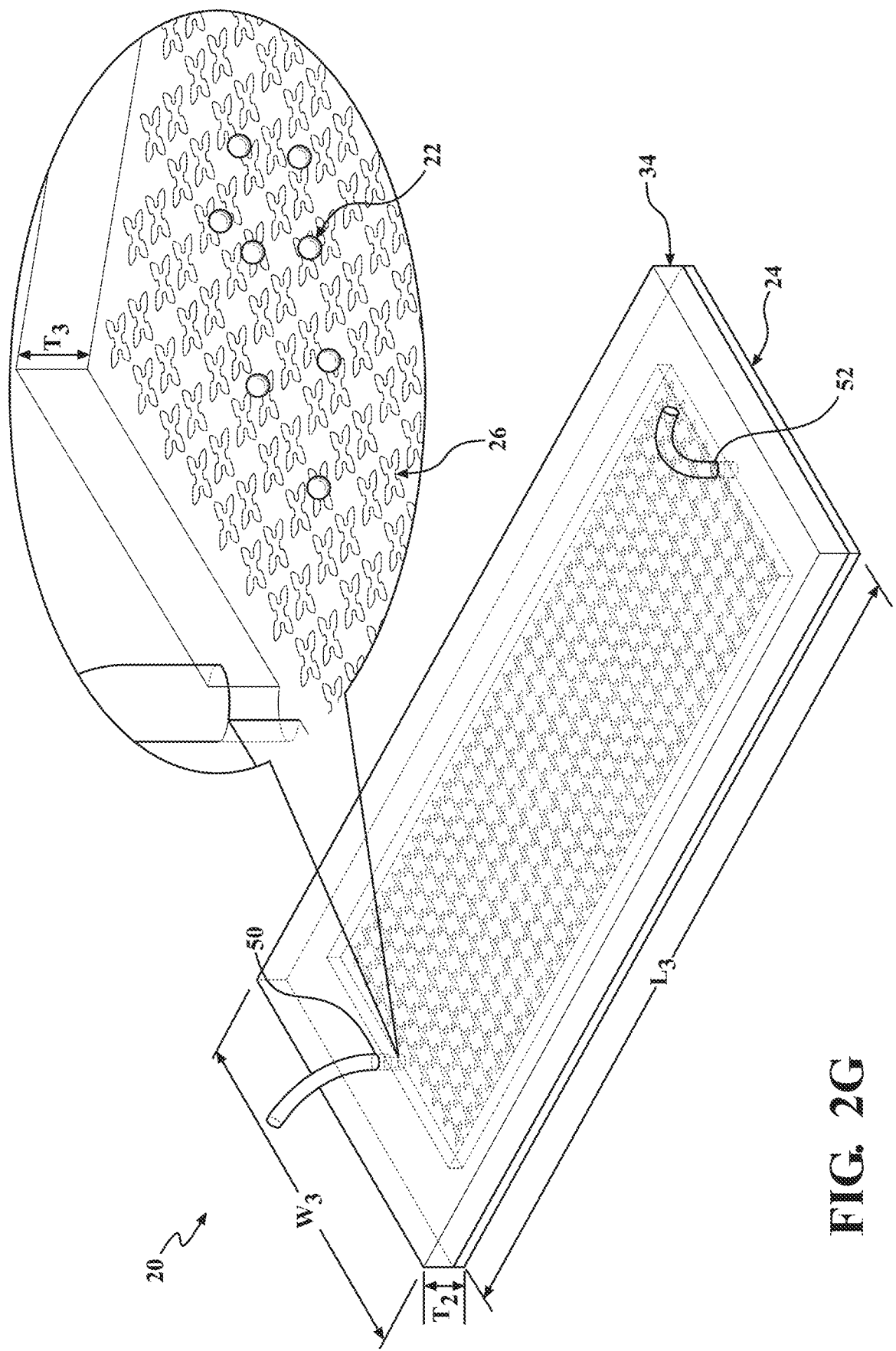
FIG. 2G is a top view of one embodiment of a microfluidic device including a magnified portion of a plurality of extensions distributed in leaf patterns on a substrate and rare cells disposed thereon.
Figure 3:
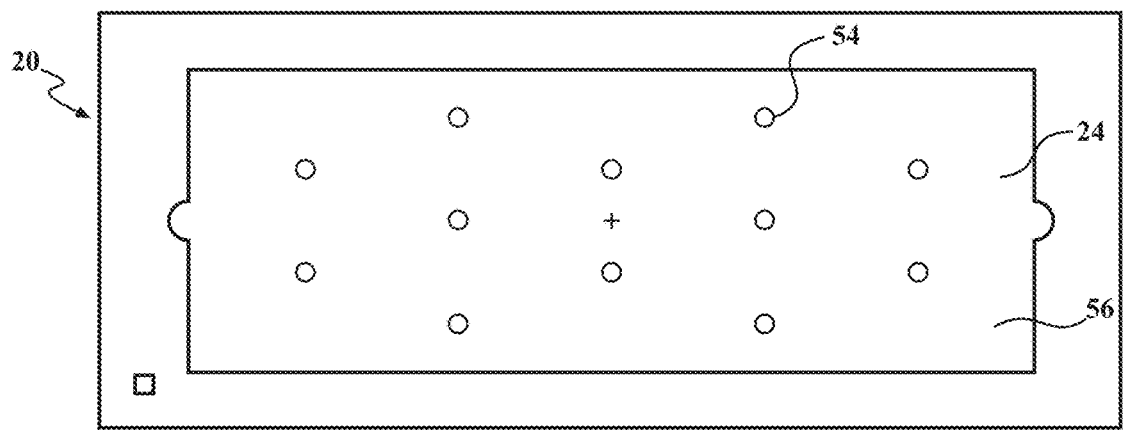
FIG. 3 is a top view still another embodiment of the microfluidic device including a plurality of extensions disposed on a substrate.

In one embodiment, the system/microfluidic device of this disclosure utilizes a flower shaped architecture for the extensions, e.g. as set forth in FIGS. 2G and 4C, disposed on a silicon substrate. The silicon substrate of this example has 58,957 flower-shaped gold extensions each having an approximate height and width of 100 µm×100 µm. The distance between each extension in a column is 150 µm. The overall size of the system/microfluidic device is 24.5 mm×60 mm×3 mm. A PDMS layer of the system/microfluidic device has a microfluidic chamber with 50 µm height and a 45 µL volume. Graphene oxide nanosheets are self-assembled onto the patterned gold extensions. The extensions including the graphene oxide are chemically functionalized with EpCAM antibodies. The effective functionalized surface area enables the system/microfluidic device to be a simple polydimethylsiloxane (PDMS) flat chamber-like structure.

More specifically, the graphene oxide of this example is non-covalently functionalized with phospholipids-polyethylene-glyco-amine (PL-PEG-NH2). The hydrophobic lipid chains of PL-PEG-NH2 are immobilized onto the surface of the graphene oxide. The functionalized graphene oxide has a high water solubility, biocompatibility, and functional groups available for further bioconjugation. Tetrabutylammonium (TBA) hydroxide is added for intercalation and complete exfoliation of graphene oxide. TBA cations and the amino group of PL-PEG-NH2 can interact with the gold surface by electrostatic attraction. N-γ-maleimidobutyryloxy succinimide ester (GMBS) has N-hydroxysuccinimide (NHS) esters that react with amine groups of graphene oxide-PEG to form amide bonds.

Figure 11A:
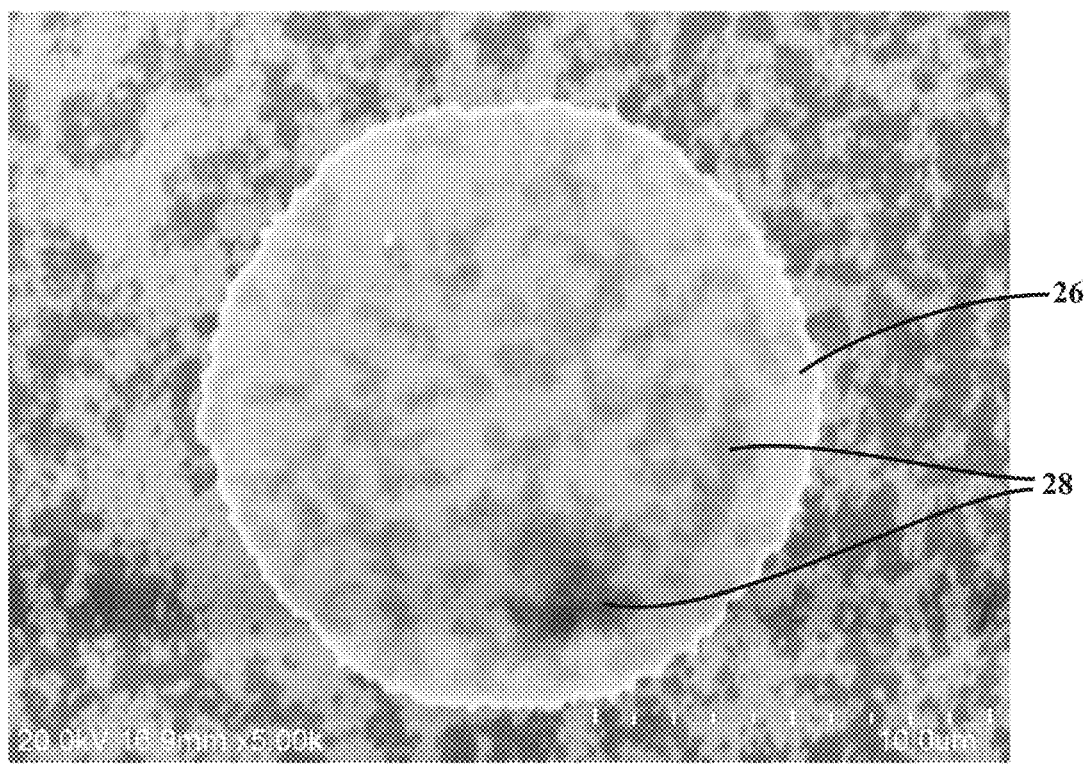
FIG. 11A is an SEM image of an extension (e.g. gold nanopost) including a plurality of graphene oxide sheets disposed thereon and not washed with IPA and DI water.
Figure 11B:
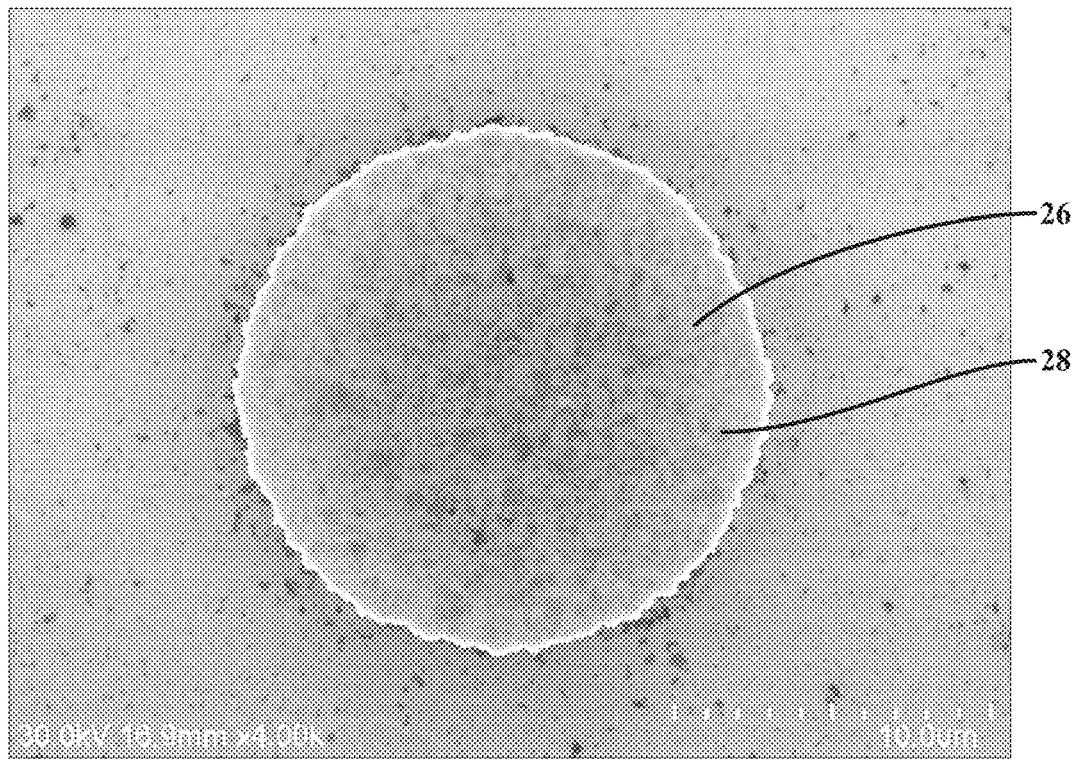
FIG. 11B is an SEM image of an extension (e.g. gold nanopost) including a plurality of graphene oxide sheets disposed thereon and washed with IPA and DI water as described in the Examples.
Figure 11C:
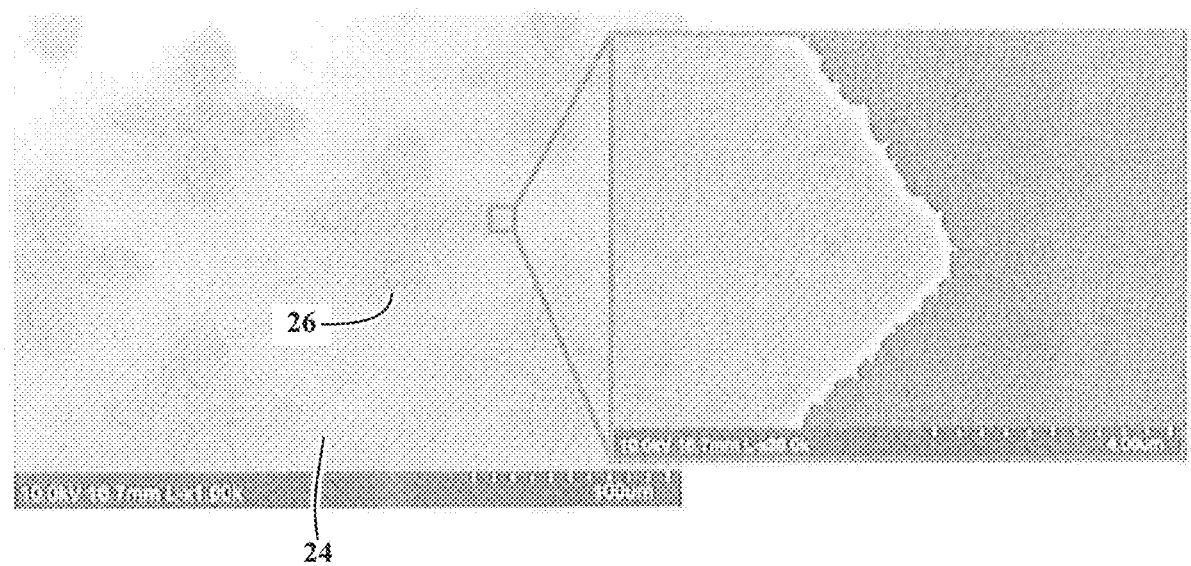
FIG. 11C is an SEM image of self-assembled graphene oxide molecules on a plurality of extensions (e.g. gold nanoposts) disposed on a substrate in multiple independent leaf patterns.

In this example, CTCs are captured by using the following NeutrAvidin and biotinylated EpCAM antibody interactions. To functionalize and self-assemble graphene oxides before bonding, the silicon substrate is dipped into a functionalized graphene oxide suspension and graphene oxide self-assembles on the gold surface of the extensions. SEM images reveal that gold patterns are covered with functionalized graphene oxides, see e.g. FIG. 11C. The functionalized graphene oxides are attached to the sides of the extensions as well as onto the top of the extensions. This phenomenon demonstrates the high selectivity of graphene oxide assembly on the gold extensions rather than onto the silicon substrate and the uniform assembly and saturation density of graphene oxide on the gold extensions. AFM images, as set forth in FIG. 11, show graphene oxide sheets are disposed on the gold extensions. The thickness of the graphene oxide in this example is about 1-3 nm.

Figure 12A:
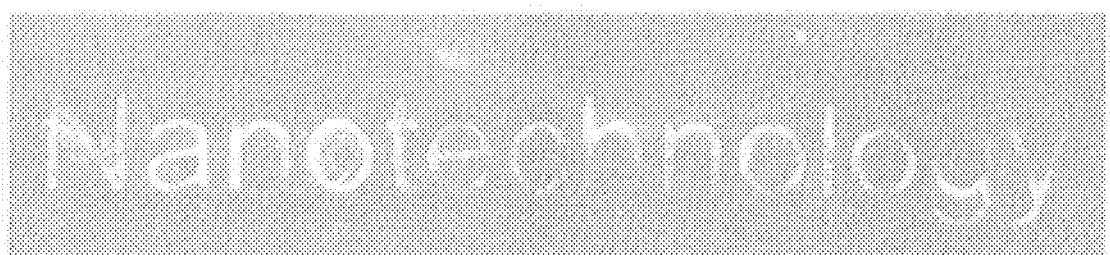
FIG. 12A is a fluorescence microscopy image of fluorescently labeled NeutrAvidin self-assembled on a plurality of extensions (e.g. gold nanoposts) that include functionalized graphene oxide disposed thereon.
Figure 12B:
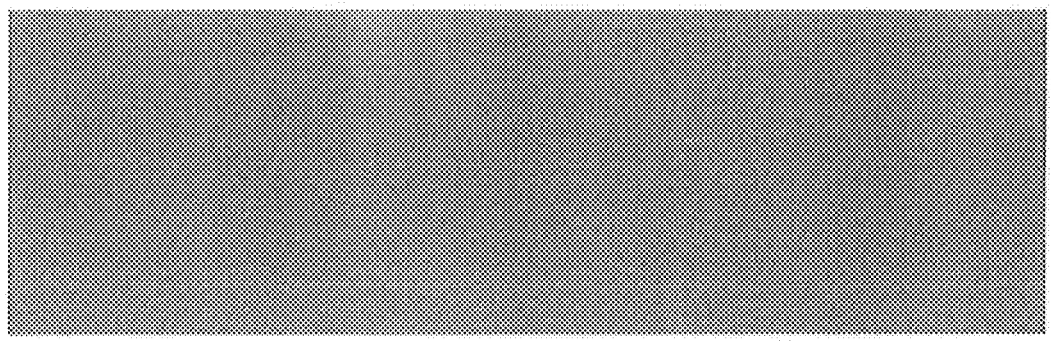
FIG. 12B is a control fluorescence microscopy image of fluorescently labeled NeutrAvidin self-assembled on a plurality of extensions (e.g. gold nanoposts) that do not include functionalized graphene oxide disposed thereon.
Figure 13A:
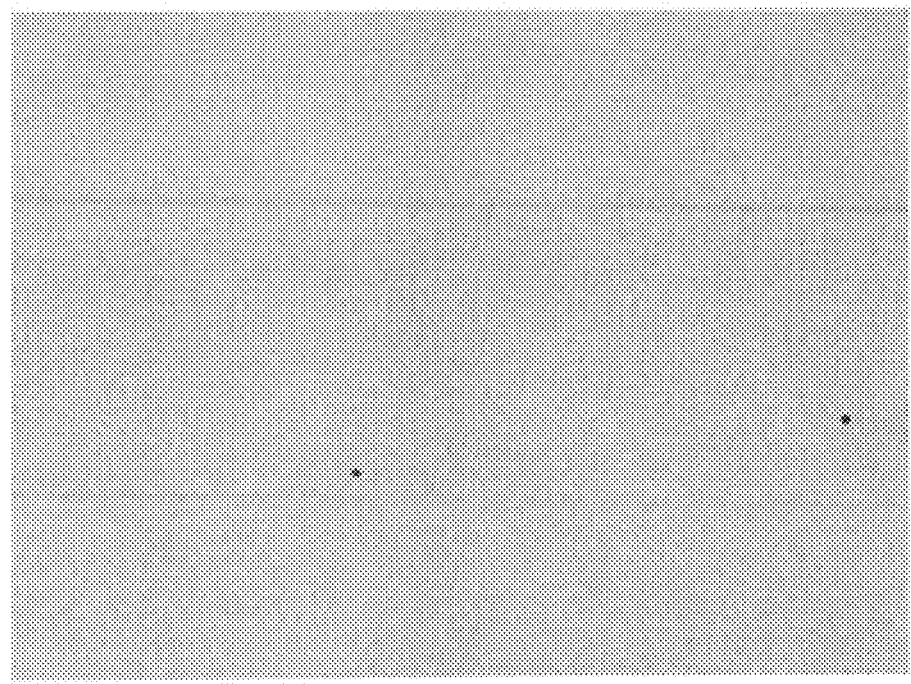
FIG. 13A is a fluorescence microscope image of captured MCF-7 cancer cells attached to antibodies disposed on a plurality of extensions (e.g. gold posts) having functionalized graphene oxide disposed thereon and in a microfluidic device similar to that illustrated in FIG. 2A.
Figure 13B:
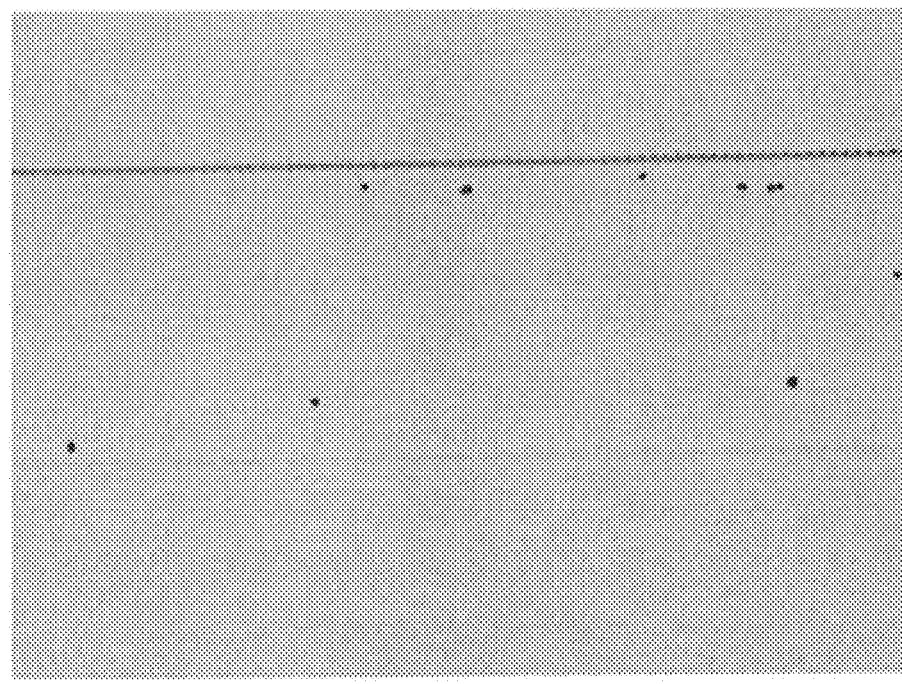
FIG. 13B is another fluorescence microscope image of captured MCF-7 cancer cells attached to antibodies disposed on a plurality of extensions (e.g. gold posts) having functionalized graphene oxide disposed thereon and in a microfluidic device similar to that illustrated in FIG. 2A.
Figure 13C:
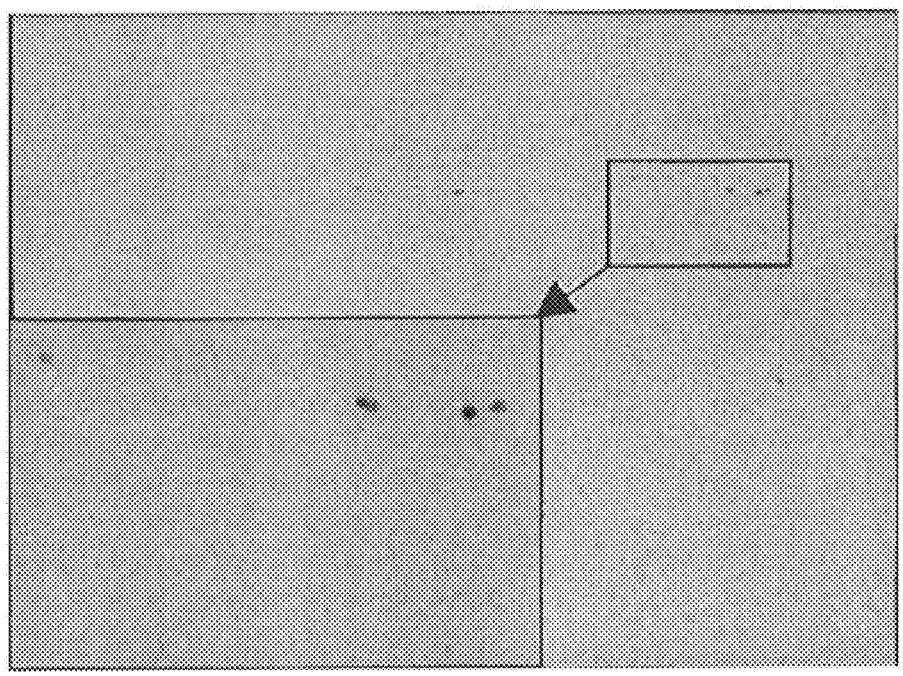
FIG. 13C is the fluorescence microscope image of FIG. 13B including a magnified portion thereof.
Figure 13D:
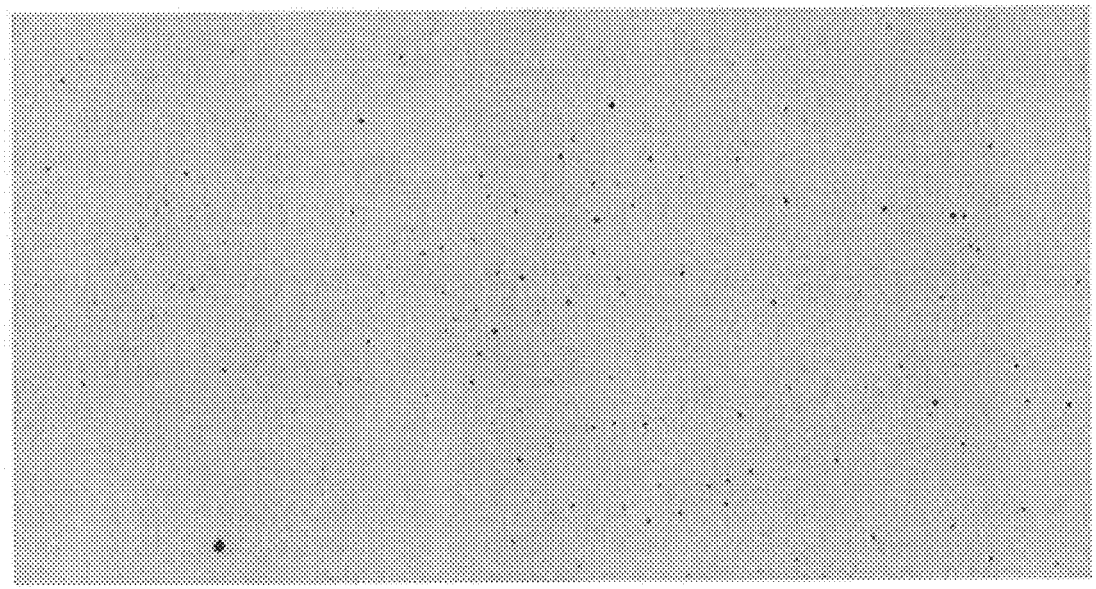
FIG. 13D is a fluorescence microscope image of captured MCF-7 cancer cells attached to antibodies disposed on a plurality of extensions (e.g. gold posts) having functionalized graphene oxide disposed thereon and in a microfluidic device similar to that illustrated in FIG. 2G.
Figure 13E:
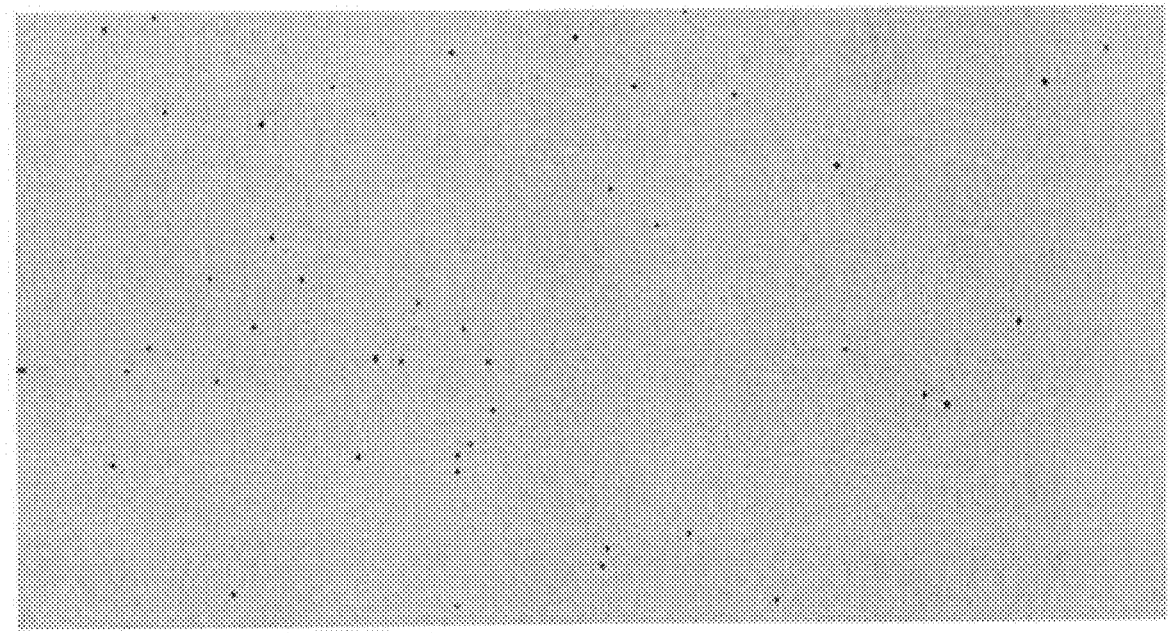
FIG. 13E is a second fluorescence microscope image of captured MCF-7 cancer cells attached to antibodies disposed on a plurality of extensions (e.g. gold posts) having functionalized graphene oxide disposed thereon and in a microfluidic device similar to that illustrated in FIG. 2G.
Figure 13F:
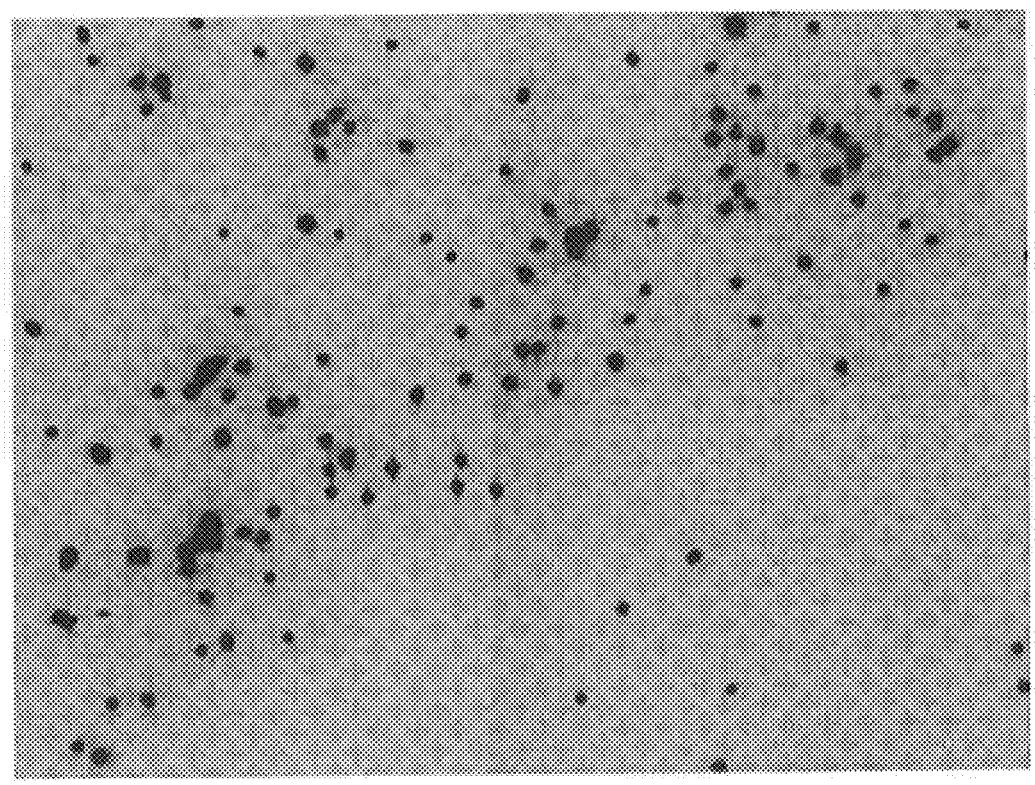
FIG. 13F is a third microscope image of captured MCF-7 cancer cells attached to antibodies disposed on a plurality of extensions (e.g. gold posts) having functionalized graphene oxide disposed thereon and in a microfluidic device similar to that illustrated in FIG. 2G.
Figure 13G:
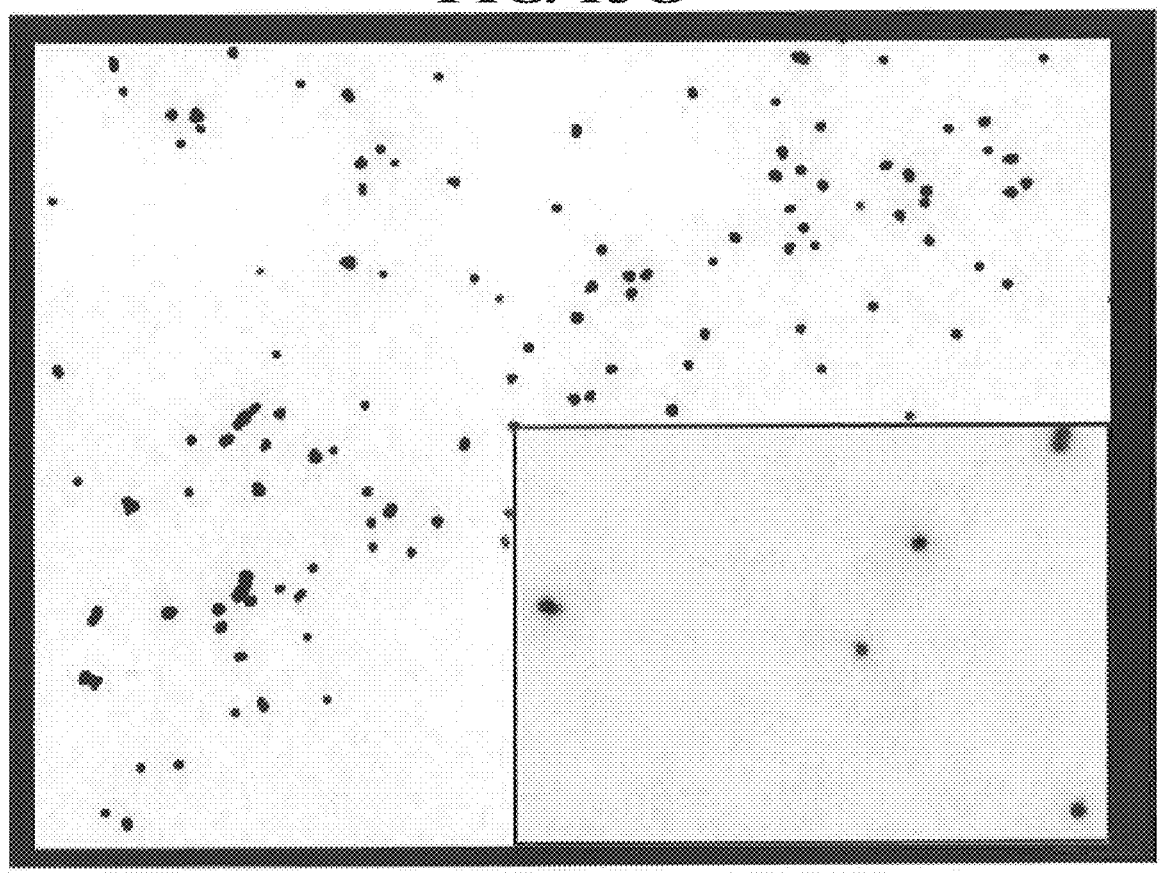
FIG. 13G is a fourth microscope image of captured MCF-7 cancer cells attached to antibodies disposed on a plurality of extensions (e.g. gold posts) having functionalized graphene oxide disposed thereon and in a microfluidic device similar to that illustrated in FIG. 2G.
Figure 14A:
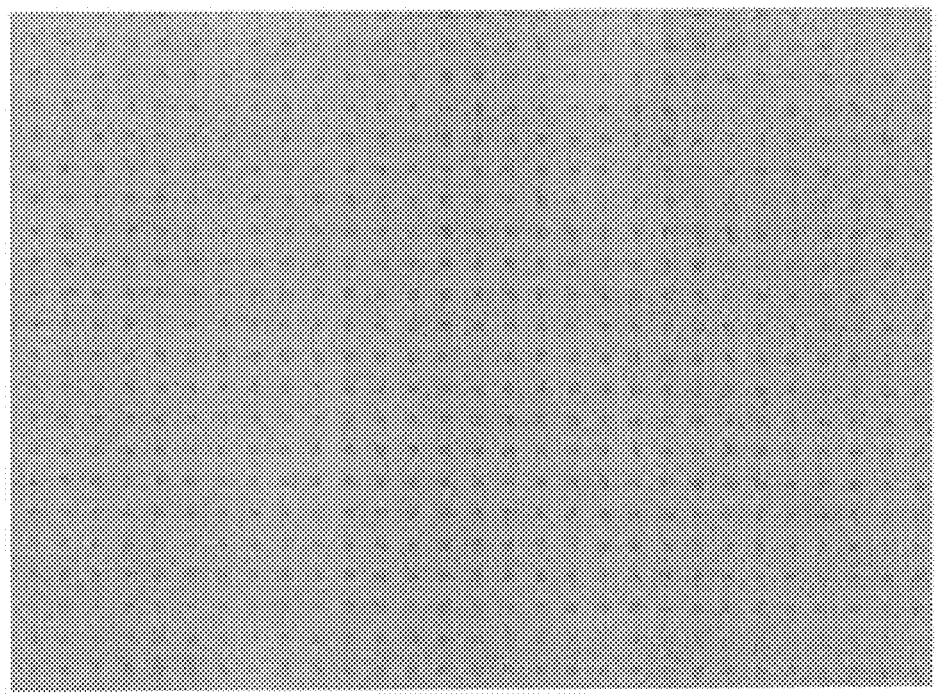
FIG. 14A is a fluorescence microscopy image of the extensions of a control microfluidic device described in the Examples wherein, at an exposure time of 1 second, no fluorescently labeled NeutrAvidin is seen.
Figure 14B:
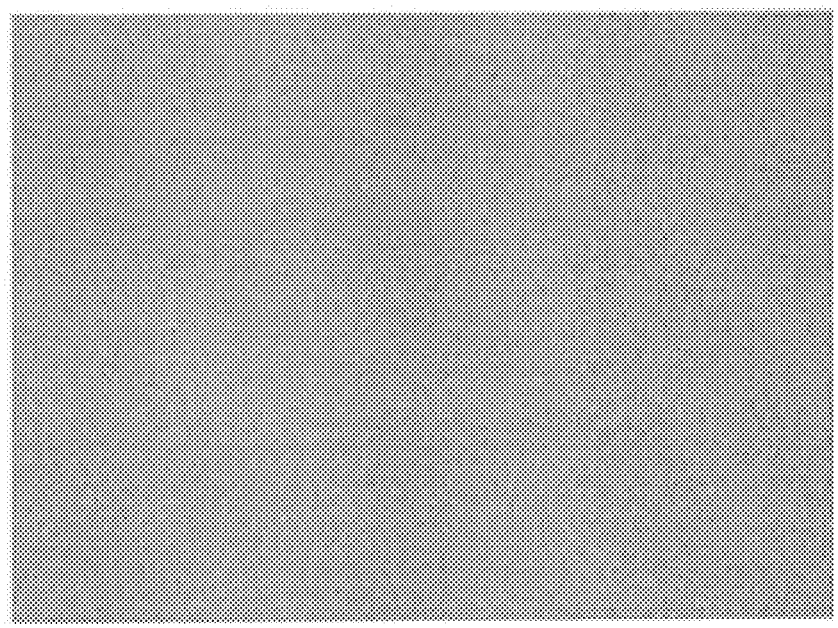
FIG. 14B is a fluorescence microscopy image of the extensions of a control microfluidic device described in the Examples wherein, at an exposure time of 200 ms, no fluorescently labeled NeutrAvidin is seen.

To confirm that the graphene oxide is functionalized, fluorescently labeled NeutrAvidin is utilized, see e.g. FIGS. 12A and 14A/B. Gold extensions including modified graphene oxide specifically show the presence of fluorescence, see e.g. FIG. 12A, where as negative controls without NeutrAvidin show no fluorescence at the same exposure condition, see e.g. FIG. 12B. This indicates high sensitivity and specificity, which is expected to exhibit high cell capture efficiency when employed to isolate viable cancer cells from whole blood samples.

To characterize the system/microfluidic device, MCF-7 cells are labeled with fluorescent cell tracker dye and spiked into buffer at various concentrations and flowed through the system/microfluidic device at a desired flow rate, e.g. 1,000 cell/mL, 1 mL/hr, as described below. Subsequently, the captured cells are counted.

Figure 18:
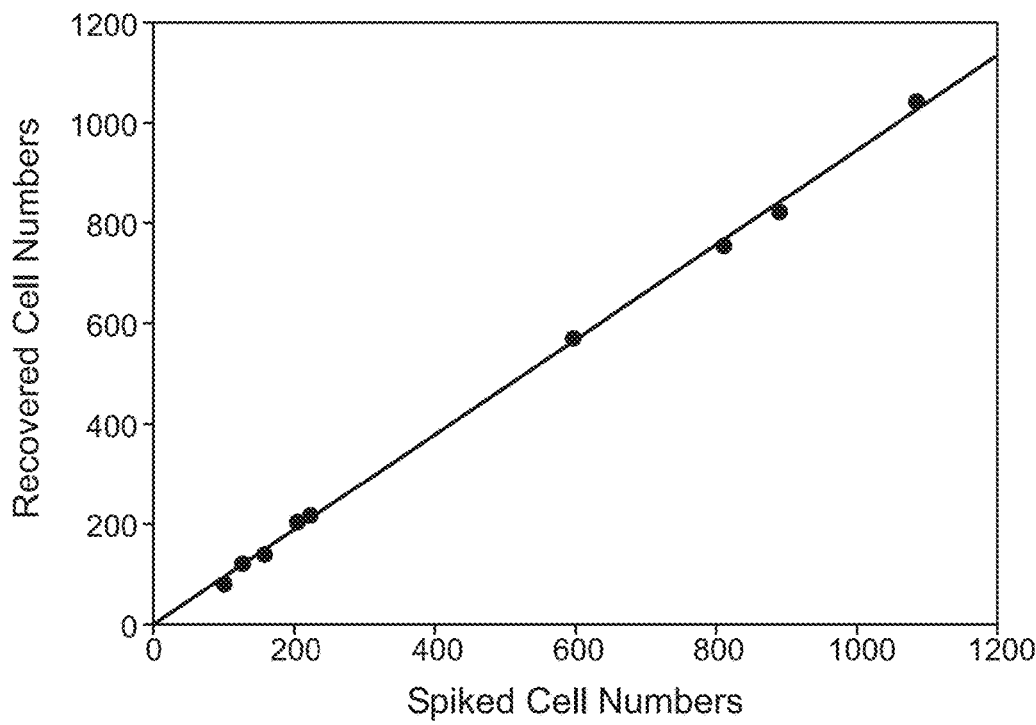
FIG. 18 is a bar graph showing the capture efficiency of various examples utilizing a microfluidic device similar to that illustrated in FIG. 2G using 100-1000 MCF-7 cells in a buffer solution at a flow rate of 1 mL/hr.
Figure 19:
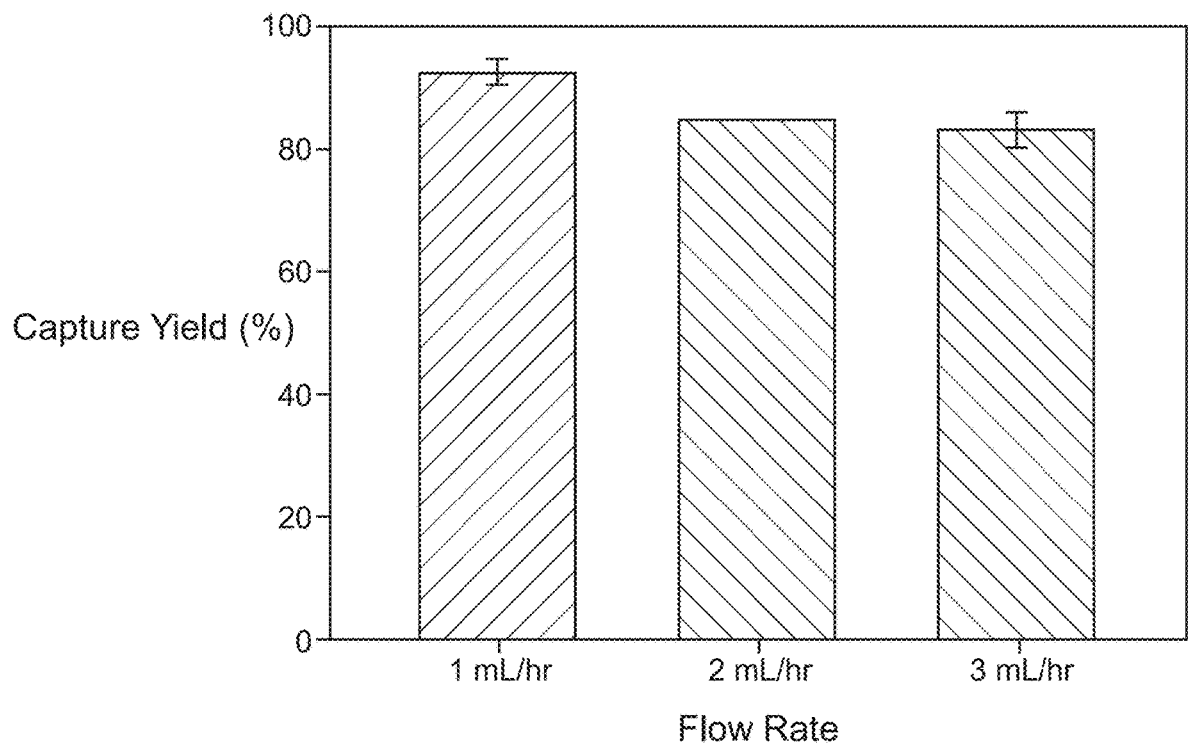
FIG. 19 is a bar graph showing the capture efficiency of various examples utilizing a microfluidic device similar to that illustrated in FIG. 2G using at different flow rates of 1 mL/hr, 2 mL/hr, 3 mL/hr.

More specifically, 100-1000 MCF-7 cells are spiked into the buffer solution. Samples of the spiked buffer solution are then flowed through the system/microfluidic device at various rates, see e.g. FIGS. 18 and 19. At a flow rate of 1-3 mL/hr, the capture yield is over 80%. At a 1 mL/hr flow rate, a very small difference of the capture yield between flow rates is observed, see e.g. FIGS. 13A-G.

Figure 21:
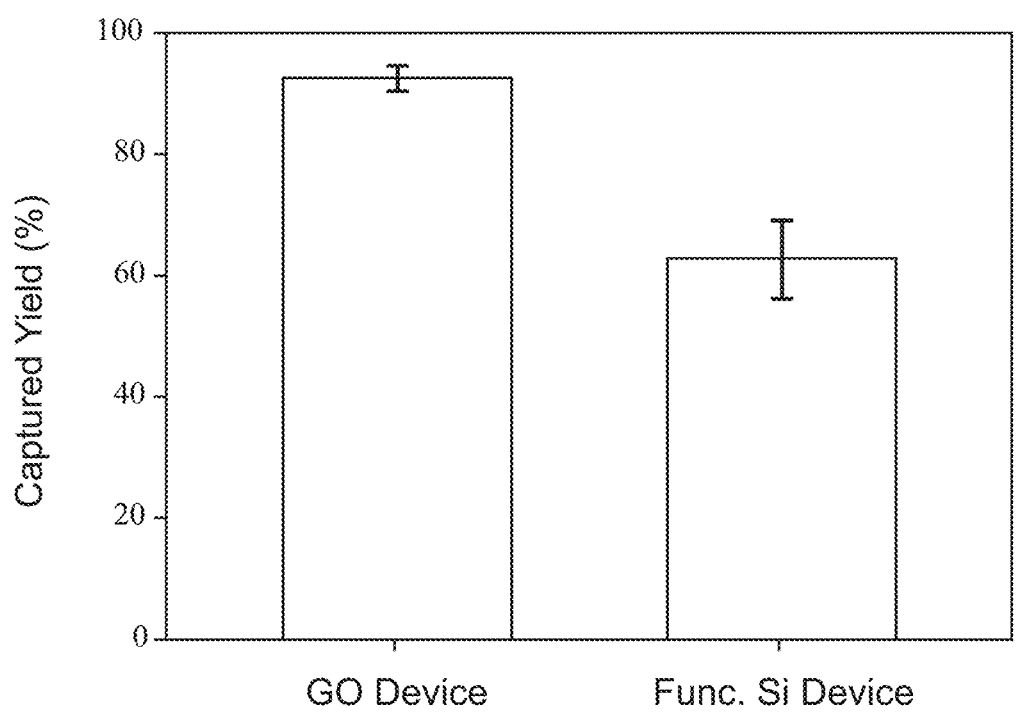
FIG. 21 is a bar graph showing the capture efficiency of various examples utilizing a microfluidic device similar to that illustrated in FIG. 2G using 1000 MCF-7 cells in buffer solution to compare a microfluidic device including graphene oxide to a comparative silicon device that is free of graphene oxide, as described in the examples.
Figure 22:
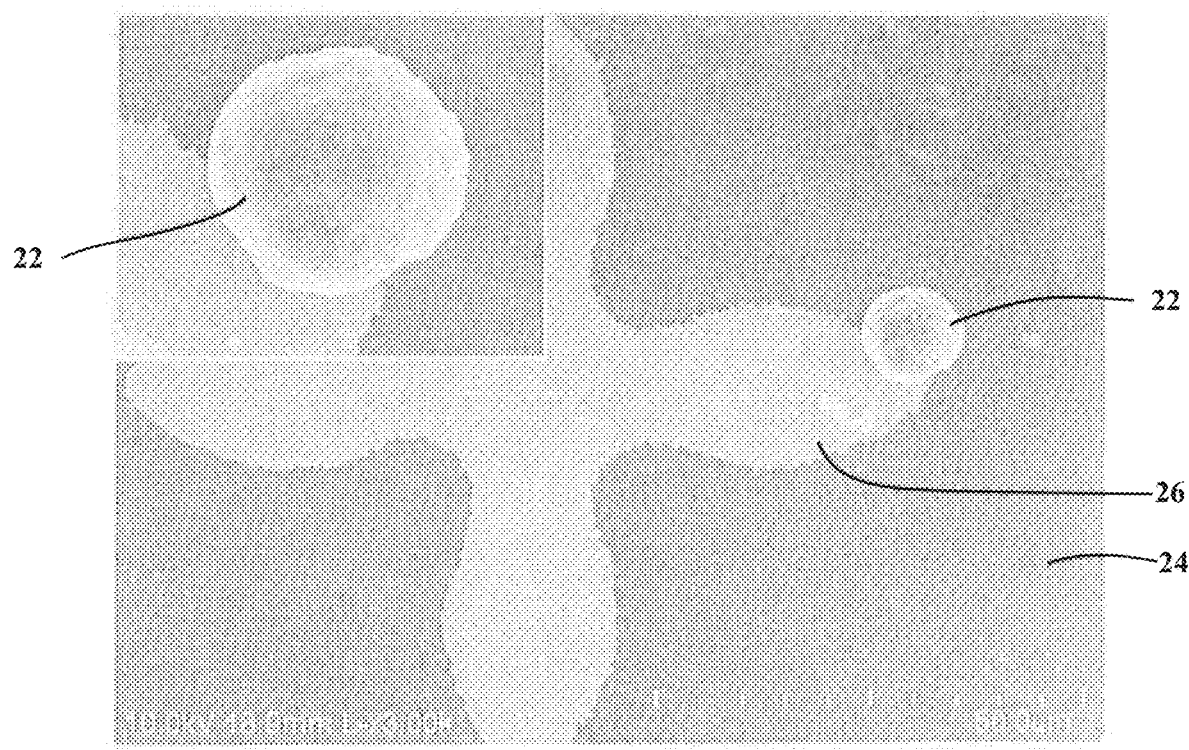
FIG. 22 is an additional SEM image of a rare cell bound to a plurality of extensions disposed in a leaf pattern and includes a magnified view of the rare cell.
Figure 23:
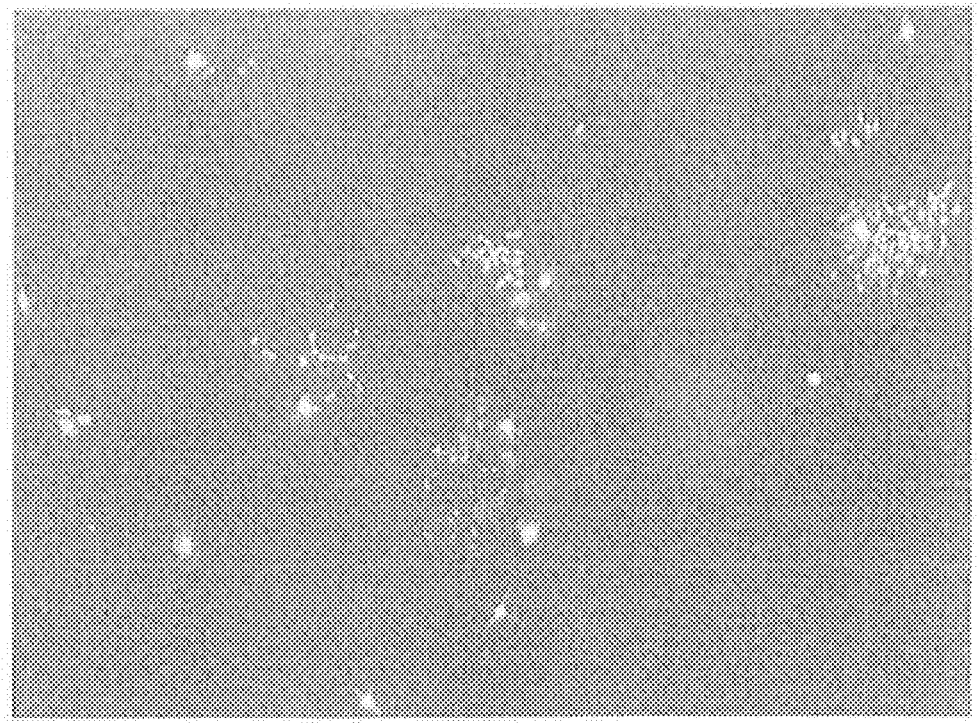
FIG. 23 is a fluorescence microscope image of captured and 6-days-grown MCF-7 cells bound to a plurality of extensions.
Figure 24:
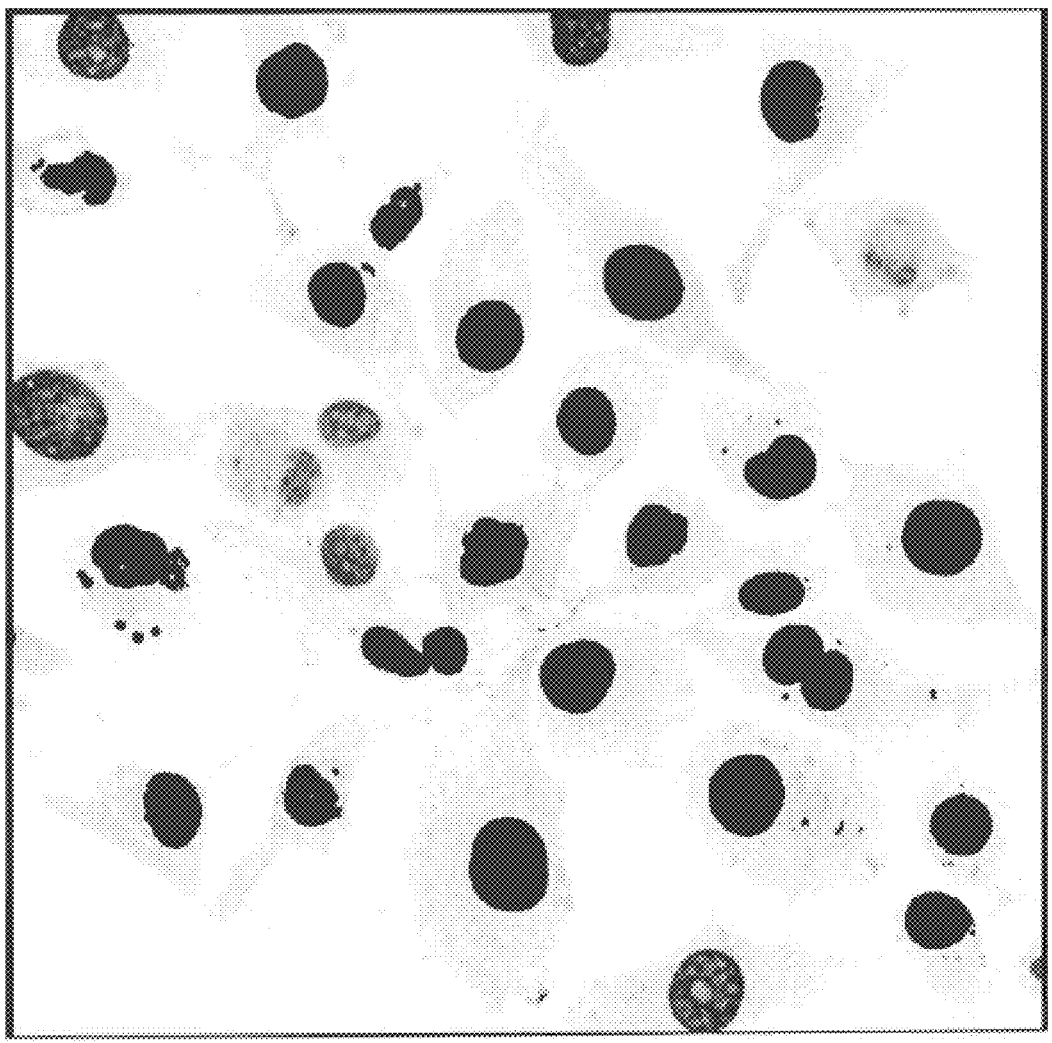
FIG. 24 is a second fluorescence microscope image of captured and 6-days-grown MCF-7 cells bound to a plurality of extensions to identify proliferating cells.

A comparative silicon device that does not include the extensions or the functionalized graphene oxide is also produced. More specifically, a silicon substrate is functionalized with silane, GMBS, and NeutrAvidin using the same conditions as are used to form the example of the system/microfluidic device of this disclosure. Samples of the buffer solution are then passed over this comparative silicon device to determine how many cells are captured. The results of this experiment are set forth in FIG. 21.

These results demonstrate that use of the graphene, oxide and the extensions increase the capture efficiency likely due to enhanced surface area and morphology. When MCF-7 cells are flowed through the instant system/microfluidic device, the trajectory of cells tends to be a parabola. Along with the trajectory, most of cells are captured on extensions, see e.g. FIGS. 13A-G.

Figure 20:
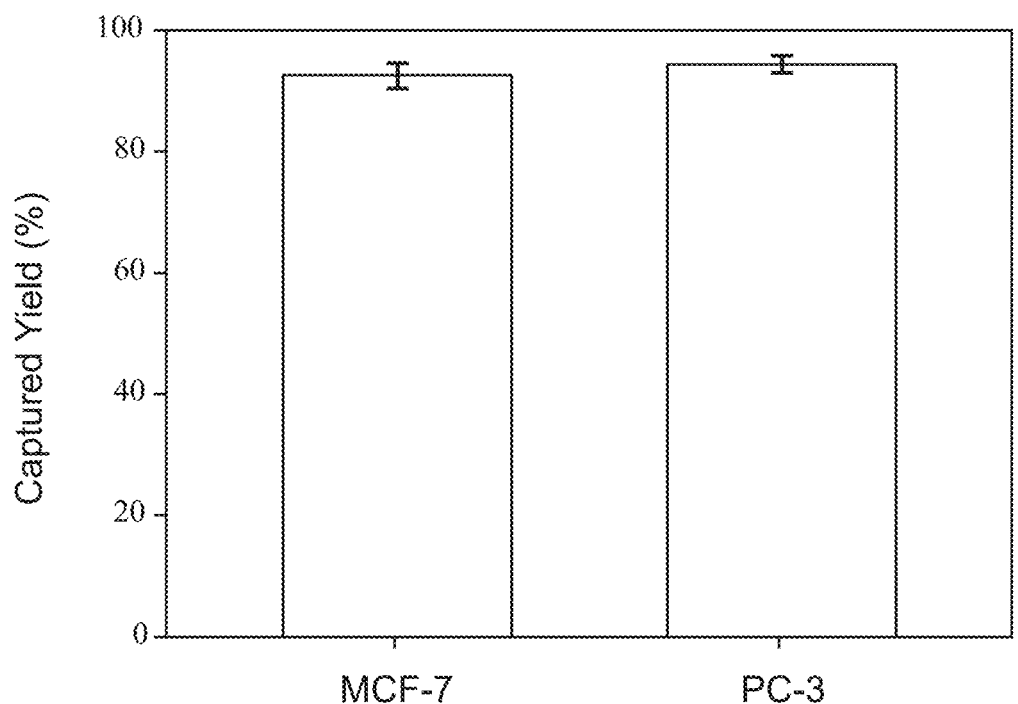
FIG. 20 is a bar graph showing the capture efficiency of various examples utilizing a microfluidic device similar to that illustrated in FIG. 2G using 1000 MCF-7 cells and PC-3 cells in a buffer solution to compare different cell lines' capture efficiency.

To further investigate the capture efficiency using blood samples, a low number of MCF-7 cells (3-5 cells, 10-20 cells, 100 cells, see e.g. FIG. 17A) are spiked into 1 mL of whole blood (FIG. 20). Cells are diluted in serum-free medium at a concentration of $1\times10^5$ cells/mL. 1 µL of cell suspension added to a 96-well plate. The transferred cells are counted under a microscope, immediately transferred by pipette and added to 1 mL of whole blood. Remaining cells not transferred into the whole blood are also counted to verify the accuracy of the transfer. By subtracting the number of remaining cells from the original count, an actual number of cells spiked into blood is estimated. These steps occur at room temperature.

The average recovery rates of the 10-20 cell spike and the 100 cell spike are 91% and 87%, respectively. The average recovery rate of the 3-5 cell spike is 59%. Two examples that include 6 cells exhibit a 100%, recovery rate Microfabrication of the Microfluidic Device:

The aforementioned system/microfluidic device is fabricated using a series of 4 inch N-type silicon wafers as substrates. These wafers are cleaned by RCA cleaning. A 3000 ø thermal oxide is grown by a wet oxidation process. Subsequently, Cr and Au (100 ø/1000 ø) layers are deposited on the silicon wafer by e-beam evaporation to form extensions. Then, a photoresist is coated by automatic spinner and patterned by mask aligner (MA-6, Karl Suss). For patterning the Au and Cr extensions, the wafers are placed in Au/Cr etch solution. The photoresist is then removed by acetone and rinsed by isopropyl alcohol (IPA).

Subsequently, an already prepared PDMS layer with a chamber having a 50 mm length, an 18 mm width, and a 50 µm height, is bonded onto the silicon wafer having the pattern of gold extensions disposed thereon. The PDMS layer is fabricated using standard SU-8 mold process. The silicon wafer and the PDMS layer are bonded by corona discharge treatment.

Functionalization and Nano-Assembly of Graphene Oxide:

10 mg of graphene oxide (Cheap Tubes Inc.) powder is also prepared to form a single layer graphene oxide (SLGO) which is then treated with a modified Hummer's method as described in Hummers, W. S. & Offeman, R. E. Preparation of Graphitic Oxide. *Journal of the American Chemical Society* 80, 1339 (1958). 10 mL N,N-dimethylformamide (DMF) and 300 μL tetrabutylammonium (TBA) hydroxide (40% in water) are then added thereto to form a graphene oxide suspension, see e.g. FIG. 16A. Using a tip sonicator, the graphene oxide suspension is then ultrasonicated for 30 min. To avoid an increased temperature during the sonication, a temperature sensor is monitored and the suspension tube is immersed in an ice bath. The graphene oxide suspension is reserved for 3 days at room temperature.

4 mL of the supernatant is then extracted and 15 mg of phospholipids-polyethylene-glyco-amine (PL-PEG-NH2, NOF Co.) is dissolved therein, bath sonicated for about 1 hour, and subsequently centrifuged at 12,000 rpm for 3 min. The supernatant is collected and stored at 4° C. The supernatant includes PEG functionalized graphene oxide. The silicon wafer is then dipped into the functionalized supernatant for 10 min and washed with DI water and IPA, see e.g. FIGS. 11A/B. The prepared PDMS layer with the chamber, as described above, is then bonded to the silicon wafer using corona discharge treatment.

A GMBS solution is then flowed through the chamber at 20 μL/min using a syringe pump (Harvard Apparatus). After 30 minutes of incubation, the chamber is washed with ethanol at 100 μL/min. Subsequently, 50 μg/mL NeutrAvidin is prepared and flowed through the chamber at 20 μL/min. After 1 hour incubation, the chamber is flushed with phosphate buffered solution (PBS) at 100 μL/min to remove excess NeutrAvidin. Finally, biotinylated EpCAM antibody at a concentration of 20 μg/mL in PBS with 1% (w/v) BSA is flowed through the chamber for 10 minutes at 20 μL/min. After 1 hour incubation, PBS is flowed through the chamber to wash, and then, bovine serum albumin (BSA) is added to a 1× PBS solution and flowed through the chamber at 100 μL/min for 5 minutes. After flowing BSA solution, the chamber incubates for 30 minutes.

Cell Culture and Labeling:

Tissue culture reagents are purchased from GIBCO Invitrogen Corporation/Life Technologies Life Sciences unless otherwise specified. MCF-7 and PC-3 cells are cultured in DMEM and DMEM/F12 medium including 10% fetal bovine serum and 1% penicillin-streptomycin solution. When cells reach more than 90% confluence, the medium is replaced with a fresh medium. A green cell tracker dye (Invitrogen, CellTracker Green CMFDA, C7025) for labeling cells is used to perform rare cell capture efficiency calculations.

Blood Specimen Collection:

Blood samples are drawn from patients with tumors and healthy donors after obtaining informed consent under an IRB-approved protocol. All specimens are collected into EDTA tubes and are processed within 3 hours.

Cytokeratin and CD45 Staining:

After incubating for 30 minutes, 1 ml blood samples including non-labeled cells are flowed through the chamber at a rate of 1 ml/hr to capture cells. Subsequently, the captured cells are washed with PBS, fixed with 4% paraformaldehyde (PFA), permeabilized with 0.2% Triton-X and incubated for 30 minutes followed by washing with PBS. The chamber is then incubated for 30 minutes with 1 mL of blocking buffer including 2% normal goat serum and 3% BSA. Anti-cytokeratin (BD Biosciences) and anti-CD45 (BD Biosciences) are diluted at 1:50 and 1:10 in 1% BSA, respectively, see e.g. FIG. 17A. Antibodies are then flowed through the chamber for 20 minutes at 50 μL/min and incubated for 1 hour. After absorption of the primary antibody, the chamber is washed with PBS. The anti-cytokeratin is probed with AlexaFluor488 IgG2a FITC (Invitrogen) and the anti-CD45 is probed with AlexaFluor546 IgG1 (Invitrogen). The secondary antibodies are diluted in 1% BSA at a 1:1000 ratio, flowed through the chamber for 20 minutes at 50 μL/min, incubated for 1 hour and then washed with PBS.

To stain nuclei of captured cells, DAPI (1:1000 dilution in PBS) is flowed through the chamber for 20 minutes at 50 μL/min and the chamber is incubated for 15 minutes and washed with PBS.

Cell Treatment with EdU

To measure cells' ability to proliferate, Click-iT EdU Imaging Kit (Invitrogen, C10340) is used. After capturing cells, the chamber is washed with PBS and 1 μM EdU is added to the chamber. The chamber is incubated overnight, washed with PBS, and then the cells are fixated using 4% PFA. After 15 min incubation, the chamber is washed with 3% BSA twice, followed by cell permeabilization with 0.2% Triton X-100 in PBS and incubated for 20 minutes. The chamber is washed with 3% BSA twice and 0.5 mL of Click-iT EdU buffer additive is added, followed by incubation for 30 minutes and washing with 3% BSA. For nucleus staining, 1 mL of 1× Hoechst 33342 solution is added and cells in the chamber are incubated for 30 minutes and washed with 1 mL of PBS.

Additional Examples

Various solutions of solvent and functionalized graphene oxide sheets are formulated and exposed to various metals that are representative of various extensions of the system of this disclosure. The metals are then analyzed to determine whether any of the metals are able to adsorb the functionalized graphene sheets. The details of these analyses are set forth immediately below in Table 1. The results associated with these evaluations are determined using scanning electron microscopy and/or atomic force microscopy.

TABLE 1

| Metal | Functionalized Graphene Oxide Sheet | Solvent | Result |
|---|---|---|---|
| Au | TBA, PL-PEG-amine | $H_2O$/DMF (3:100) | Positive |
| Au | TBA, PL-mPEG | $H_2O$/DMF (3:100) | Positive |
| Au | PL-PEG-amine | $H_2O$/DMF (3:100) | Negative |
| Au | TBA, PL-PEG-amine | Pure DMF | Negative |
| Au | TBA, PL-PEG-amine, acidified by $HNO_3$ | $H_2O$/DMF (3:100) | Negative |
| Al | TBA, PL-PEG-amine | $H_2O$/DMF (3:100) | Negative |
| Ti | TBA, PL-PEG-amine | $H_2O$/DMF (3:100) | Partially Positive |
| Co | TBA, PL-PEG-amine | $H_2O$/DMF (3:100) | Partially Positive |
| Pd | TBA, PL-PEG-amine | $H_2O$/DMF (3:100) | Partially Positive |

Additional non-limiting examples of graphene oxide sheets and non-limiting examples of this disclosure are also formed. In a first example, single layer graphene oxide (SLGO) powder is used and subjected to a modified hummer's method as described in W. Hummers, and R. Offeman, "Preparation of graphitic oxide," *Journal of the American Chemical Society*, vol. 80, pp. 1339, Mar. 1958, More specifically, 10 mg of graphene oxide powder is prepared. Then, 10 mL DMF and 300 µL TBA hydroxide (40%) is added thereto to form a solution. Using a tip sonicator, the solution is sonicated for approximately 10 min at an amplitude of 50 with a 2 minute cool down. A supernatant is then removed and reserved for 2-3 days. Approximately 4 mL of the supernatant is then extracted and approximately 15 mg of PL-PEG-NH2 is dissolved therein. This solution is then bath sonicated for about 1 hour and subsequently centrifuged at 12,000 rpm for about 3 min. After centrifugation, the supernatant is collected at stored at about 4° C. The supernatant includes polyethylene glycol (PEG) functionalized graphene oxide.

Figure 15A:
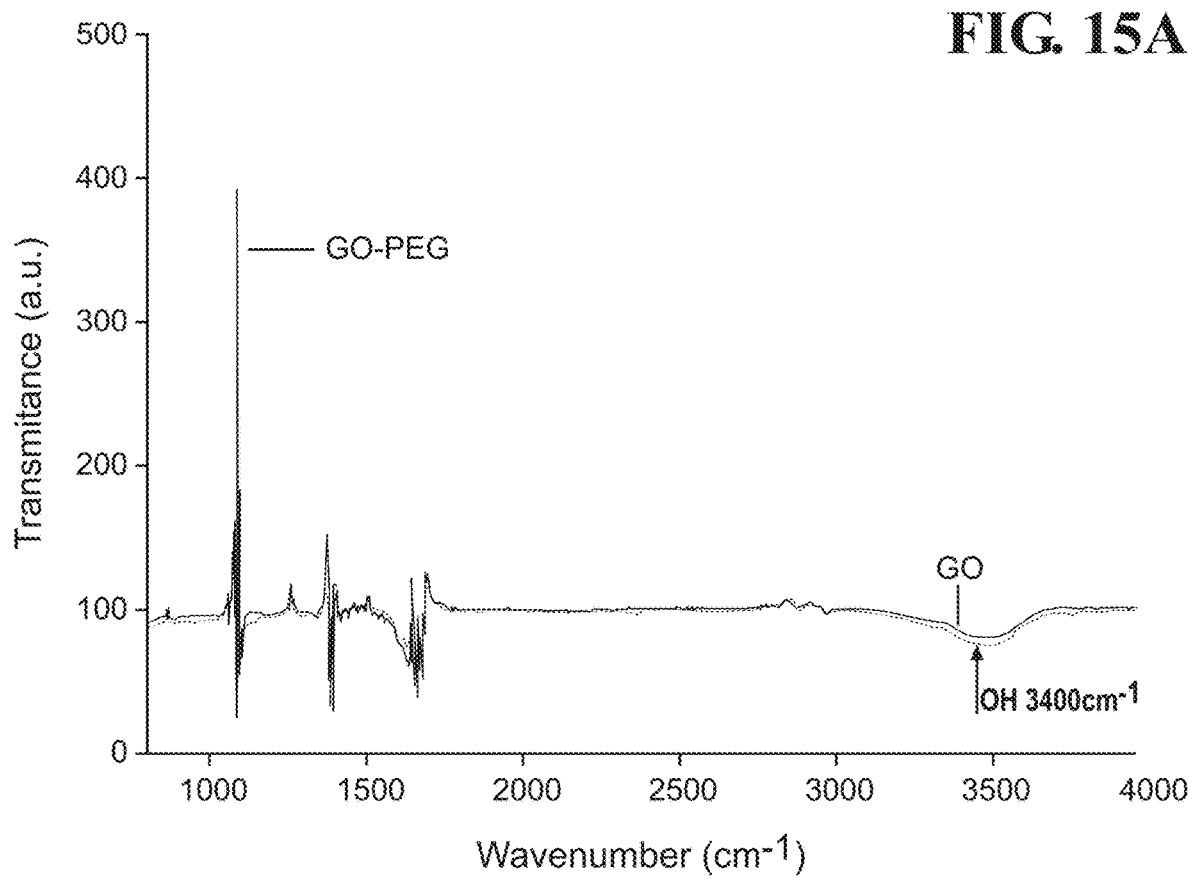
FIG. 15A is an FT-IR spectrum of a sample of graphene oxide used in the Examples overlaid with an FT-IR spectrum of a sample of the PEG-functionalized graphene oxide formed in the Examples.
Figure 15B:
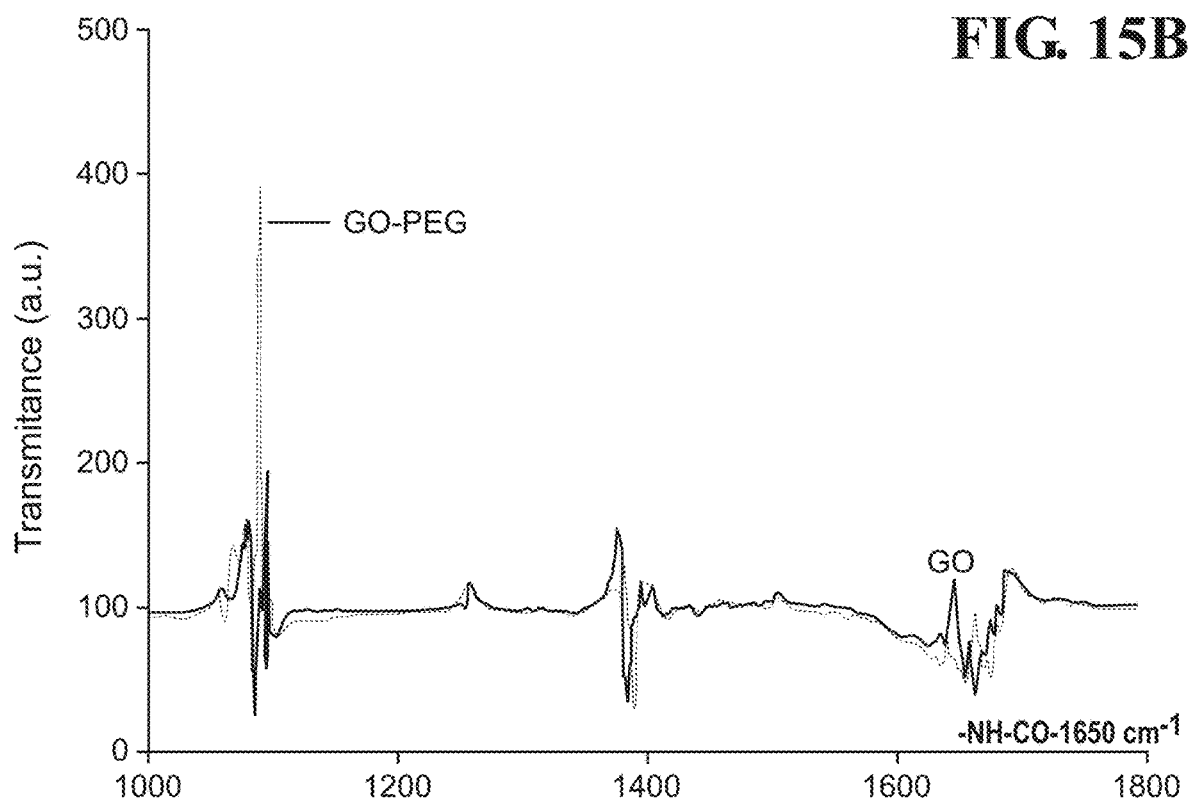
FIG. 15B is a magnified view of the FT-IR spectra of FIG. 15A from 1000 to 1800 cm$^{-1}$.

To verify the functionalization of the graphene oxide with the polyethylene glycol, the supernatant is analyzed using FT-IR spectroscopy. The spectra generated are then compared to similar FT-IR spectra of non-functionalized graphene oxide. The results of these FT-IR analyses are set forth in FIGS. 15A and B. FIG. 15A shows that, at 3400 $cm^{-1}$, there is a graphene oxide-related peak clearly shown. FIG. 15B shows that, at 1650 $cm^-$, the a peak for functionalized graphene oxide disappears which is indicative of an NH—CO stretching vibration and exchange of an amine group with polyethylene glycol.

Figure 5:
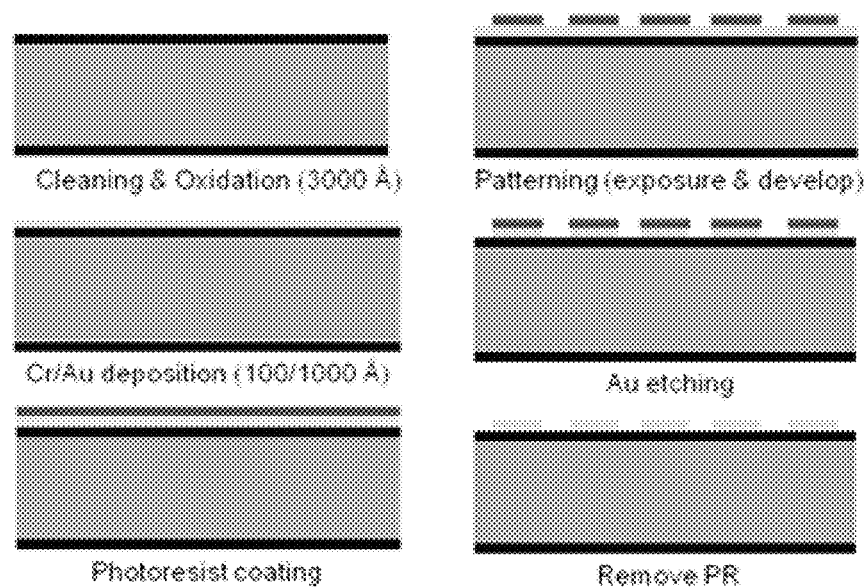
FIG. 5 is a schematic diagram of a series of method steps, one or more of which may be utilized to form graphene oxide.
Figure 6A:
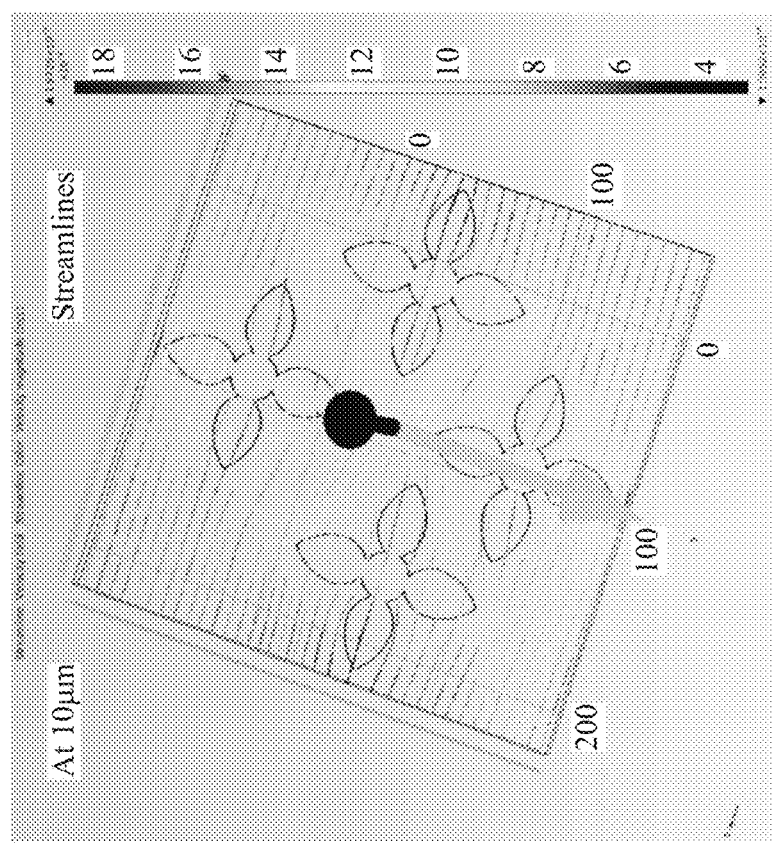
FIG. 6A illustrates simulation results of velocity fields and streamlines of leaf patterns at 10 μm height of a simulated fluid channel/chamber of a microfluidic device.
Figure 6A:
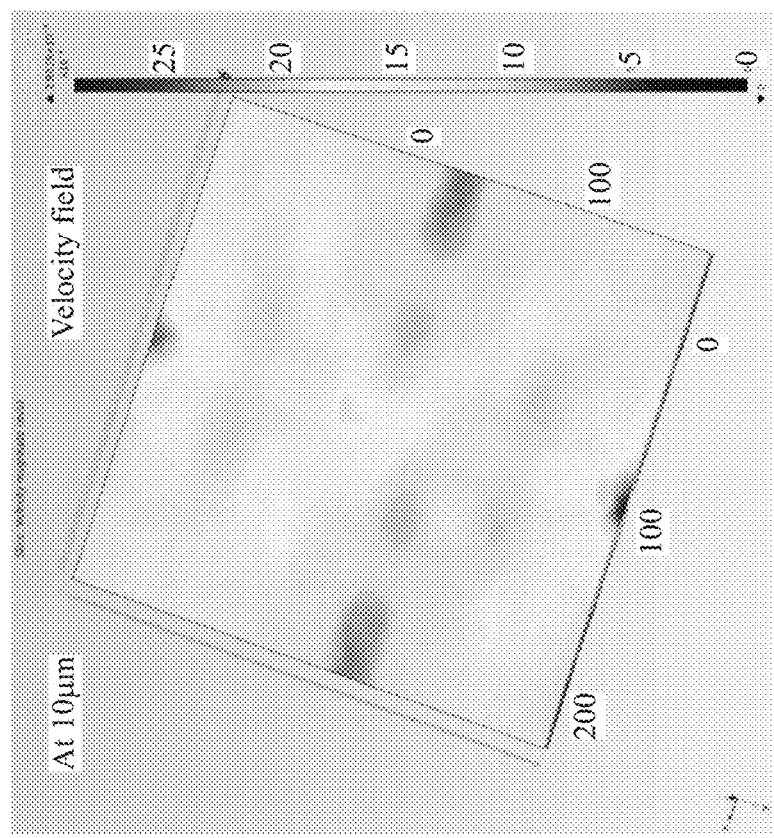
Figure 6B:
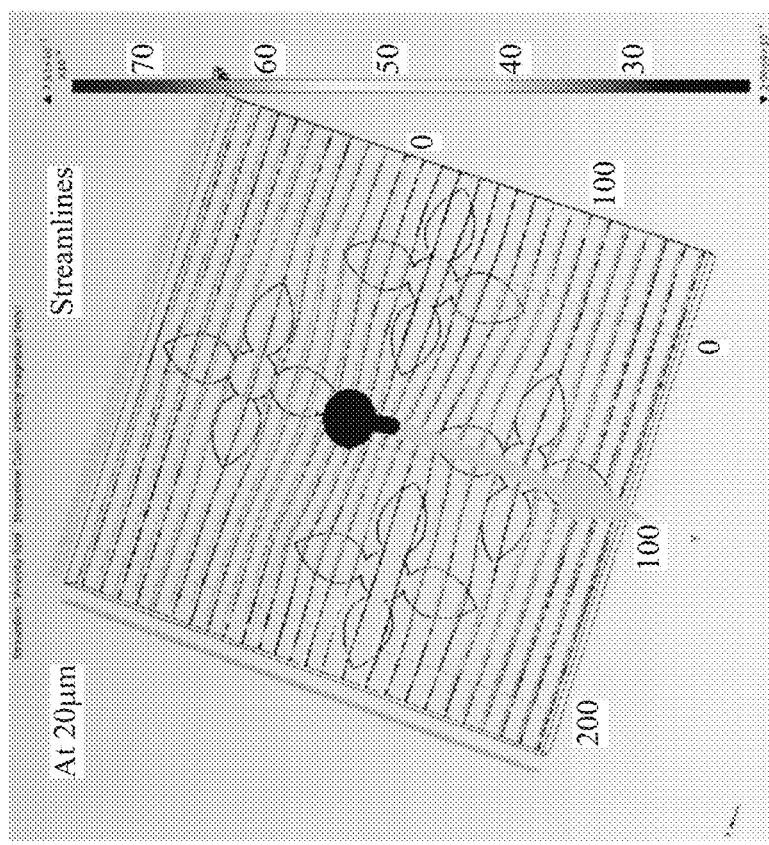
FIG. 6B illustrates simulation results of velocity fields and streamlines of leaf patterns at 20 μm height of a simulated fluid channel/chamber of a microfluidic device.
Figure 6B:
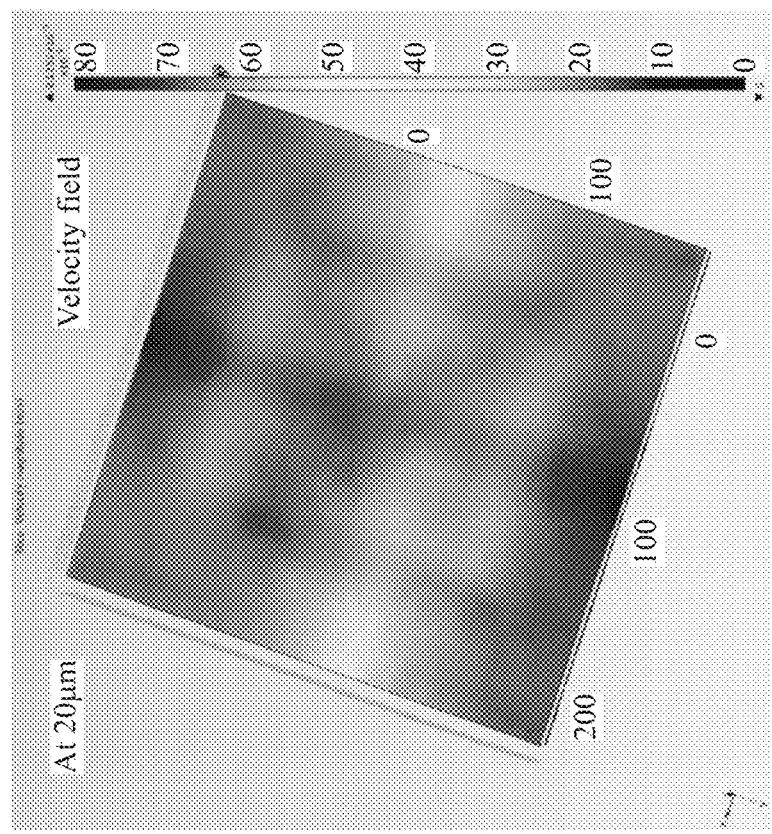
Figure 6C:
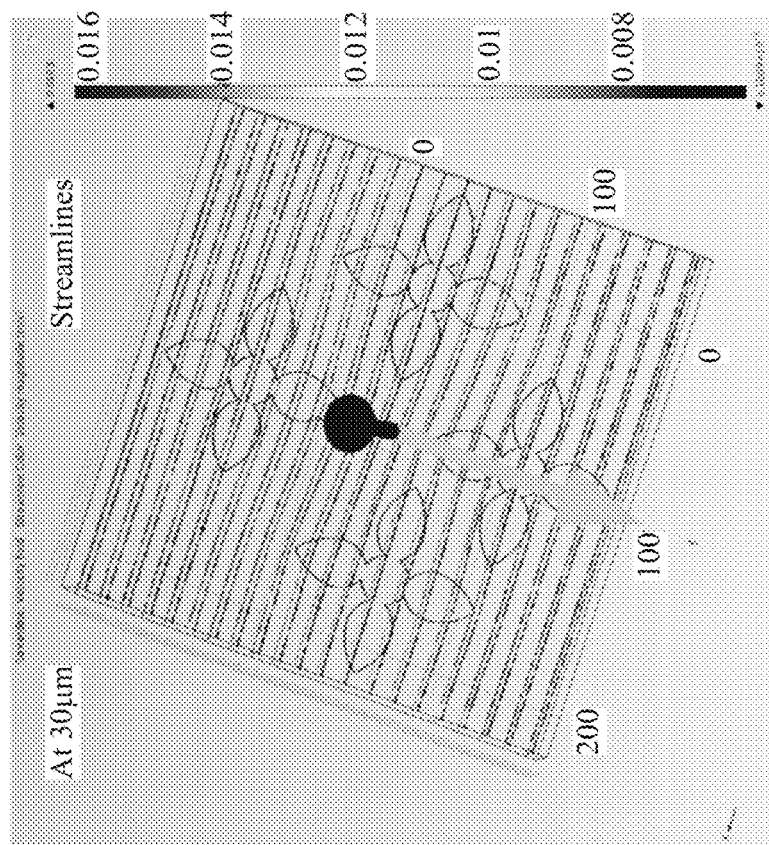
FIG. 6C illustrates simulation results of velocity fields and streamlines of leaf patterns at 30 μm height of a simulated fluid channel/chamber of a microfluidic device.
Figure 6C:
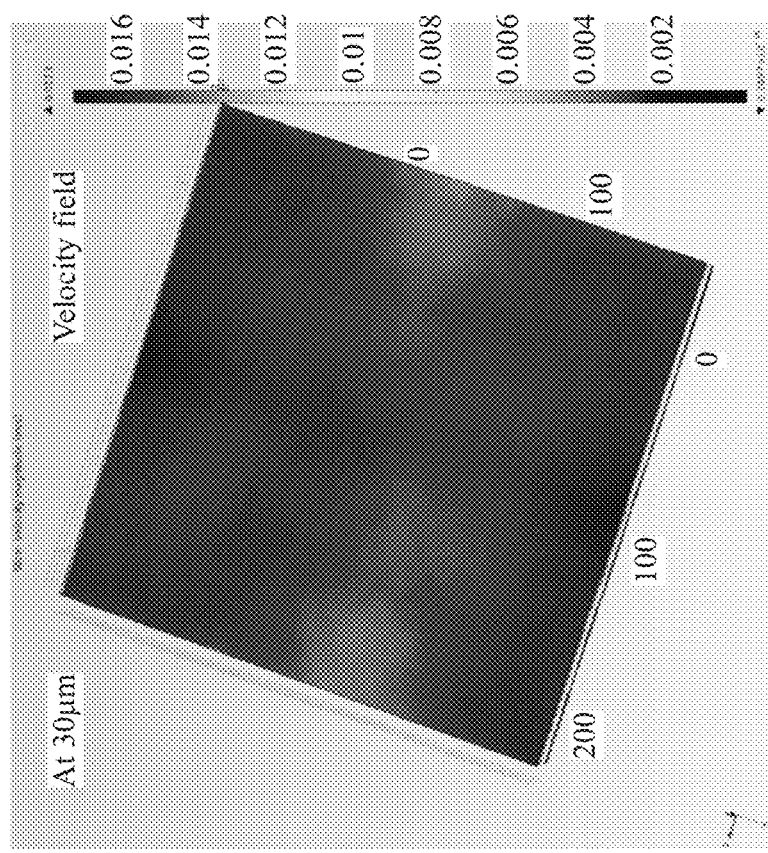
Figure 7A:
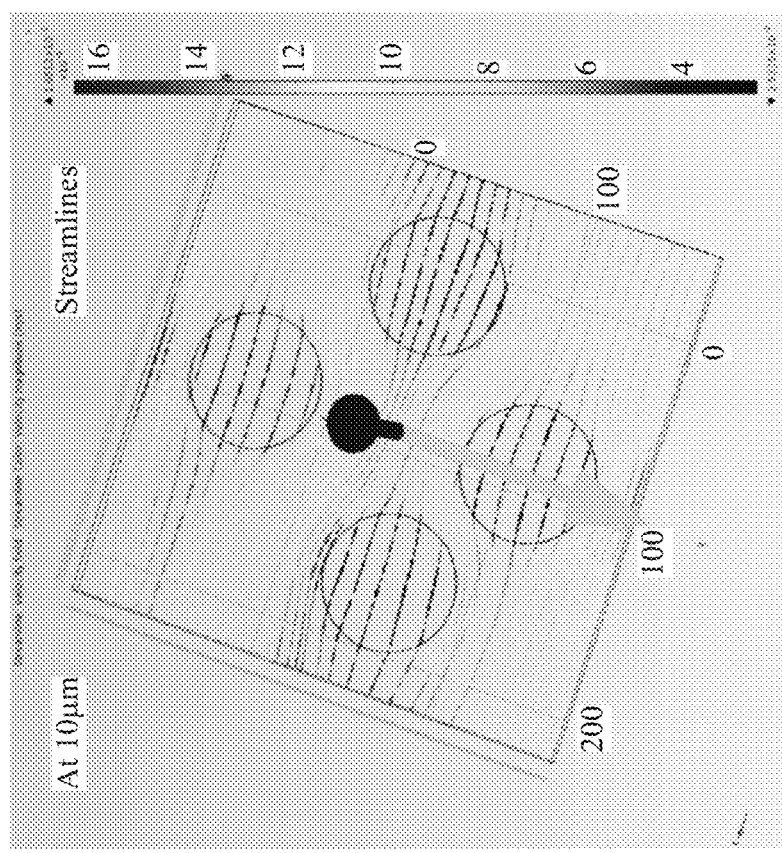
FIG. 7A illustrates simulation results of velocity fields and streamlines of circular patterns at 10 μm height of a simulated fluid channel/chamber of a microfluidic device.
Figure 7A:
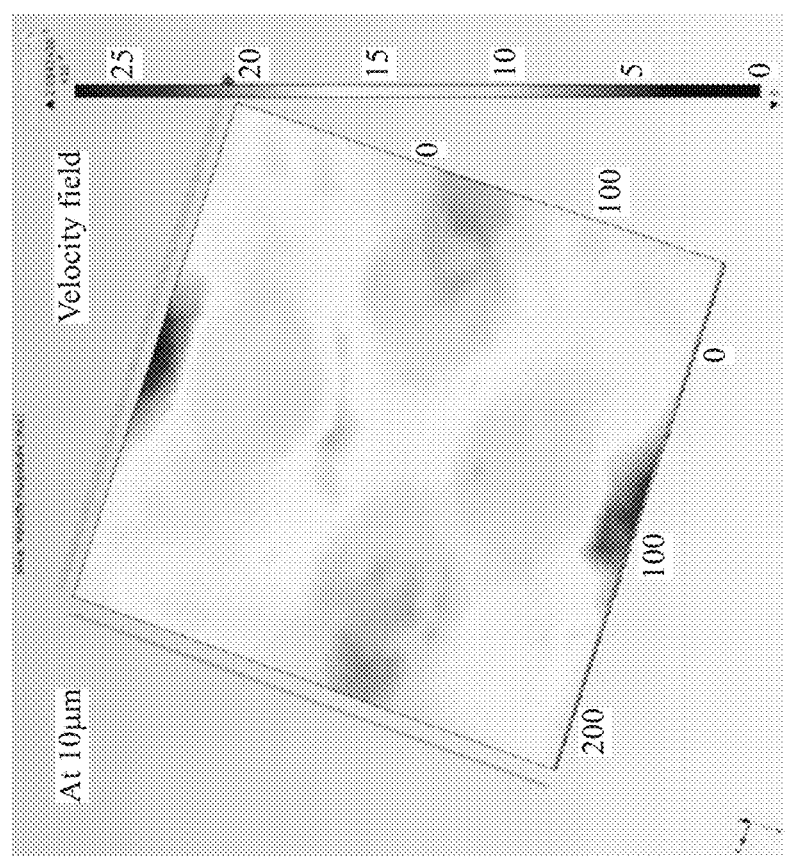
Figure 7B:
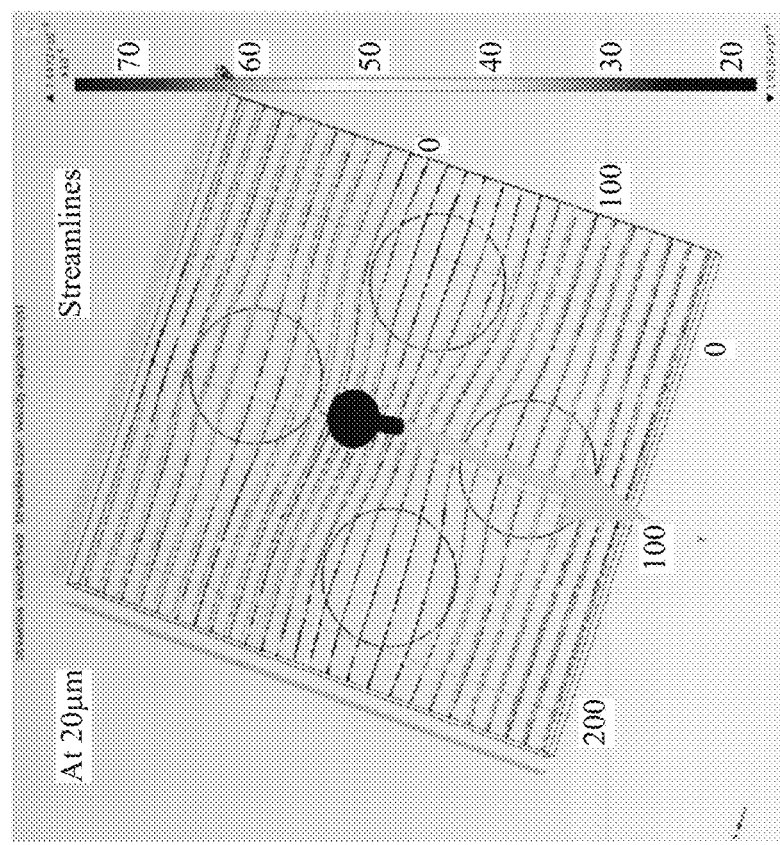
FIG. 7B illustrates simulation results of velocity fields and streamlines of circular patterns at 20 μm height of a simulated fluid channel/chamber of a microfluidic device.
Figure 7B:
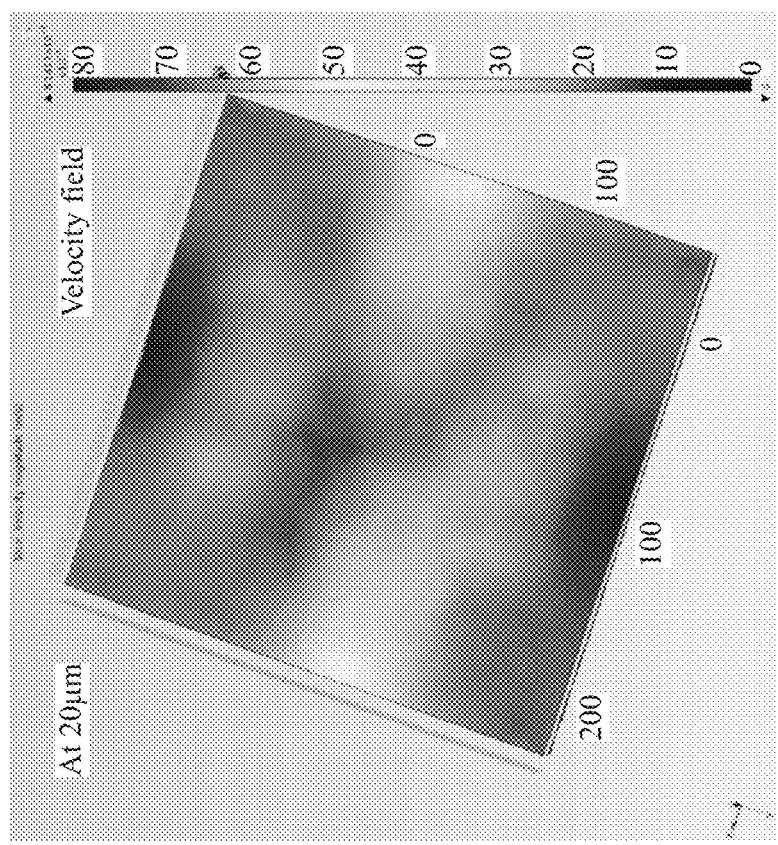
Figure 7C:
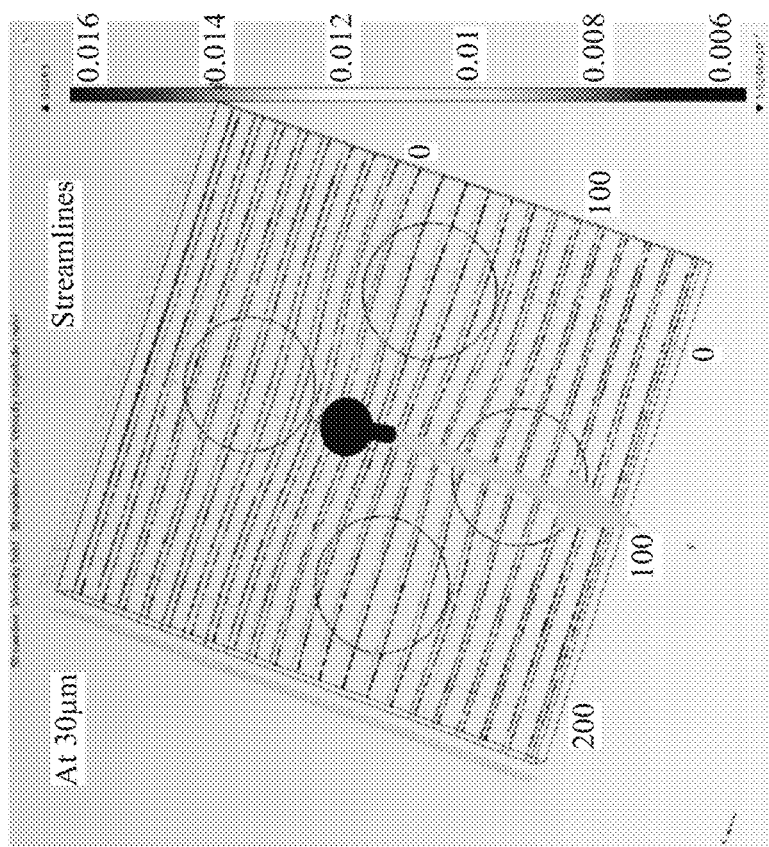
FIG. 7C illustrates simulation results of velocity fields and streamlines of circular patterns at 30 μm height of a simulated fluid channel/chamber of a microfluidic device.
Figure 7C:
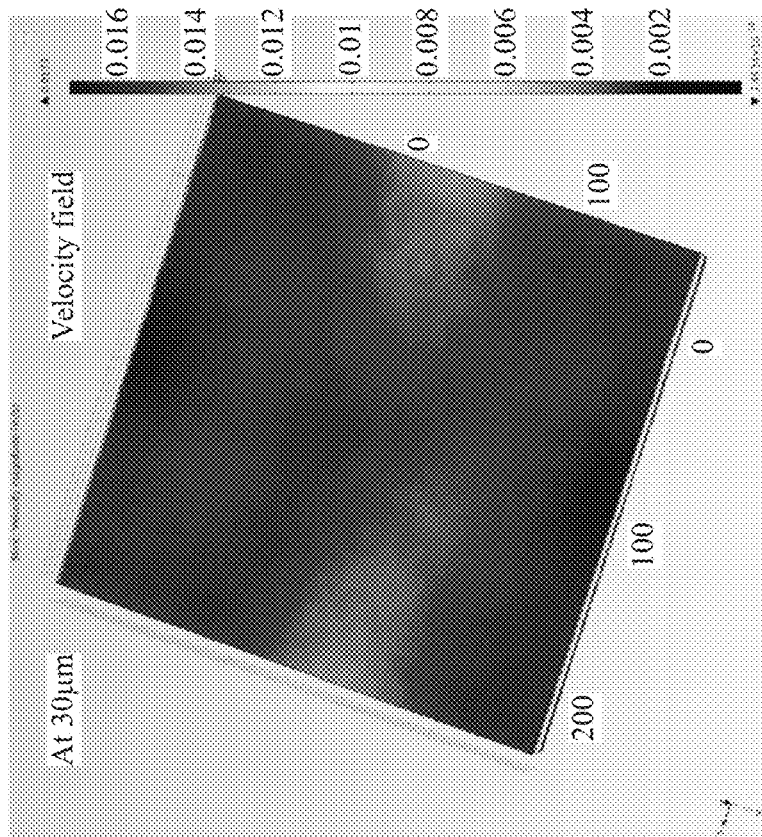

A microfluidic device, similar to the microfluidic device set forth in FIG. 1, is also formed. More specifically, the microfluidic device includes a silicon substrate, an $SiO_2$ supplemental layer disposed on and in direct contact with the silicon substrate, an additional PDMS supplemental layer, and gold nanoposts (as the extensions of this disclosure). The PDMS supplemental layer is fabricated using a standard SU-8 mold. The silicon substrate and the PDMS supplemental layer are bonded by oxygen plasma treatment. FIG. 5 shows steps in the fabrication process of this particular non-limiting microfluidic device. More specifically, an N-type (100) silicon wafer is cleaned by RCA cleaning. A silicon dioxide layer (3000 ø) is then grown by wet oxidation processing in a furnace at about 1100° C. Cr and Au (100 ø/1000 ø) layers are then deposited by e-beam evaporation. Photoresist (SPR 330) is then coated by an automatic spinner (ACS 200) and patterned by a mask aligner (MA-6). The exposure time is about 12 sec and the developing time is about 25 sec for these processes. For patterning the Au and Cr, the wafer is placed in an Au etch solution for about 25 sec and into a Cr etch solution for about 25 sec. The photoresist is then removed by acetone and rinsed by IPA and the device is exposed to oxygen plasma for about 3 minutes at 100 W.

Figure 10A:
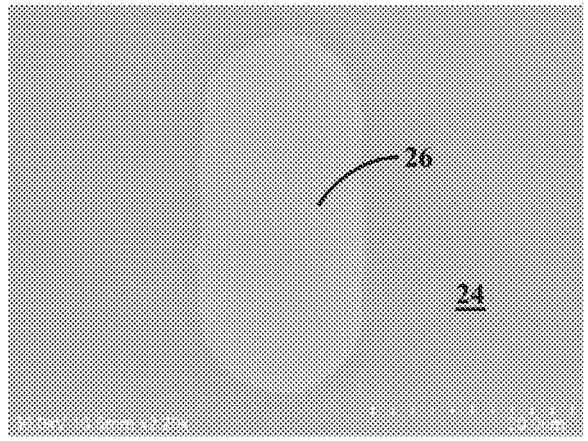
FIG. 10A is an SEM image of an extension (e.g. gold nanopost) that is not washed with TBA Hydroxide and does not include any visible graphene oxide sheets disposed thereon.
Figure 10B:
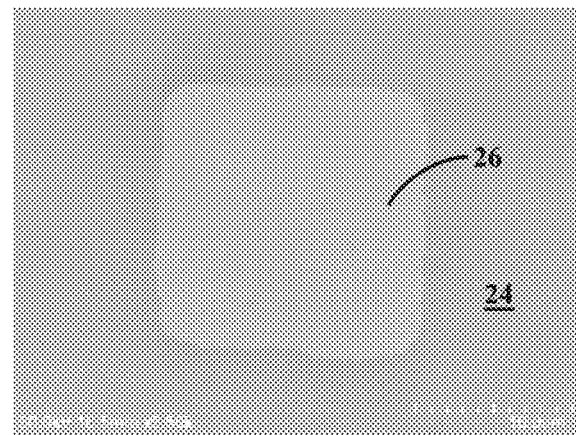
FIG. 10B is an SEM image of a second extension (e.g. gold nanopost) that is not washed with TBA Hydroxide and does not include any visible graphene oxide sheets disposed thereon.
Figure 10C:
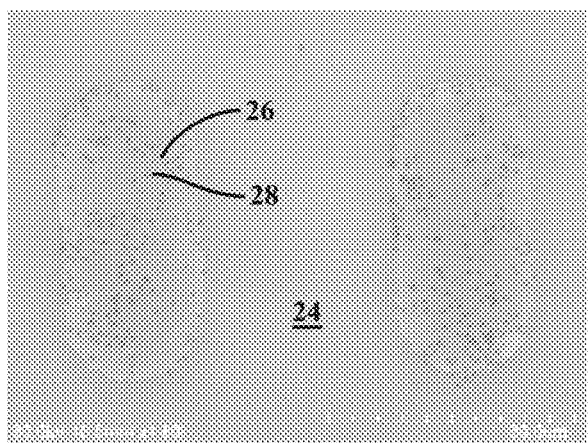
FIG. 10C is an SEM image of two extensions (e.g. gold nanoposts) that have been washed with TBA Hydroxide and include a plurality of graphene oxide sheets disposed thereon.
Figure 10D:
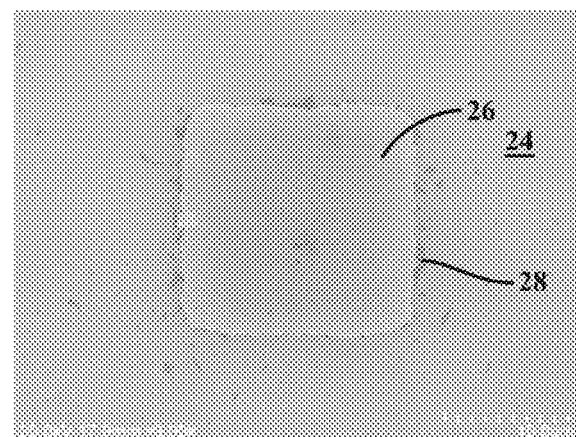
FIGS. 10D and 10E are SEM images of two additional extensions (e.g. gold nanoposts) that have been washed with TBA Hydroxide and include a plurality of graphene oxide sheets disposed thereon.
Figure 10E:
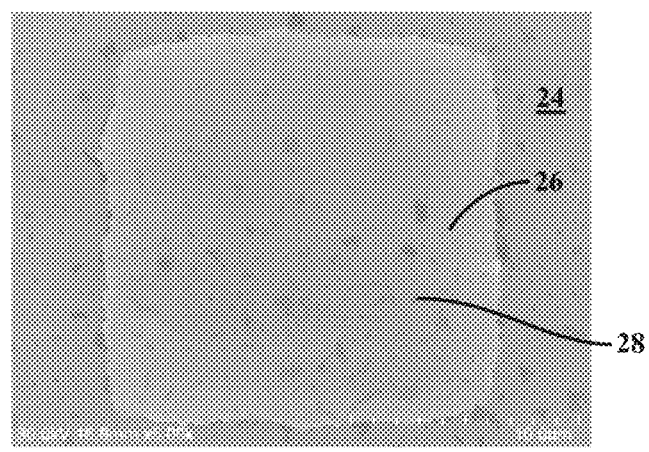

After formation of the microfluidic device and the functionalized graphene oxide described above, the PEG-functionalized graphene oxide is then flowed through the microfluidic device. By self-assembly, the functionalized graphene oxide molecules are directed to bridge arrays of the gold nanoposts on the silicon substrate which helps remove any extraneous coatings on the graphene oxide molecules and increases the electrical conductance of the microfluidic device (e.g. through an electrical annealing method). As a result of flowing the functionalized graphene oxide molecules through the microfluidic device, the functionalized graphene oxide molecules attach to the sides and tops of the gold nanoposts, as shown in FIG. 8, which is demonstrative of high selectivity of the deposition of functionalized graphene oxide molecules on the gold nanoposts as opposed to the $SiO_2$ supplemental layer and/or the PDMS supplemental layer. In addition, atomic force microscopy (AFM) is also utilized to characterize graphene oxide molecules disposed on the gold nanoposts. As set forth in FIGS. 9A and 9B, an average size of the functionalized graphene oxide molecules disposed on the gold nanoposts is on a nanometer scale and the approximate topographic height is about 1 to 1.5 nm. FIGS. 10A and 10B illustrate that little, if any, disposition of the functionalized graphene oxide on the gold nanoposts occurs if no TBA is used, as described above. FIGS. 10C-10E illustrate the there is plentiful disposition of the functionalized graphene oxide on gold nanoposts if TBA is used.

Subsequently, the supernatant (i.e., a solution of the PEG functionalized graphene oxide) is flowed through the microfluidic device at about 10 µL/min for 20 minutes. The microfluidic device is then washed using DI water and IPA at 100-300 µL/min for 10 minutes, respectively. FIGS. 11A and 11B illustrate that the washing with IPA and DI water significantly cleans the gold nanoposts of excess functionalized graphene oxide, which is desirable to increase the selectivity of the device to the targeted rare cells. The PEG functionalized graphene oxide disposed on the gold nanoposts is then further modified with fluorescently labeled NeutrAvidin to immobilize the biotinylated epithelial-cell adhesion molecule antibody (anti-EpCAM). EpCAM is a transmembrane glycoprotein that is frequently overexpressed in a variety of solid-tumor cells and is absent from hematologic cells. More specifically, a GMBS linker is prepared in a glove box and flowed through the microfluidic device at 10 µL/min for 30 minutes. The GMBS linker binds to the functionalized graphene oxide. Then, the microfluidic device is washed with Ethanol at 100 µL/min for about 15 min. Subsequently, the fluorescently labeled NeutrAvidin is applied to the microfluidic device at about 10 µL/min for 30 minutes and binds to the GMBS linker. As set forth in FIG. 12, fluorescence microscopy at varying exposure times and varying magnifications demonstrates that the fluorescently labeled NeutrAvidin successfully binds to the GMBS linker and, in turn, to the functionalized graphene oxide.

Then, the microfluidic device is washed using PBS at 100 µL/min for 10 minutes. Then, EpCAM, a CTC antibody, is flowed through the microfluidic device at 10 µL/min for two 30 minute intervals and binds to the fluorescently labeled NeutrAvidin. After washing the microfluidic device with PBS at 100 µL/min for about 10 minutes, a 1% BSA solution is flowed through the microfluidic device at 100 µL/min for about 10 minutes.

To further test the capture of actual cancer cells, a buffer solution of fluorescently labeled breast cancer cells (MCF-7) is formed wherein the cancer cell are present in a concentration of about 5,000 cells/mL. The buffer solution is then flowed through the microfluidic device at 10 µL/min for about 50 minutes. Finally, PBS and PFA are flowed through the microfluidic device at 100 µL/min for about 5 minutes, respectively.

Subsequently, the device is analyzed using fluorescence microscopy to determine whether any of the of fluorescently labeled breast cancer cells were captured by the EpCAM antibody. FIG. 13 illustrate that fluorescence is observed which is indicative that the fluorescently labeled breast cancer cells are captured by the device, and more specifically, through the use of the functionalized graphene oxide. The results also suggest that a high surface-to-volume ratio of the functionalized graphene oxide disposed on the gold nanoposts can generate 3D electrical surfaces that can significantly enhance detection limits and allow for highly reproducible detection of clinically important cancer markers.

Comparative Example

A control microfluidic device is also prepared using the same procedure as outlined above and washed with PBS except that no functionalized graphene oxide is utilized. In this control microfluidic device, the same fluorescently labeled NeutrAvidin is utilized at the same rates and amounts as described above. However, since there is no functionalized graphene oxide present, the fluorescently labeled NeutrAvidin does not bind. To verify that the fluorescently labeled NeutrAvidin does not bind to the nanoposts in the comparative example, the comparative device is examined using fluorescence microscopy, as described above. The results are set forth in FIGS. 14A/B and demonstrate that, at exposure times of even up to 1 second, no fluorescently labeled NeutrAvidin is seen. These result further highlight the sensitivity and specificity of the functionalized graphene oxide.

The results set forth above demonstrate the successful formation of an integrated nano microfluidic device with functionalized graphene oxide and gold using an orthogonal integrated translational approach and bioengineering tools to identify and bind CTCs of a breast cancer cell line as a model system. The aforementioned non-limiting approach utilizes self assembly of graphene oxide in a unique way for enhanced sensitivity and specificity as a detection tool. Graphene oxide has unique properties, such as increased 2D and 3D electrical conductivity, large surface area, superb mechanical flexibility, and increased chemical and thermal stability. The chemically derived and noncovalently functionalized graphene oxide described immediately above has the ability to overcome the limitations of carbon nanotubes (CNTs) such as variations in electrical properties of CNT-based devices and the limited surface area of CNTs.

One or more of the values described above may vary by ±5%, ±10%, ±15%, ±20%, ±25%, etc. so long as the variance remains within the scope of the disclosure. Unexpected results may be obtained from each member of a Markush group independent from all other members. Each member may be relied upon individually and or in combination and provides adequate support for specific embodiments within the scope of the appended claims. The subject matter of all combinations of independent and dependent claims, both singly and multiply dependent, is herein expressly contemplated. The disclosure is illustrative including words of description rather than of limitation. Many modifications and variations of the present disclosure are possible in light of the above teachings, and the disclosure may be practiced otherwise than as specifically described herein.

What is claimed is:

1. A system for detecting cells, said system comprising:
   A. a substrate and
      one or more supplemental layers disposed on said substrate, wherein said one or more supplemental layers have a height ranging from 0.1 millimeters to 100 millimeters;
   B. an extension coupled to one of said one or more supplemental layers and extending outwardly from said substrate; and
   C. a functionalized graphene oxide disposed on said extension, wherein said functionalized graphene oxide includes a functionalization comprising a binding agent for interaction with the cells to immobilize the cells on said extension when the cells come into contact with said functionalized graphene oxide.

2. The system of claim 1 wherein said functionalized graphene oxide has a thickness of from 1 to 5 nanometers.

3. The system of claim 2 wherein said extension is gold.

4. The system of claim 1 wherein said binding agent comprises phospholipid-polyethylene-glyco-amine.

5. The system of claim 1 wherein said binding agent comprises a reaction product of phospholipid-polyethylene-glyco-amine and N-γ-maleimidobutyryloxy succinimide ester.

6. The system of claim 5 wherein said reaction product is bonded to a protein.

7. The system of claim 6 wherein said protein is a deglycosylated form of avidin.

8. The system of claim 6 wherein said protein is bonded to an antibody for interaction with the cells.

9. The system of claim 8 wherein said antibody is an anti-EpCAM antibody.

10. The system of claim 1 wherein said binding agent comprises a reaction product of phospholipid-polyethylene-glyco-amine and N-γ-maleimidobutyryloxy succinimide ester, wherein said reaction product is further bonded to a protein, and wherein said protein is further bonded to an antibody for interaction with the cells.

11. The system of claim 1 that is further defined as a microfluidic device.

12. The system of claim 1, wherein at least one of said one or more supplemental layers is selected from the group consisting of a polydimethylsiloxane layer, a polyethylene terephthalate layer, a polyimide layer, and a polyether ether ketone layer.

13. The system of claim 1, wherein the cells comprise one or more of circulating tumor cells, endothelial cells, fetal cells, and cells of hemopoetic origin.

14. The system of claim 1, wherein the extension has a height of from 1 to 500 nanometers.

15. A microfluidic device for detecting cells, said device comprising:
   A. a silicon substrate and
      one or more supplemental layers disposed on said substrate, wherein said one or more supplemental layers have a height ranging from 0.1 millimeters to 100 millimeters;
   B. an extension that is a metal, that is coupled to one of said one or more supplemental layers, and that extends outwardly from said substrate; and
   C. a functionalized graphene oxide disposed on said extension, wherein said functionalized graphene oxide includes a functionalization comprising a binding agent for interaction with the cells to immobilize the cells on said extension when the cells come into contact with said functionalized graphene oxide.

16. The microfluidic device of claim 15 wherein said metal is gold, said graphene oxide is functionalized with a binding agent, said binding agent comprises a reaction product of phospholipid-polyethylene-glyco-amine and N-γ-maleimidobutyryloxy succinimide ester, said reaction product is further bonded to a protein, and said protein is further bonded to an antibody for interaction with the cells.

17. The microfluidic device of claim 15, wherein at least one of said one or more supplemental layers is selected from the group consisting of a polydimethylsiloxane layer, a polyethylene terephthalate layer, a polyimide layer, and a polyether ether ketone layer.

18. A method for capturing cells using a system comprising a substrate and one or more supplemental layers disposed on said substrate, an extension coupled to one of said one or more supplemental layers and extending outwardly from said substrate with the one or more supplemental layers having a height of from 0.1 millimeters to 100 millimeters, and a functionalized graphene oxide disposed on the extension, said method comprising the steps of:

I. providing the system;
II. introducing a sample of bodily fluid containing the cells into the system; and
III. immobilizing the cells on the extension as the cells interact with the functionalized graphene oxide when the cells come into contact with the functionalized graphene oxide.

19. The method of claim 18 wherein the functionalized graphene oxide has a thickness of from 1 to 5 nanometers.

20. The method of claim 18 wherein the extension is gold.

21. The method of claim 20 wherein the graphene oxide is functionalized with a binding agent, wherein the binding agent comprises a reaction product of phospholipid-polyethylene-glyco-amine and N-γ-maleimidobutyryloxy succinimide ester, wherein the reaction product is further bonded to a protein, and wherein the protein is further bonded to an antibody for interaction with the cells.

22. The method of claim 18, wherein at least one of said one or more supplemental layers is selected from the group consisting of a polydimethylsiloxane layer, a polyethylene terephthalate layer, a polyimide layer, and a polyether ether ketone layer.

\* \* \* \* \*